United States Patent
Oberdorf et al.

[11] Patent Number: 6,114,363
[45] Date of Patent: Sep. 5, 2000

[54] PYRIDYL PHENYL AND BENZYL ETHERS, PROCESS AND INTERMEDIATE PRODUCTS FOR THEIR PREPARATION AND THEIR USE AS FUNGICIDES AND FOR CONTROLLING ANIMAL PESTS

[75] Inventors: Klaus Oberdorf, Heidelberg; Wassilios Grammenos, Ludwigshafen; Hubert Sauter, Mannheim; Thomas Grote, Schifferstadt; Bernd Müller, Frankenthal; Reinhard Kirstgen, Neustadt; Ruth Müller, Friedelsheim; Herbert Bayer, Mannheim; Arne Ptock, Ludwigshafen; Michael Rack, Heidelberg; Albrecht Harreus, Ludwigshafen; Franz Röhl, Schifferstadt; Gisela Lorenz, Hambach; Eberhard Ammermann, Heppenheim; Siegfried Strathmann, Limburgerhof; Volker Harries, Frankenthal, all of Germany

[73] Assignee: BASF Aktiengesellschaft, Ludwigshafen, Germany

[21] Appl. No.: 09/117,702
[22] PCT Filed: Feb. 17, 1997
[86] PCT No.: PCT/EP97/00736
  § 371 Date: Aug. 4, 1998
  § 102(e) Date: Aug. 4, 1998
[87] PCT Pub. No.: WO97/30032
  PCT Pub. Date: Aug. 21, 1997

[30] Foreign Application Priority Data

Feb. 17, 1996 [DE] Germany ............ 196 05 903

[51] Int. Cl.⁷ ............................................. A01N 43/40
[52] U.S. Cl. .................. 514/345; 514/348; 546/296; 546/300
[58] Field of Search .................. 546/296, 300; 504/244; 514/345, 348

[56] References Cited

U.S. PATENT DOCUMENTS 5,523,454  6/1996  Brand et al. .................. 558/408
5,554,578  9/1996  Wenderoth et al. .................. 504/130

FOREIGN PATENT DOCUMENTS 278595   8/1988   European Pat. Off. .
398692  11/1990   European Pat. Off. .

*Primary Examiner*—Alan L. Rotman
*Attorney, Agent, or Firm*—Keil & Weinkauf

[57] ABSTRACT

Pyridyl phenyl and pyridyl benzyl ethers of the formula I

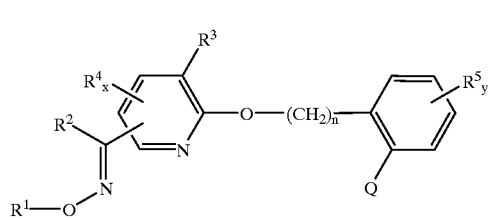

and their salts and N-oxides where the substituent and indices have the following meanings:

Q is $C(CO_2CH_3)=CHCl_3$, $C(CO_2CH_3)=CHOCH_3$, $C(CONH_2)=NOCH_3$, $C(CO_2CH_3)=NOCH_3$, $C(CONHCH_3)=NOCH_3$ or $N(OCH_3)—CO_2CH_3$;

n is 0 or 1;

$R^1$ is hydrogen or an organic radical linked via a carbon atom;

$R^2$ is hydrogen, cyano, halogen or an organic radical linked via a carbon, oxygen, sulfur or nitrogen atom;

$R^3$ is hydrogen, halogen, $C_1$–$C_4$-alkyl or $C_1$–$C_2$-haloalkyl;

x is 0, 1 or 2;

$R^4$ is cyano, nitro, halogen or an organic radical linked via a carbon, oxygen, sulfur or nitrogen atom;

y is 0, 1, 2 or 3;

$R^5$ is cyano, halogen, $C_1$–$C_4$-alkyl, $C_1$–$C_4$-haloalkyl or $C_1$–$C_4$-alkoxy, processes and intermediates for their preparation and their use.

4 Claims, No Drawings

PYRIDYL PHENYL AND BENZYL ETHERS, PROCESS AND INTERMEDIATE PRODUCTS FOR THEIR PREPARATION AND THEIR USE AS FUNGICIDES AND FOR CONTROLLING ANIMAL PESTS

The present invention relates to pyridyl phenyl and pyridyl benzyl ethers of the formula I

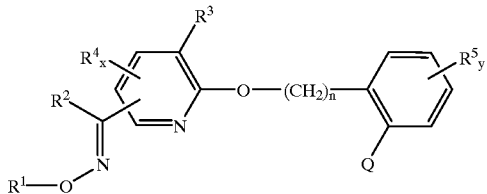

and their salts and N-oxides where the substituent and indices have the following meanings:

Q is $C(CO_2CH_3)=CHCH_3$, $C(CO_2CH_3)=CHOC_3$, $C(CONH_2)=NOCH_3$, $C(CO_2CH_3)=NOCH_3$, $C(CONCH_3)=NOCH_3$ or $N(OCH_3)-CO_2CH_3$;

n is 0 or 1;

$R^1$ is hydrogen or an organic radical linked via a carbon atom;

$R^2$ is hydrogen, cyano, halogen or an organic radical linked via a carbon, oxygen, sulfur or nitrogen atom;

$R^3$ is hydrogen, halogen, $C_1-C_4$-alkyl or $C_1-C_2$-haloalkyl;

x is 0, 1 or 2, it being possible for the radicals $R^4$ to be different if x is 2;

$R^4$ is cyano, nitro, halogen or an organic radical linked via a carbon, oxygen, sulfur or nitrogen atom;

y is 0, 1, 2 or 3, it being possible for the radicals $R^5$ to be different if y is 2 or 3;

$R^5$ is cyano, halogen, $C_1-C_4$-alkyl, $C_1-C_4$-haloalkyl or $C_1-C_4$-alkoxy.

Furthermore the invention relates to processes and intermediates for the preparation of these compounds and to their use for controlling animal pests and harmful fungi.

Pyridyl phenyl and pyridyl benzyl ethers having fungicidal, or fungicidal and insecticidal, properties and which differ from the compounds according to the invention by the substituent in the pyridyl moiety have been disclosed in the literature (EP-A 254 426; EP-A 278 595; EP-A 299 694; EP-A 363 818; EP-A 350 691; EP-A 398 692; EP-A 407 873; EP-A 477 631; EP-A 513 580; JP-A 04/182,461; WO-A 93/15,046).

It was an object of the present invention to provide compounds with an improved activity and a widened spectrum of action.

We have found that this object is achieved by the compounds I defined at the outset. Furthermore, we have found processes and intermediates for the preparation of these compounds, and their use for controlling animal pests and harmful fungi.

The compounds I are accessible via various routes by processes described per se in the literature.

For example, the synthesis of group Q is disclosed in the literature cited at the outset and is carried out in general and in particular by the processes described therein.

When synthesizing the compounds I, a procedure is usually followed in which a pyridine derivative of the formula IIa is converted with a phenol or a benzyl alcohol of the formula IIIa in an inert solvent to give the corresponding ether of the formula IVa, and IV is subsequently reacted with an O-substituted hydroxylamine ($R^1$—O—$NH_2$) or a salt thereof to give I.

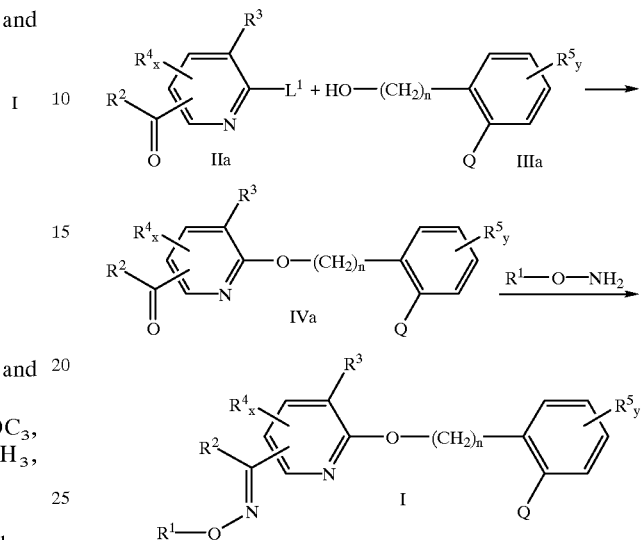

$L^1$ in formula IIa is a nucleophilically exchangeable leaving group such as halogen (eg. fluorine, chlorine, bromine or iodine) or alkyl- or arylsulfonate (eg. methylsulfonate, trifluoromethylsulfonate, phenylsulfonate or methylphenylsulfonate).

1a) The reaction of IIa with IIIa is normally carried out in an inert solvent at from 0° C. to 130° C., preferably 20° C. to 80° C., in the presence of a base.

Suitable solvents are aliphatic hydrocarbons such as pentane, hexane, cyclohexane and petroleum ether, aromatic hydrocarbons such as toluene, o-, m- and p-xylene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and also dimethyl sulfoxide and dimethylformamide, especially preferably tetrahydrofuran, acetonitrile, dimethyl sulfoxide and acetone. Mixtures of these can also be used.

Bases which are suitable are, in general, inorganic compounds such as alkali metal hydroxides and alkaline earth metal hydroxides, such as lithium hydroxide, sodium hydroxide, potassium hydroxide and calcium hydroxide, alkali metal oxides and alkaline earth metal oxides, such as lithium oxide, sodium oxide, calcium oxide and magnesium oxide, alkali metal hydrides and alkaline earth metal hydrides, such as lithium hydride, sodium hydride, potassium hydride and calcium hydride, alkali metal amides, such as lithium amide, sodium amide and potassium amide, alkali metal carbonates and alkaline earth metal carbonates, such as lithium carbonate and calcium carbonate, and also alkali metal hydrogen carbonates, such as sodium hydrogen carbonate, organometallic compounds, in particular alkali metal alkyls, such as methyllithium, butyllithium and phenyllithium, alkylmagnesium halides, such as methylmagnesium chloride, and alkali metal alcoholates and alkaline earth metal alcoholates, such as sodium methanolate, sodium ethanolate, potassium ethanolate, potassium tert-butanolate and dimethoxymagnesium, moreover organic bases, eg. tertiary amines, such as trimethylamine, triethylamine, triisopropylethylamine and n-methylpiperidine, pyridine, substituted pyridines, such as collidine, lutidine and 4-dimethylaminopyridine, and also bicyclic amines. Especially preferred substances are potassium carbonate, sodium hydride and potassium tert-butylate. In general, the bases are employed in catalytic amounts, but they can also be used in equimolar amounts, in excess or, if appropriate, as the solvent.

In general, the starting materials are reacted with each other in equimolar amounts. To obtain higher yields, it may be advantageous to employ IIa in an excess, based on IIIa.

1b) The reaction of IVa with the O-substituted hydroxylamine or a salt thereof is normally carried out in an inert solvent at from 0° C. to 80° C., preferably 20° C. to 60° C., in the presence or absence of an acid or in the presence or absence of a base if the O-substituted hydroxylamine is liberated from its salt.

Suitable solvents are aliphatic hydrocarbons such as pentane, hexane, cyclohexane and petroleum ether, aromatic hydrocarbons such as toluene, o-, m- and p-xylene, halogenated hydrocarbons, such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, alcohols such as methanol, ethanol, n-propanol, isopropanol, n-butanol and tert-butanol, and also dimethyl sulfoxide, dimethylformamide and pyridine, especially preferably methanol and pyridine. Mixtures of these can also be used.

Bases which are suitable are, in general, inorganic compounds such as alkali metal hydroxides and alkaline earth metal hydroxides, such as lithium hydroxide, sodium hydroxide, potassium hydroxide and calcium hydroxide, alkali metal oxides and alkaline earth metal oxides, such as lithium oxide, sodium oxide, calcium oxide and magnesium oxide, alkali metal hydrides and alkaline earth metal hydrides, such as lithium hydride, sodium hydride, potassium hydride and calcium hydride, alkali metal amides, such as lithium amide, sodium amide and potassium amide, alkali metal-carbonates and alkaline earth metal carbonates, such as lithium carbonate and calcium carbonate, and also alkali metal hydrogen carbonates, such as sodium hydrogen carbonate, organometallic compounds, in particular alkali metal alkyls, such as methyllithium, butyllithium and phenyllithium, alkylmagnesium halides, such as methylmagnesium chloride, and alkali metal alcoholates and alkaline earth metal alcoholates, such as sodium methanolate, sodium ethanolate, potassium ethanolate, potassium tert-butanolate and dimethoxymagnesium, moreover organic bases, eg. tertiary amines, such as trimethylamine, triethylamine, triisopropylethylamine and N-methylpiperidine, pyridine, substituted pyridines, such as collidine, lutidine and 4-dimethylaminopyridine, and also bicyclic amines. Especially preferred substances are pyridine and sodium hydroxide. In general, the bases are employed in catalytic amounts, but they can also be used in equimolar amounts, in an excess or, if appropriate, as solvent.

Acids and acidic catalysts which are used are inorganic acids such as hydrofluoric acid, hydrochloric acid, hydrobromic acid, sulfuric acid and perchloric acid, Lewis acids, such as boron trifluoride, aluminum trichloride, iron(III) chloride, tin(IV) chloride, titanium (IV) chloride and zinc(II) chloride, and also organic acids such as formic acid, acetic acid, propionic acid, oxalic acid, citric acid and trifluoroacetic acid. In general, the acids are employed in catalytic amounts.

In general, the starting materials are reacted with each other in equimolar amounts. To obtain higher yields, it may be advantageous to employ the hydroxylamine, or its salt, in an excess based on IVa.

In a similar manner, the compounds I are obtained by first converting a pyridine derivative of the formula IIa with an O-substituted hydroxylamine ($R^1$—O—$NH_2$) or a salt thereof to give the corresponding compound of the formula Va and subsequently reacting Va with a phenol or a benzyl alcohol of the formula IIIa in an inert solvent to give I.

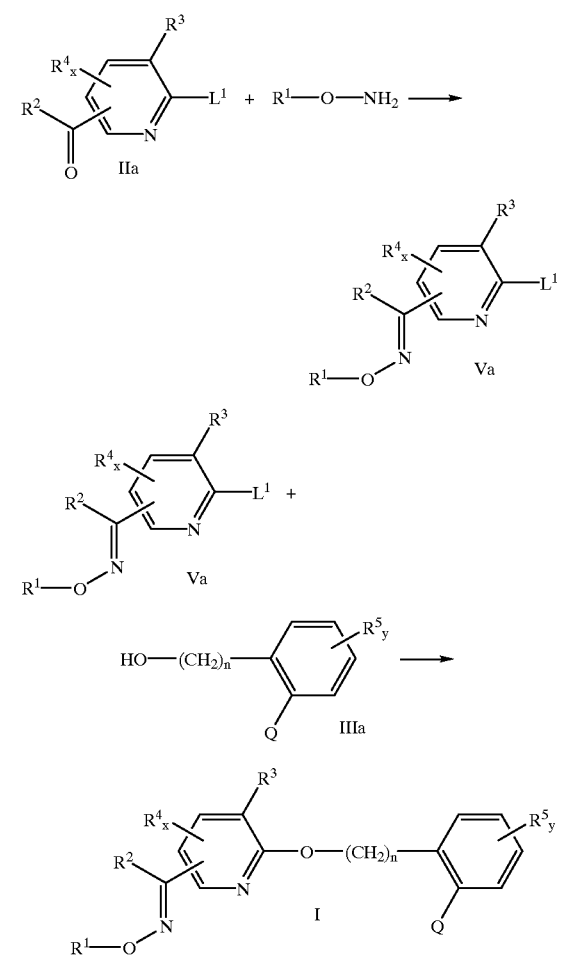

The reactions are carried out in general and in particular by the above-described methods.

Compounds I where n is 1 are preferably obtained by converting a pyridine alcohol of the formula IIb with a benzyl compound of the formula IIIb in an inert solvent to give the corresponding benzyl ether of the formula IVb and subsequently reacting IVb with an O-substituted hydroxylamine ($R^1$—O—$NH_2$) or a salt thereof to give I.

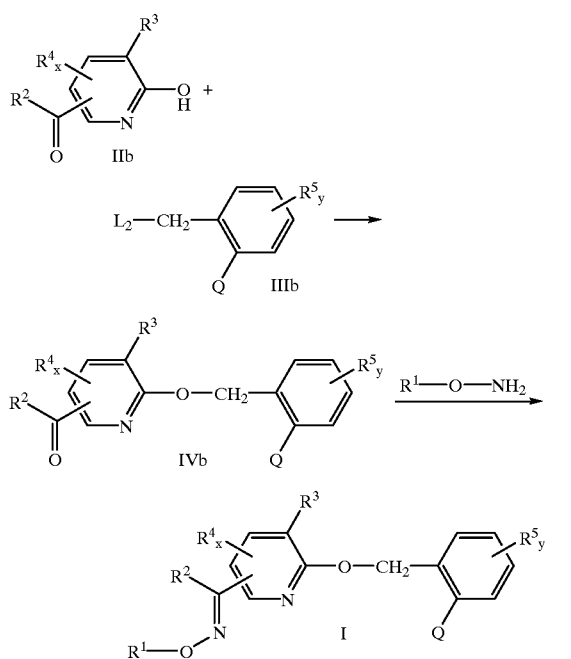

L² in formula IIIb is a nucleophilically exchangeable leaving group such as halogen (eg. chlorine, bromine or iodine) or alkyl- or arylsulfonate (eg. methylsulfonate, trifluoromethylsulfonate, phenylsulfonate or methylphenylsulfonate).

2a) The reaction of IIb with IIIb is normally carried out in an inert solvent at from 0° C. to 130° C., preferably 20° C. to 60° C., in the presence of a base.

Suitable solvents are aliphatic hydrocarbons such as pentane, hexane, cyclohexane and petroleum ether, aromatic hydrocarbons such as toluene, o-, m- and p-xylene, halogenated hydrocarbons, such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and also dimethyl sulfoxide and dimethylformamide, especially preferably tetrahydrofuran, acetonitrile, dimethyl sulfoxide and acetone. Mixtures of these can also be used.

Bases which are suitable are, in general, inorganic compounds such as alkali metal hydroxides and alkaline earth metal hydroxides, such as lithium hydroxide, sodium hydroxide, potassium hydroxide and calcium hydroxide, alkali metal oxides and alkaline earth metal oxides, such as lithium oxide, sodium oxide, calcium oxide and magnesium oxide, alkali metal hydrides and alkaline earth metal hydrides, such as lithium hydride, sodium hydride, potassium hydride and calcium hydride, alkali metal amides, such as lithium amide, sodium amide and potassium amide, alkali metal carbonates and alkaline earth metal carbonates, such as lithium carbonate and calcium carbonate, and also alkali metal hydrogen carbonates, such as sodium hydrogen carbonate, organometallic compounds, in particular alkali metal alkyls, such as methyllithium, butyllithium and phenyllithium, alkylmagnesium halides, such as methylmagnesium chloride, and alkali metal alcoholates and alkaline earth metal alcoholates, such as sodium methanolate, sodium ethanolate, potassium ethanolate, potassium tert-butanolate and dimethoxymagnesium, moreover organic bases, eg. tertiary amines, such as trimethylamine, triethylamine, triisopropylethylamine and N-methylpiperidine, pyridine, substituted pyridines, such as collidine, lutidine and 4-dimethylaminopyridine, and also bicyclic amines. Especially preferred substances are potassium carbonate, sodium hydride and potassium tert-butylate. In general, the bases are employed in catalytic amounts, but they can also be used in equimolar amounts, in an excess or, if appropriate, as the solvent.

In general, the starting materials are reacted with each other in equimolar amounts. To obtain higher yields, it may be advantageous to employ IIb in an excess based on IIIb.

2b) The reaction of IVb with the O-substituted hydroxylamine or its salt is carried out in general and in particular under the conditions described above under item 1b.

Suitable solvents are aliphatic hydrocarbons such as pentane, hexane, cyclohexane and petroleum ether, aromatic hydrocarbons such as toluene, o-, m- and p-xylene, halogenated hydrocarbons, such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, alcohols such as methanol, ethanol, n-propanol, isopropanol, n-butanol and tert-butanol, and also dimethyl sulfoxide, dimethylformamide and pyridine, especially preferably methanol and pyridine. Mixtures of these can also be used.

Bases which are suitable are, in general, inorganic compounds such as alkali metal hydroxides and alkaline earth metal hydroxides, such as lithium hydroxide, sodium hydroxide, potassium hydroxide and calcium hydroxide, alkali metal oxides and alkaline earth metal oxides, such as lithium oxide, sodium oxide, calcium oxide and magnesium oxide, alkali metal hydrides and alkaline earth metal hydrides, such as lithium hydride, sodium hydride, potassium hydride and calcium hydride, alkali metal amides, such as lithium amide, sodium amide and potassium amide, alkali metal carbonates and alkaline earth metal carbonates, such as lithium carbonate and calcium carbonate, and also alkali metal hydrogen carbonates, such as sodium hydrogen carbonate, organometallic compounds, in particular alkali metal alkyls, such as methyllithium, butyllithium and phenyllithium, alkylmagnesium halides, such as methylmagnesium chloride, and alkali metal alcoholates and alkaline earth metal alcoholates, such as sodium methanolate, sodium ethanolate, potassium ethanolate, potassium tert-butanolate and dimethoxymagnesium, moreover organic bases, eg. tertiary amines, such as trimethylamine, triethylamine, triisopropylethylamine and N-methylpiperidine, pyridine, substituted pyridines, such as collidine, lutidine and 4-dimethylaminopyridine, and also bicyclic amines. Especially preferred substances are pyridine and sodium hydroxide. In general, the bases are employed in catalytic amounts, but they can also be used in equimolar amounts, in an excess or, if appropriate, as solvent.

Acids and acidic catalysts which are used are inorganic acids such as hydrofluoric acid, hydrochloric acid, hydrobromic acid, sulfuric acid and perchloric acid, Lewis acids, such as boron trifluoride, aluminum trichloride, iron(III) chloride, tin(IV) chloride, titanium (IV) chloride and zinc(II) chloride, and also organic acids such as formic acid, acetic acid, propionic acid, oxalic acid, citric acid and trifluoroacetic acid. In general, the acids are employed in catalytic amounts.

In general, the starting materials are reacted with each other in equimolar amounts. To obtain higher yields, it may be advantageous to employ IIb in an excess, based on IIIb.

In a similar manner, the compounds I where n is 1 are obtained by first converting a pyridine alcohol of the formula IIb with an O-substituted hydroxylamine ($R^1$—O—$NH_2$) or a salt thereof to give the corresponding compound of the formula Vb and subsequently reacting Vb with a benzyl compound of the formula IIIb in an inert solvent to give I.

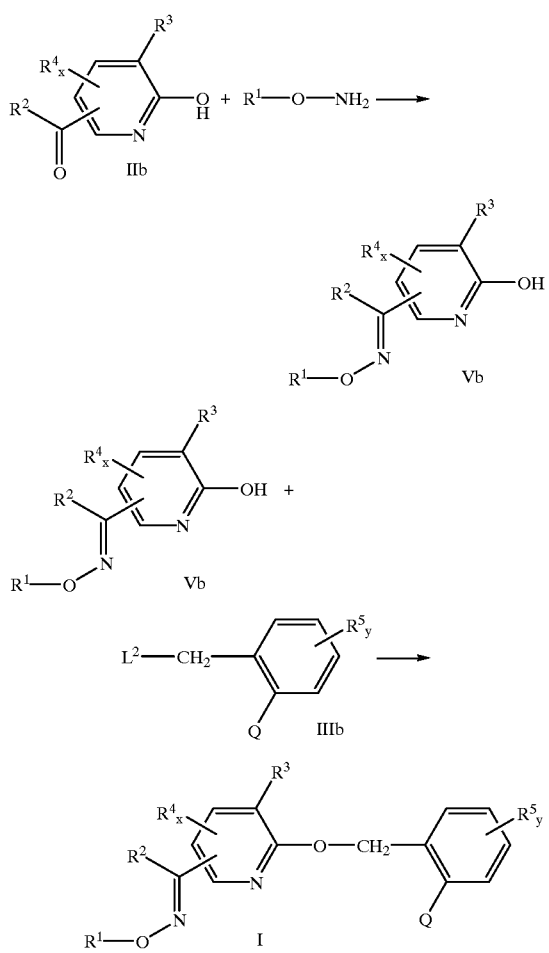

The reactions are carried out in general and in particular by the methods described above.

Those starting materials of the formulae IIIa and IIIb which are required for the preparation of the compounds I by the processes described above and which are not already known from the literature mentioned at the outset can be prepared in a similar manner following the processes described in these publications.

The starting materials of the formula IIa can be obtained by reacting a suitably substituted pyridine of the formula VIa with an activated carboxylic acid of the formula VIIa in an inert solvent in the presence of an organometallic base [cf. J. Organomet. Chem. 56 (1973), 53–66; Chem. Ber. 125 (1992), 1169–1190].

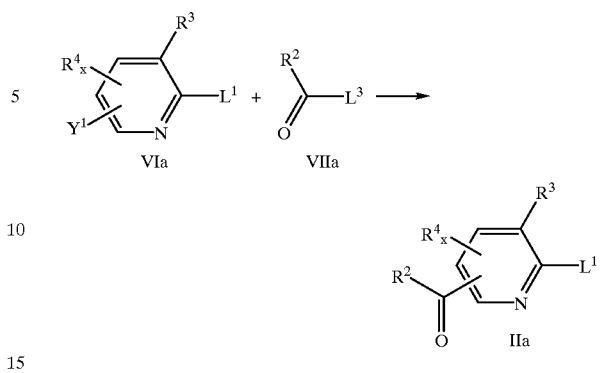

$Y^1$ in formula VIa is a halogen atom, eg. fluorine, chlorine, bromine and iodine, especially bromine and iodine.

$L^3$ in formula VII is a halogen atom, eg. fluorine, chlorine, bromine and iodine, especially chlorine, or an amide or ester radical. It is also possible to employ a corresponding cyanide $R^2$—C≡N instead of the compound VIIa.

This reaction is normally carried out in an inert solvent in the presence of an organometallic base at from $-75°$ C. to $40°$ C., preferably $-75°$ C. to $0°$ C.

Suitable solvents are aliphatic hydrocarbons such as pentane, hexane, cyclohexane and petroleum ether, aromatic hydrocarbons such as toluene, o-, m- and p-xylene, ethers such as diethyl ether, diisopropyl ether, tert-butyl methyl ether, dioxane, anisole and tetrahydrofuran, and also dimethyl sulfoxide and dimethylformamide, especially preferably diethyl ether and tetrahydrofuran. Mixtures of these can also be used.

Suitable organometallic bases are organometallic compounds in general, in particular alkali metal alkyls, such as methyllithium, butyllithium and phenyllithium, alkylmagnesium halides, such as methylmagnesium chloride. n-Butyllithium is especially preferred. In general, the bases can be employed in equimolar amounts or in an excess.

In general, the starting materials are reacted with each other in equimolar amounts. To obtain higher yields, it may be advantageous to employ VIIa in an excess based on VIa.

In a further method, the compounds IIa are also obtained by reacting a pyridinecarbonyl halide of the general formula VIIIa with an organometallic compound ($R^2$-M; M is the equivalent of a metal ion) in an inert solvent [cf. DE-A 38 38 243; EP-A 446 872].

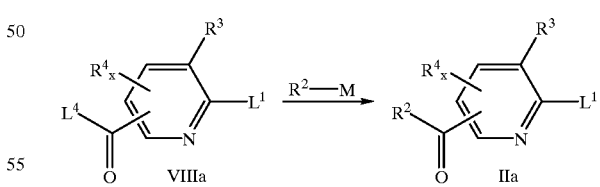

Metals which are especially suitable are lithium, magnesium, copper and zinc.

$L^4$ in formula VIIIa is a halogen atom, eg. fluorine, chlorine, bromine and iodine, especially chlorine.

This reaction is normally carried out in an inert solvent at from $-80°$ C. to $20°$ C., preferably $-75°$ C. to $0°$ C.

Suitable solvents are aliphatic hydrocarbons such as pentane, hexane, cyclohexane and petroleum ether, aromatic hydrocarbons such as toluene, o-, m- and p-xylene, ethers such as diethyl ether, diisopropyl ether, tert-butyl methyl ether, dioxane, anisole and tetrahydrofuran, especially preferably diethyl ether and tetrahydrofuran. Mixtures of these can also be used.

In general, the starting materials are reacted with each other in equimolar amounts. To obtain higher yields, it may be advantageous for the yield to employ the organometallic compound in an excess, based on VIIIa.

According to a further method, the compounds IIa are also obtained by converting a pyridinecarbonyl halide of the general formula VIIIa with a malonic ester of the formula IX in an inert solvent to give the corresponding triketone VIIIb and subsequently reacting VIIIb to give IIa [cf. Tetrahedron 48 (22) (1992), 9233].

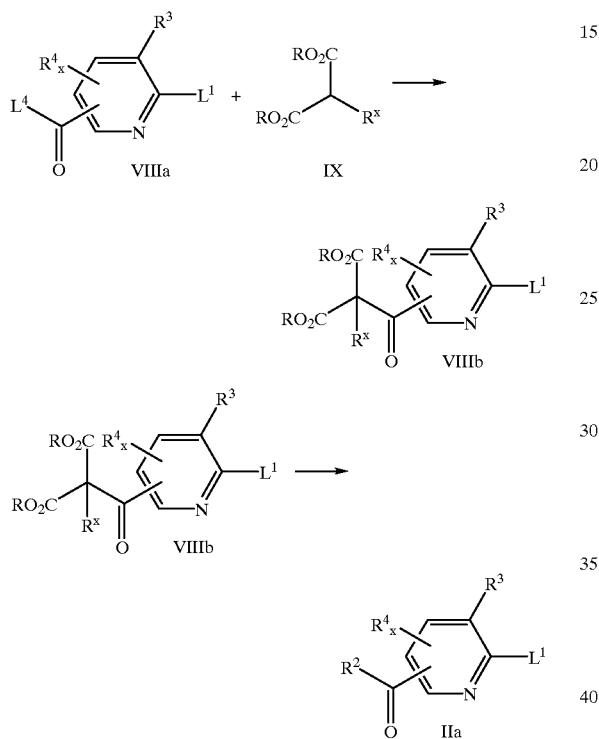

$R^x$ in formulae VIIIb and IX is the radical of a group $R^2$.

Radicals R in formulae VIIIb and IX are $C_1$–$C_4$-alkyl groups which are independent of one another, in particular methyl and ethyl.

3a) The reaction of VIIIa and IX is normally carried out in an inert solvent at from 0° C. to 120° C., preferably 20° C. to 80° C., in the presence of a base and in the presence or absence of a Lewis acid, such as magnesium chloride.

Suitable solvents are aliphatic hydrocarbons such as pentane, hexane, cyclohexane and petroleum ether, aromatic hydrocarbons such as toluene, o-, m- and p-xylene, halogenated hydrocarbons, such as methylene chloride, chloroform and chlorobenzene, ethers such as diethyl ether, diisopropyl ether, tert-butyl methyl ether, dioxane, anisole and tetrahydrofuran, nitrites such as acetonitrile and propionitrile, ketones such as acetone, methyl ethyl ketone, diethyl ketone and tert-butyl methyl ketone, and also dimethyl sulfoxide and dimethylformamide, especially preferably toluene. Mixtures of these can also be used.

Bases which are suitable are, in general, inorganic compounds such as alkali metal hydroxides and alkaline earth metal hydroxides, such as lithium hydroxide, sodium hydroxide, potassium hydroxide and calcium hydroxide, alkali metal oxides and alkaline earth metal oxides, such as lithium oxide, sodium oxide, calcium oxide and magnesium oxide, alkali metal hydrides and alkaline earth metal hydrides, such as lithium hydride, sodium hydride, potassium hydride and calcium hydride, alkali metal amides, such as lithium amide, sodium amide and potassium amide, alkali metal carbonates and alkaline earth metal carbonates, such as lithium carbonate and calcium carbonate, and also alkali metal hydrogen carbonates, such as sodium hydrogen carbonate, organometallic compounds, in particular alkali metal alkyls, such as methyllithium, butyllithium and phenyllithium, alkylmagnesium halides, such as methylmagnesium chloride, and alkali metal alcoholates and alkaline earth metal alcoholates, such as sodium methanolate, sodium ethanolate, potassium ethanolate, potassium tert-butanolate and dimethoxymagnesium, moreover organic bases, eg. tertiary amines, such as trimethylamine, triethylamine, triisopropylethylamine and N-methylpiperidine, pyridine, substituted pyridines, such as collidine, lutidine and 4-dimethylaminopyridine, and also bicyclic amines. Especially preferred substances are sodium hydroxide and triethylamine. In general, the bases are employed in equimolar amounts, but they can also be used in an excess or, if appropriate, as the solvent.

In general, the starting materials are reacted with each other in equimolar amounts. To obtain higher yields, it may be advantageous to employ IX in an excess, based on VIIIa.

3b) The decarboxylation of VIIIb to IIa is normally carried out in an inert solvent at from 60° C. to 200° C., preferably 100° C. to 160° C., in the presence or absence of a base.

Suitable solvents are aromatic hydrocarbons such as toluene, o-, m- and p-xylene, halogenated hydrocarbons such as chlorobenzene, nitriles such as acetonitrile and propionitrile, alcohols such as methanol, ethanol, n-propanol, isopropanol, n-butanol and tert-butanol, and also dimethyl sulfoxide and dimethylformamide, especially preferably water and dimethyl sulfoxide. Mixtures of these can also be used.

Bases which are suitable are, in general, inorganic compounds such as alkali metal hydroxides and alkaline earth metal hydroxides, such as lithium hydroxide, sodium hydroxide, potassium hydroxide and calcium hydroxide, alkali metal oxides and alkaline earth metal oxides, such as lithium oxide, sodium oxide, calcium oxide and magnesium oxide, alkali metal hydrides and alkaline earth metal hydrides, such as lithium hydride, sodium hydride, potassium hydride and calcium hydride, alkali metal amides, such as lithium amide, sodium amide and potassium amide, alkali metal carbonates and alkaline earth metal carbonates, such as lithium carbonate and calcium carbonate, and also alkali metal hydrogen carbonates, such as sodium hydrogen carbonate, organometallic compounds, in particular alkali metal alkyls, such as methyllithium, butyllithium and phenyllithium, alkylmagnesium halides, such as methylmagnesium chloride, and alkali metal alcoholates and alkaline earth metal alcoholates, such as sodium methanolate, sodium ethanolate, potassium ethanolate, potassium tert-butanolate and dimethoxymagnesium, moreover organic bases, eg. tertiary amines, such as trimethylamine, triethylamine, triisopropylethylamine and N-methylpiperidine, pyridine, substituted pyridines, such as collidine, lutidine and 4-dimethylaminopyridine, and also bicyclic amines. Especially preferred substances are sodium hydroxide and sodium methanolate. In general, the bases are employed in catalytic amounts, but they can also be used in equimolar amounts, in an excess or, if appropriate, as the solvent.

The starting materials of the formula IIb are obtained by converting a suitably substituted pyridine derivative of the formula VIa with an alcoholate (R'—O—M$^-$; R' is $C_1$–$C_4$-alkyl, M$^+$ is the equivalent of an alkali metal cation or alkaline earth metal cation, in particular sodium or potassium) in the presence of a base to give the corresponding alkyl pyridyl ether of the formula VIb, subsequently converting VIb by reaction with an activated carboxylic acid of the formula VIIa in a manner similar to the process described above (reaction of VIa) to give the corresponding ether IIc and subsequently cleaving IIc to give IIb.

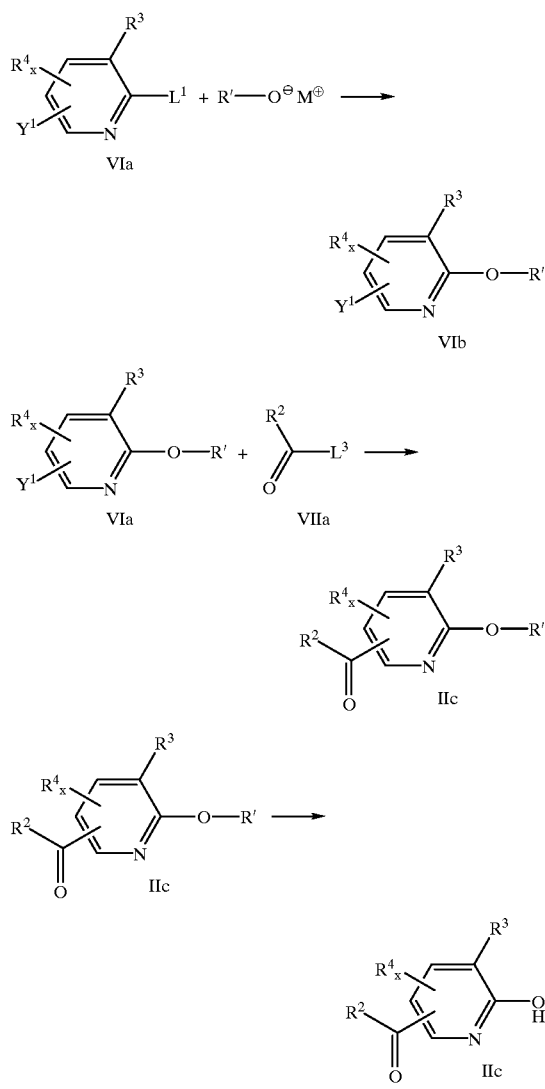

4a) The etherification of VIa to VIb is normally carried out at from 0° C. to 120° C., preferably 20° C. to 80° C., in the presence of an inert solvent.

Suitable solvents are aliphatic hydrocarbons such as pentane, hexane, cyclohexane and petroleum ether, aromatic hydrocarbons such as toluene, o-, m- and p-xylene, halogenated hydrocarbons, such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and also dimethyl sulfoxide and dimethylformamide, especially preferably dimethylformamide. Mixtures of these can also be used.

In general, the pyridine derivative VIa and the alcoholate are reacted with each other in equimolar amounts. To obtain higher yields, it may be advantageous to employ the alcoholate in an excess based on VIa, or as the solvent.

4b) The reaction of the ether VIb with the activated carboxylic acid VIIa is carried out in general and in particular under the conditions described for the preparation of the compound IIa from the compound VIa.

4c) The ether cleavage of IIc to IIb is normally carried out in an inert solvent at from 0° C. to 130° C., preferably 60° C. to 100° C. in the presence of an acid.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, nitriles such as acetonitrile and propionitrile, alcohols such as methanol, ethanol, n-propanol, isopropanol, n-butanol and tert-butanol, and also dimethyl sulfoxide and dimethylformamide, especially preferably methylene chloride. Mixtures of these can also be used.

Acids and acidic catalysts which are used are inorganic acids such as hydrofluoric acid, hydrochloric acid, hydrobromic acid, sulfuric acid and perchloric acid, Lewis acids, such as boron trifluoride, aluminum trichloride, iron(III) chloride, tin(IV) chloride, titanium (IV) chloride and zinc(II) chloride, and also organic acids such as formic acid, acetic acid, propionic acid, oxalic acid, citric acid and trifluoroacetic acid. In general, the acids are employed in catalytic amounts, but they can also be used in equimolar amounts, in an excess or, if appropriate, as the solvent.

Moreover, the intermediates of the formula IVa can be obtained by reacting an ether of the formula Xa either a) with an activated carboxylic acid of the formula VIIb in an inert solvent in the presence of an organometallic base, or b) with an organotin compound of the formula XI in an inert solvent.

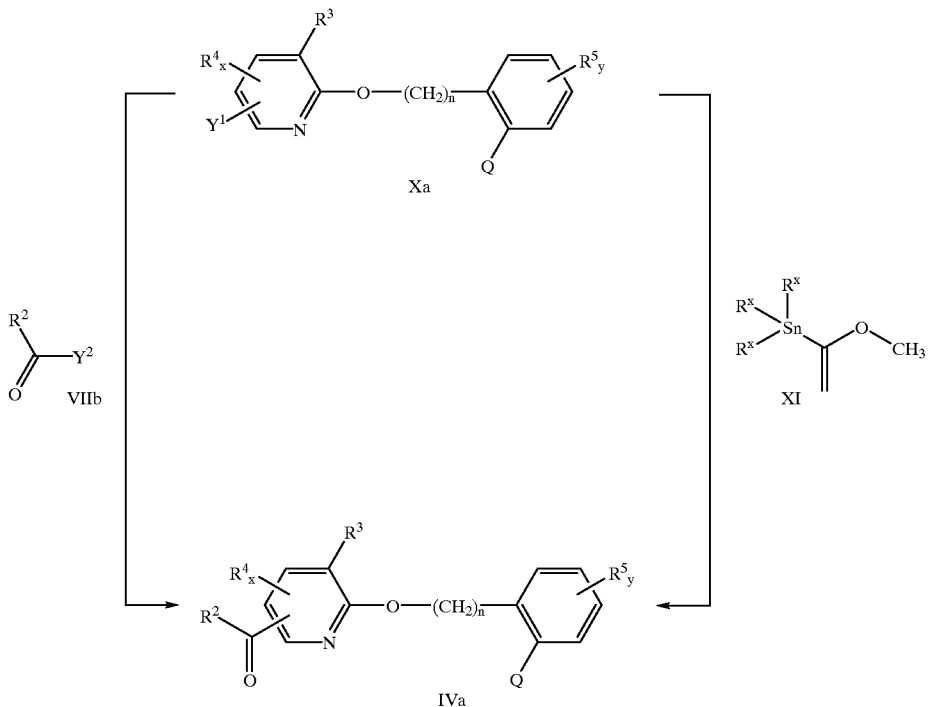

$Y^1$ in formula Xa is a halogen atom, such as fluorine, chlorine, bromine and iodine, in particular bromine and iodine.

$Y^2$ in formula VIIb is a halogen atom, such as fluorine, chlorine, bromine and iodine, in particular chlorine.

The radicals $R^x$ in formula XI are independent of one another and are alkyl.

5a) The reaction of the ether Xa with the activated carboxylic acid VIIb is carried out in general and in particular under the conditions described for the preparation of the compounds IIa from the compounds VIa.

5b) The reaction of the ether Xa with the organotin compound XI is normally carried out in an inert solvent at from −70° C. to 40° C., preferably −70° C. to 0° C., in the presence of a catalyst such as $Pd[P(C_6H_5)_3]_3$ and $PdCl_2$.
Suitable solvents are aliphatic hydrocarbons such as pentane, hexane, cyclohexane and petroleum ether, aromatic hydrocarbons such as toluene, o-, m- and p-xylene, ethers such as diethyl ether, diisopropyl ether, tert-butyl methyl ether, dioxane, anisole and tetrahydrofuran, nitriles such as acetonitrile and propionitrile, and also dimethyl sulfoxide and dimethylformamide, especially preferably tetrahydrofuran and diethyl ether. Mixtures of these can also be used.

In general, the starting materials are reacted with each other in equimolar amounts. To obtain higher yields, it may be advantageous to employ the organotin compound XI in an excess based on the ether Xa.

In the preparation of the compound I according to the invention, it is generally irrelevant whether the starting materials and intermediates which contain the phenyl or benzyl moiety (formulae III, IV and X) and, in the case of the ethers of the formula (I), already contain the group Q or whether this position is occupied by a group which can be converted into Q following the processes described in the literature cited at the outset. In principle, the group Q can be synthesized during any of the abovementioned stages (formulae III, IV, X and I).

In the new intermediates of the general formula II

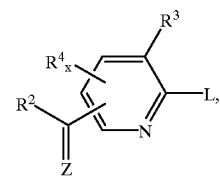

the substituent $R^2$, $R^3$ and $R^4$ and the index x have the meanings given at the outset and L and Z are the following groups:
L is hydroxyl or a nucleophilically exchangeable leaving group;
Z is oxygen or a group $NOR^1$, $R^1$ having the meanings given at the outset.

In the novel intermediates of the general formula X

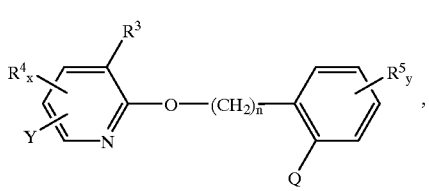

the substituent Q, $R^3$, $R^4$ and $R^5$ and the indices n, x and y have the abovementioned meanings and Y is one of the following groups: halogen or $CO—R^2$, $R^2$ having the meanings given at the outset.

The reaction mixtures are worked up in the customary manner, eg. by mixing with water, phase separation and, if desired, chromatographic purification of the crude products. In some cases, the intermediates and end products are obtained in the form of colorless or pale brown viscous oils which are purified or freed from volatile components under reduced pressure and at moderately elevated temperatures. If the intermediates and end products are obtained as solids, they can also be purified by recrystallization or digestion.

Due to their C=C and C=N double bonds, the compounds I can be obtained from their preparation as E/Z isomer mixtures which can be separated into the individual compounds in the customary manner, for example by crystallization or chromatography.

If isomer mixtures are obtained from the synthesis, however, it is generally not absolutely necessary to separate the mixtures since in some cases the individual isomers can be converted into each other during formulation for use, or upon use (eg. when exposed to light, acids or bases). Similar conversions can also take place after use, for example in the treatment of plants in the treated plant or in the harmful fungus or animal pest to be controlled.

In relation to the C=NOR$^1$ double bond, the E isomers of the compounds I are preferred with a view to their activity (configuration based on the R$^2$ group relative to the OR$^1$ group).

In the definitions of the symbols given in the above formulae, collective terms were used which generally represent the following substituent:

Halogen: fluorine, chlorine, bromine and iodine;

Alkyl: saturated straight-chain or branched hydrocarbon radicals having 1 to 4, 6, 8 or 10 carbon atoms, eg. $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Haloalkyl: straight-chain or branched alkyl groups having 1 to 10 carbon atoms (as mentioned above), it being possible for some or all of the hydrogen atoms in these groups to be replaced by halogen atoms as mentioned above, eg. $C_1$–$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkoxy: straight-chain or branched alkyl groups having 1 to 10 carbon atoms (as mentioned above) which are linked to the skeleton via an oxygen atom (—O—);

Haloalkoxy: straight-chain or branched haloalkyl groups having 1 to 10 carbon atoms (as mentioned above), which are linked to the skeleton via an oxygen atom (—O—);

Alkylthio: straight-chain or branched alkyl groups having 1 to 10 or 1 to 4 carbon atoms (as mentioned above), which are linked to the skeleton via a sulfur atom (—S—);

Alkylamino: a straight-chain or branched alkyl group having 1 to 10 carbon atoms (as mentioned above), which are linked to the skeleton via an amino group (—NH—);

Dialkylamino: two straight-chain or branched alkyl groups, independent of each other, having in each case 1 to 10 carbon atoms (as mentioned above) which are linked to the skeleton via a nitrogen atom;

Alkylcarbonyl: a straight-chain or branched alkyl group having 1 to 10 carbon atoms (as mentioned above) which is linked to the skeleton via a carbonyl group (—CO—);

Alkoxycarbonyl: an alkoxy group having 1 to 10 carbon atoms (as mentioned above) which is linked to the skeleton via a carbonyl group (—CO—);

Alkylthiocarbonyl: an alkylthio group having 1 to 10 carbon atoms (as mentioned above) which is linked to the skeleton via a carbonyl group (—CO—);

Alkylaminocarbonyl: an alkylamino group having 1 to 10 carbon atoms (as mentioned above) which is linked to the skeleton via a carbonyl group (—CO—);

Dialkylaminocarbonyl: a dialkylamino group (as mentioned above) which is linked to the skeleton via a carbonyl group (—CO—);

Alkylcarbonyloxy: a straight-chain or branched alkyl group having 1 to 10 carbon atoms (as mentioned above) which is linked to the skeleton via a carbonyloxy group (—CO$_2$—);

Alkylcarbonylthio: a straight-chain or branched alkyl group having 1 to 10 carbon atoms (as mentioned above) which is linked to the skeleton via a carbonylthio group (—COS—);

Alkylcarbonylamino: a straight-chain or branched alkyl group having 1 to 10 carbon atoms (as mentioned above) which is linked to the skeleton via a carbonylamino group (—CONH—);

Alkylsulfonyl: a straight-chain or branched alkyl group having 1 to 10 carbon atoms (as mentioned above) which is linked to the skeleton via a sulfonyl group (—SO$_2$—);

Alkoxysulfonyl: an alkoxy group having 1 to 10 carbon atoms (as mentioned above) which is linked to the skeleton via a sulfonyl group (—SO$_2$—);

Alkylthiosulfonyl: an alkylthio group having 1 to 10 carbon atoms (as mentioned above) which is linked to the skeleton via a sulfonyl group (—SO$_2$—);

Alkylaminosulfonyl: an alkylamino group having 1 to 10 carbon atoms (as mentioned above) which is linked to the skeleton via a sulfonyl group (—SO$_2$—);

Dialkylaminosulfonyl: a dialkylamino group (as mentioned above) which is linked to the skeleton via a sulfonyl group (—SO$_2$—);

Alkenyl: unsaturated straight-chain or branched hydrocarbon radicals having 2 to 4, 6, 8 or 10 carbon atoms and a double bond in any position, eg. $C_2$–$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Haloalkenyl: unsaturated straight-chain or branched hydrocarbon radicals having 2 to 10 carbon atoms and a double bond in any position (as mentioned above), it being possible for some or all of the hydrogen atoms in these-groups to be replaced by halogen atoms as mentioned above, in particular fluorine, chlorine and bromine;

Alkenyloxy: unsaturated straight-chain or branched hydrocarbon radicals having 3 to 10 carbon atoms and a double bond in any position which is not adjacent to the hetero atom (as mentioned above) which are linked to the-skeleton via an oxygen atom (—O—);

Haloalkenyloxy: unsaturated straight-chain or branched alkenyloxy groups having 3 to 10 carbon atoms (as mentioned above), it being possible for some or all of the hydrogen atoms in these groups to be replaced by halogen atoms as mentioned above, in particular fluorine, chlorine and bromine;

Alkenylthio: unsaturated straight-chain or branched hydrocarbon radicals having 3 to 10 carbon atoms and a double bond in any position which is not adjacent to the hetero atom (as mentioned above) which are linked to the skeleton via a sulfur atom (—S—);

Alkenylamino: unsaturated straight-chain or branched hydrocarbon radicals having 3 to 10 carbon atoms and a double bond in any position which is not adjacent to the hetero atom (as mentioned above) which are linked to the skeleton via an amino group (—NH—);

Alkenylcarbonyl: unsaturated straight-chain or branched hydrocarbon radicals having 2 to 10 carbon atoms and a double bond in any position (as mentioned above) which are linked to the skeleton via a carbonyl group (—CO—);

Alkenyloxycarbonyl: straight-chain or branched alkenyloxy groups having 3 to 10 carbon atoms (as mentioned above) which are linked to the skeleton via a carbonyl group (—CO—);

Alkenylthiocarbonyl: straight-chain or branched alkenylthio groups having 3 to 10 carbon atoms (as mentioned above) which are linked to the skeleton via a carbonyl group (—CO—);

Alkenylaminocarbonyl: straight-chain or branched alkenylamino groups having 3 to 10 carbon atoms (as mentioned above) which are linked to the skeleton via a carbonyl group (—CO—);

Alkenylcarbonyloxy: unsaturated straight-chain or branched hydrocarbon radicals having 2 to 10 carbon atoms and a double bond in any position (as mentioned above) which are linked to the skeleton via a carbonyloxy group (—CO$_2$—);

Alkenylcarbonylthio: unsaturated straight-chain or branched hydrocarbon radicals having 2 to 10 carbon atoms and a double bond in any position (as mentioned above) which are linked to the skeleton via a carbonylthio group (—COS—);

Alkenylcarbonylamino: unsaturated straight-chain or branched hydrocarbon radicals having 2 to 10 carbon atoms and a double bond in any position (as mentioned above) which are linked to the skeleton via a carbonylamino group (—CONH—);

Alkenylsulfonyl: unsaturated straight-chain or branched hydrocarbon radicals having 2 to 10 carbon atoms and a double bond in any position (as mentioned above) which are linked to the skeleton via a sulfonyl group (—SO$_2$—);

Alkenyloxysulfonyl: a straight-chain or branched alkenyloxy group having 3 to 10 carbon atoms (as mentioned above) which is linked to the skeleton via a sulfonyl group (—SO$_2$—);

Alkenylthiosulfonyl: a straight-chain or branched alkenylthio group having 3 to 10 carbon atoms (as mentioned above) which is linked to the skeleton via a sulfonyl group (—SO$_2$—);

Alkenylaminosulfonyl: a straight-chain or branched alkenylamino group having 3 to 10 carbon atoms (as mentioned above) which is linked to the skeleton via a sulfonyl group (—SO$_2$—);

Alkynyl: straight-chain or branched hydrocarbon groups having 2 to 4, 6, 8 or 10 carbon atoms and a triple bond in any position, eg. $C_2$–$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

Haloalkynyl: unsaturated straight-chain or branched hydrocarbon radicals having 2 to 10 carbon atoms and a triple bond in any position (as mentioned above), it being possible for some or all of the hydrogen atoms in these groups to be replaced by halogen atoms as mentioned above, in particular fluorine, chlorine and bromine;

Alkynyloxy: unsaturated straight-chain or branched hydrocarbon radicals having 3 to 10 carbon atoms and a triple bond in any position which is not adjacent to the hetero atom (as mentioned above) which are linked to the skeleton via an oxygen atom (—O—);

Haloalkynyloxy: unsaturated straight-chain or branched alkynyloxy groups having 3 to 10 carbon atoms (as mentioned above), it being possible for some or all of the hydrogen atoms in these groups to be replaced by halogen atoms as mentioned above, in particular fluorine, chlorine and bromine;

Alkynylthio: unsaturated straight-chain or branched hydrocarbon radicals having 3 to 10 carbon atoms and a triple bond in any position which is not adjacent to the hetero atom (as mentioned above) which are linked to the skeleton via a sulfur atom (—S—);

Alkynylamino: unsaturated straight-chain or branched hydrocarbon radicals having 3 to 10 carbon atoms and a triple bond in any position which is not adjacent to the hetero atom (as mentioned above) which are linked to the skeleton via an amino group (—NH—);

Alkynylcarbonyl: unsaturated straight-chain or branched hydrocarbon radicals having 2 to 10 carbon atoms and a triple bond in any position (as mentioned above) which are linked to the skeleton via a carbonyl group (—CO—);

Alkynyloxycarbonyl: straight-chain or branched alkynyloxy groups having 3 to 10 carbon atoms (as mentioned above) which are linked to the skeleton via a carbonyl group (—CO—);

Alkynylthiocarbonyl: straight-chain or branched alkynylthio groups having 3 to 10 carbon atoms (as mentioned above) which are linked to the skeleton via a carbonyl group (—CO—);

Alkynylaminocarbonyl: straight-chain or branched alkynylamino groups having 3 to 10 carbon atoms (as mentioned above) which are linked to the skeleton via a carbonyl group (—CO—);

Alkynylcarbonyloxy: unsaturated straight-chain or branched hydrocarbon radicals having 2 to 10 carbon atoms and a triple bond in any position (as mentioned above) which are linked to the skeleton via a carbonyloxy group (—CO$_2$—);

Alkynylcarbonylthio: unsaturated straight-chain or branched hydrocarbon radicals having 2 to 10 carbon atoms and a triple bond in any position (as mentioned above) which are linked to the skeleton via a carbonylthio group (—COS—);

Alkynylcarbonylamino: unsaturated straight-chain or branched hydrocarbon radicals having 2 to 10 carbon atoms and a triple bond in any position (as mentioned above) which are linked to the skeleton via a carbonylamino group (—CONH—);

Alkynylsulfonyl: unsaturated straight-chain or branched hydrocarbon radicals having 2 to 10 carbon atoms and a triple bond in any position (as mentioned above) which are linked to the skeleton via a sulfonyl group (—SO$_2$—);

Alkynyloxysulfonyl: a straight-chain or branched alkynyloxy group having 3 to 10 carbon atoms (as mentioned above) which is linked to the skeleton via a sulfonyl group (—SO$_2$—);

Alkynylthiosulfonyl: a straight-chain or branched alkynylthio group having 3 to 10 carbon atoms (as mentioned above) which is linked to the skeleton via a sulfonyl group (—SO$_2$—);

Alkynylaminosulfonyl: a straight-chain or branched alkynylamino group having 3 to 10 carbon atoms (as mentioned above) which is linked to the skeleton via a sulfonyl group (—SO$_2$—);

Cycloalkyl: monocyclic saturated hydrocarbon groups having 3 to 6, 8, 10 or 12 carbon ring members, eg. $C_3$–$C_8$-cycloalkyl, such as cyclopropyl, cyclobutyl, cyclopentyl, cyclohexyl, cycloheptyl and cyclooctyl;

Cycloalkoxy: monocyclic saturated hydrocarbon groups having 3 to 12 carbon ring members (as mentioned above) which are linked to the skeleton via an oxygen atom (—O—);

Cycloalkylthio: monocyclic saturated hydrocarbon groups having 3 to 12 carbon ring members (as mentioned above) which are linked to the skeleton via a sulfur atom (—S—);

Cycloalkylamino: monocyclic saturated hydrocarbon groups having 3 to 12 carbon ring members (as mentioned above) which are linked to the skeleton via an amino group (—NH—);

Cycloalkylcarbonyl: monocyclic saturated hydrocarbon groups having 3 to 12 carbon ring members (as mentioned above) which are linked to the skeleton via a carbonyl group (—CO—);

Cycloalkoxycarbonyl: a monocyclic cycloalkoxy group having 3 to 12 carbon ring members (as mentioned above) which is linked to the skeleton via a carbonyl group (—CO—);

Cycloalkylthiocarbonyl: a monocyclic cycloalkylthio-group having 3 to 12 carbon ring members (as mentioned above) which is linked to the skeleton via a carbonyl group (—CO—);

Cycloalkylaminocarbonyl: a monocyclic cycloalkylamino group having 3 to 12 carbon ring members (as mentioned above) which is linked to the skeleton via a carbonyl group (—CO—);

Cycloalkylcarbonyloxy: monocyclic saturated hydrocarbon groups having 3 to 12 carbon ring members (as mentioned above) which are linked to the skeleton via a carbonyloxy group (—CO$_2$—);

Cycloalkylcarbonylthio: monocyclic saturated hydrocarbon groups having 3 to 12 carbon ring members (as mentioned above) which are linked to the skeleton via a carbonylthio group (—COS—);

Cycloalkylcarbonylamino: monocyclic saturated hydrocarbon groups having 3 to 12 carbon ring members (as mentioned above) which are linked to the skeleton via a carbonylamino group (—CONH—);

Cycloalkylsulfonyl: monocyclic saturated hydrocarbon groups having 3 to 12 carbon ring members (as mentioned above) which are linked to the skeleton via a sulfonyl group (—SO$_2$—);

Cycloalkoxysulfonyl: a monocyclic cycloalkoxy group having 3 to 12 carbon ring members (as mentioned above) which is linked to the skeleton via a sulfonyl group (—SO$_2$—);

Cycloalkylthiosulfonyl: a monocyclic cycloalkylthio group having 3 to 12 carbon ring members (as mentioned above) which is linked to the skeleton via a sulfonyl group (—SO$_2$—);

Cycloalkylaminosulfonyl: a monocyclic cycloalkylamino group having 3 to 12 carbon ring members (as mentioned above) which is linked to the skeleton via a sulfonyl group (—SO$_2$—);

saturated or partially unsaturated cyclic radical which, besides carbon atoms, may contain, as ring members, hetero atoms from the group consisting of oxygen, sulfur or nitrogen: cycloalkyl having 3 to 12 carbon ring members as-mentioned above or 5- or 6-membered heterocycles (heterocyclyl) containing, besides carbon ring members, one to three nitrogen atoms and/or one oxygen or sulfur atom or one or two oxygen and/or sulfur atoms, eg. 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl and 1,2,4-tetrahydrotriazin-3-yl;

Heterocyclyloxy: a 5- or 6-membered heterocycle (as mentioned above) which is linked to the skeleton via an oxygen atom (—O—);

Heterocyclylthio: a 5- or 6-membered heterocycle (as mentioned above) which is linked to the skeleton via a sulfur atom (—S—);

Heterocyclylamino: a 5- or 6-membered heterocycle (as mentioned above) which is linked to he skeleton via an amino group (—NH—);

Heterocyclylcarbonyl: a 5- or 6-membered heterocycle (as mentioned above) which is linked to the skeleton via a carbonyl group (—CO—);

Heterocyclyloxycarbonyl: a heterocyclyloxy group (as mentioned above) which is linked to the skeleton via a carbonyl group (—CO—);

Heterocyclylthiocarbonyl: a heterocyclylthio group (as mentioned above) which is linked to the skeleton via a carbonyl group (—CO—);

Heterocyclylaminocarbonyl: a 5- or 6-membered heterocycle (as mentioned above) which is linked to the skeleton via an aminocarbonyl group (—NHCO—);

Heterocyclylcarbonyloxy: a 5- or 6-membered heterocycle (as mentioned above) which is linked to the skeleton via a carbonyloxy group (—CO$_2$—);

Heterocyclylcarbonylthio: a 5- or 6-membered heterocycle (as mentioned above) which is linked to the skeleton via a carbonylthio group (—COS—);

Heterocyclylcarbonylamino: a 5- or 6-membered heterocycle (as mentioned above) which is linked to the skeleton via a carbonylamino group (—CONH—);

Heterocyclylsulfonyl: a 5- or 6-membered heterocycle (as mentioned above) which is linked to the skeleton via a sulfonyl group (—SO$_2$—);

Aryloxysulfonyl: a heterocyclyloxy group (as mentioned above) which is linked to the skeleton via a sulfonyl group (—SO$_2$—);

Heterocyclylthiosulfonyl: a heterocyclylthio group (as mentioned above) which is linked to the skeleton via a sulfonyl group (—SO$_2$—);

Heterocyclylaminosulfonyl: a heterocyclylamino group (as mentioned above) which is linked to the skeleton via the skeleton via a sulfonyl group (—SO$_2$—);

Aryl: a mono- to trinuclear aromatic ring system containing 6 to 14 carbon ring members, eg. phenyl, naphthyl and anthracenyl;

Aryloxy: a mono- to trinuclear aromatic ring system (as mentioned above) which is linked to the skeleton via the skeleton via an oxygen atom (—O—);

Arylthio: a mono- to trinuclear aromatic ring system (as mentioned above) which is linked to the skeleton via the skeleton via a sulfur atom (—S—);

Arylamino: a mono- to trinuclear aromatic ring system (as mentioned above) which is linked to the skeleton via an amino group (—NH—);

Arylcarbonyl: a mono- to trinuclear aromatic ring system (as mentioned above) which is linked to the skeleton via a carbonyl group (—CO—);

Aryloxycarbonyl: a mono- to trinuclear aryloxy group (as mentioned above) which is linked to the skeleton via a carbonyl group (—CO—);

Arylthiocarbonyl: a mono- to trinuclear arylthio group (as mentioned above) which is linked to the skeleton via a carbonyl group (—CO—);

Arylaminocarbonyl: a mono- to trinuclear arylamino group (as mentioned above) which is linked to the skeleton via a carbonyl group (—CO—);

Arylcarbonyloxy: a mono- to trinuclear aromatic ring system (as mentioned above) which is linked to the skeleton via a carbonyloxy group (—CO$_2$—);

Arylcarbonylthio: a mono- to trinuclear aromatic ring system (as mentioned above) which is linked to the skeleton via a carbonylthio group (—COS—);

Arylcarbonylamino: a mono- to trinuclear aromatic ring system (as mentioned above) which is linked to the skeleton via a carbonylamino group (—CONH—);

Arylsulfonyl: a mono- to trinuclear aromatic ring system (as mentioned above) which is linked to the skeleton via a sulfonyl group (—SO$_2$—);

Aryloxysulfonyl: a mono- to trinuclear aryloxy group (as mentioned above) which is linked to the skeleton via a sulflonyl group (—SO$_2$—);

Arylthiosulfonyl: a mono- to trinuclear arylthio group (as mentioned above) which is linked to the skeleton via a sulfonyl group (—SO$_2$—);

Arylaminosulfonyl: a mono- to trinuclear arylamino group (as mentioned above) which is linked to the skeleton via a sulfonyl group (—SO$_2$—);

aromatic ring system which, besides carbon ring members, may contain hetero atoms from the group consisting of oxygen, sulfur, and nitrogen: aryl as mentioned above or mono- or binuclear hetaryl, eg.

5-membered hetaryl containing one to four nitrogen atoms or one to three nitrogen atoms and one sulfur or oxygen atom:
- 5-membered hetaryl groups, which, besides carbon atoms, may contain one to four nitrogen atoms or one to three nitrogen atoms and one sulfur or oxygen atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

benzo-fused 5-membered hetaryl containing one to three nitrogen atoms or one nitrogen atom and one oxygen or sulfur atom:
- 5-membered hetaryl groups which, besides carbon atoms, can contain one to four nitrogen atoms or one to three nitrogen atoms and one sulfur or oxygen atom as ring members and in which two adjacent carbon ring members or one nitrogen and one adjacent carbon ring member can be bridged via a buta-1,3-diene-1,4-diyl group;

5-membered hetaryl. linked via nitrogen and containing one to four nitrogen atoms, or benza-fused 5-membered hetaryl, linked via nitrogen and containing one to three nitrogen atoms:
- 5-membered hetaryl ring groups which, besides carbon atoms, can contain one to four nitrogen atoms, or one to three nitrogen atoms, respectively, as ring members and in which two adjacent carbon ring members or one nitrogen and one adjacent carbon ring member can be bridged via a buta-1,3-diene-1,4-diyl group, these rings being linked to the skeleton via one of the nitrogen ring members;

6-membered hetaryl containing one to three, or one to four. nitrogen atoms, respectively: 6-membered hetaryl ring groups which, besides carbon atoms, can contain one to three, or one to four, nitrogen atoms, respectively, as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl;

Hetaryloxy: a mono- to trinuclear heteroaromatic ring system (as mentioned above) which is linked to the skeleton via an oxygen atom (—O—);

Hetarylthio: a mono- to trinuclear heteroaromatic ring system (as mentioned above) which is linked to the skeleton via a sulfur atom (—S—);

Hetarylamino: a mono- to trinuclear heteroaromatic ring system (as mentioned above) which is linked to the skeleton via an amino group (—NH—);

Hetarylcarbonyl: a mono- to trinuclear heteroaromatic ring system (as mentioned above) which is linked to the skeleton via a carbonyl group (—CO—);

Hetaryloxycarbonyl: an mono- to trinuclear hetaryloxy group (as mentioned above) which is linked to the skeleton via a carbonyl group (—CO—);

Hetarylthiocarbonyl: an mono- to trinuclear hetarylthio group (as mentioned above) which is linked to the skeleton via a carbonyl group (—CO—);

Hetarylaminocarbonyl: an mono- to trinuclear hetarylamino group (as mentioned above) which is linked to the skeleton via a carbonyl group (—CO—);

Hetarylcarbonyloxy: a mono- to trinuclear heteroaromatic ring system (as mentioned above) which is linked to the skeleton via a carbonyloxy group (—CO$_2$—);

Hetarylcarbonylthio: a mono- to trinuclear heteroaromatic ring system (as mentioned above) which is linked to the skeleton via a carbonylthio group (—COS—);

Hetarylcarbonylamino: a mono- to trinuclear heteroaromatic ring system (as mentioned above) which is linked to the skeleton via a carbonylamino group (—CONH—);

Hetarylsulfonyl: a mono- to trinuclear heteroaromatic ring system (as mentioned above) which is linked to the skeleton via a sulfonyl group (—SO$_2$—);

Hetaryloxysulfonyl: an mono- to trinuclear hetaryloxy group (as mentioned above) which is linked to the skeleton via a sulfonyl group (—SO$_2$—);

Hetarylthiosulfonyl: an mono- to trinuclear hetarylthio group (as mentioned above) which is linked to the skeleton via a sulfonyl group (—SO$_2$—);

Hetarylaminosulfonyl: an mono- to trinuclear hetarylamino group (as mentioned above) which is linked to the skeleton via a sulfonyl group (—SO$_2$—);

Alkylene: divalent unbranched chains of 1 to 5 CH$_2$— groups, eg. CH$_2$, CH$_2$CH$_2$, CH$_2$CH$_2$CH$_2$, CH$_2$CH$_2$CH$_2$CH$_2$ and CH$_2$CH$_2$CH$_2$CH$_2$CH$_2$;

Oxyalkylene: divalent unbranched chains of 2 to 4 CH$_2$— groups, one valency being linked to the skeleton via an oxygen atom, eg. OCH$_2$CH$_2$, OCH$_2$CH$_2$CH$_2$ and OCH$_2$CH$_2$CH$_2$CH$_2$;

Oxyalkyleneoxy: divalent unbranched chains of 1 to 3 CH$_2$— groups, both valencies being linked to the skeleton via an oxygen atom eg. OCH$_2$O, OCH$_2$CH$_2$O and OCH$_2$CH$_2$CH$_2$O;

Alkenylene: divalent unbranched chains of 1 to 3 CH$_2$— groups and one CH=CH— group in any position, eg. CH=CHCH$_2$, CH$_2$CH=CHCH$_2$, CH=CHCH$_2$CH$_2$, CH$_2$CH=CHCH$_2$CH$_2$ and CH=CHCH$_2$CH$_2$CH$_2$;

Oxyalkenylene: divalent unbranched chains of 0 to 2 CH$_2$— groups and one CH=CH— group in any position, one valency being linked to the skeleton via an oxygen atom , eg. OCH=CH, OCH=CHCH$_2$, OCH$_2$CH=CH, OCH$_2$CH=CHCH$_2$, OCH=CHCH$_2$CH$_2$ and OCH$_2$CH$_2$—CH=CH;

Oxyalkenyleneoxy: divalent unbranched chains of 0 to 2 CH$_2$— groups and one CH=CH— group in any position, both valencies being linked to the skeleton via an oxygen atom , eg. OCH=CHO, OCH=CHCH$_2$O, OCH$_2$CH=CHCH$_2$O and OCH=CHCH$_2$CH$_2$O;

Organic radical: unsubstituted or substituted alkyl, alkenyl, alkynyl, cycloalkyl, heterocyclyl, aryl or hetaryl.

The term "unsubstituted or substituted" when relating to alkyl, alkenyl and alkynyl groups is intended to express that these groups can be partially or fully halogenated [ie. some or all of the hydrogen atoms of these groups can be replaced by identical or different halogen atoms as mentioned above (preferably fluorine, chlorine or bromine)] and/or can have attached to them one to three (preferably one) of the following radicals:

cyano, nitro, hydroxyl, amino, formyl, carboxyl, aminocarbonyl, alkoxy, haloalkoxy, alkylthio, haloalkylthio, alkylamino, dialkylamino, alkylcarbonyl, alkoxycarbonyl, alkylcarbonyloxy, alkylaminocarbonyl, dialkylaminocarbonyl, alkylcarbonylamino, alkoxycarbonylamino, alkylcarbonyl-N-alkylamino and alkoxycarbonyl-N-alkylamino, the alkyl groups in these radicals preferably containing 1 to 6 carbon atoms, in particular containing 1 to 4 carbon atoms;

cycloalkyl, cycloalkoxy, cycloalkylthio, cycloalkylamino, cycloalkyl-N-alkylamino, heterocyclyl, heterocyclyloxy, heterocyclylthio, heterocyclylamino or heterocyclyl-N-alkylamino, unsubstituted or substituted by customary groups, the cyclic systems containing 3 to 12 ring members, preferably 2 to 8 ring members, in particular 3 to 6 ring members, and the alkyl groups in these radicals preferably containing 1 to 6 carbon atoms, in particular 1 to 4 carbon atoms;

aryl, aryloxy, arylthio, arylamino, aryl-N-alkylamino, arylalkoxy, arylalkylthio, arylalkylamino, arylalkyl-N-alkylamino, hetaryl, hetaryloxy, hetarylthio, hetarylamino, hetaryl-N-alkylamino, hetarylalkoxy, hetarylalkylthio, hetarylalkylamino and hetarylalkyl-N-alkylamino, unsubstituted or substituted by customary groups, the aryl radicals preferably containing 6 to 10 ring members, in particular 6 ring members (phenyl), the hetaryl radicals containing in particular 5 or 6 ring members and the alkyl groups in these radicals containing preferably 1 to 6 carbon atoms, in particular 1 to 4 carbon atoms.

The term "unsubstituted or substituted" when relating to the cyclic (saturated, unsaturated or aromatic) groups is intended to express that these groups can be partially or fully halogenated [ie. some or all of the hydrogen atoms in these groups can be replaced by identical or different halogen atoms as mentioned above (preferably fluorine, chlorine or bromine, in particular fluorine or chlorine)] and/or can have attached to them one to four (in particular one to three) of the following radicals:

cyano, nitro, hydroxyl, amino, carboxyl, aminocarbonyl, alkyl, haloalkyl, alkenyl, haloalkenyl, alkenyloxy, haloalkenyloxy, alkynyl, haloalkynyl, alkynyloxy, haloalkynyloxy, alkoxy, haloalkoxy, alkylthio, haloalkylthio, alkylamino, dialkylamino, alkylcarbonyl, alkoxycarbonyl, alkylcarbonyloxy, alkylaminocarbonyl, dialkylaminocarbonyl, alkylcarbonylamino, alkoxycarbonylamino, alkylcarbonyl-N-alkylamino and alkoxycarbonyl-N-alkylamino, the alkyl groups in these radicals preferably containing 1 to 6 carbon atoms, in particular 1 to 4 carbon atoms, and the abovementioned alkenyl or alkynyl groups in these radicals containing 2 to 8, preferably 2 to 6, in particular 2 to 4, carbon atoms;

and/or one to three (in particular one) of the following radicals:

cycloalkyl, cycloalkoxy, cycloalkylthio, cycloalkylamino, cycloalkyl-N-alkylamino, heterocyclyl, heterocyclyloxy, heterocyclylthio, heterocyclylamino or heterocyclyl-N-alkylamino, unsubstituted or substituted by customary groups, the cyclic systems containing 3 to 12 ring members, preferably 3 to 8 ring members, in particular 3 to 6 ring members, and the alkyl groups in these radicals preferably containing 1 to 6 carbon atoms, in particular 1 to 4 carbon atoms;

aryl, aryloxy, arylthio, arylamino, aryl-N-alkylamino, arylalkoxy, arylalkylthio, arylalkylamino, arylalkyl-N-alkylamino, hetaryl, hetaryloxy, hetarylthio, hetarylamino, hetaryl-N-alkylamino, hetarylalkoxy, hetarylalkylthio, hetarylalkylamino and hetarylalkyl-N-alkylamino, unsubstituted or substituted by customary groups, the aryl radicals preferably containing 6 to 10 ring members, in particular 6 ring members (phenyl), the hetaryl radicals containing in particular 5 or 6 ring members and the alkyl groups in these radicals preferably containing 1 to 6 carbon atoms, in particular 1 to 4 carbon atoms;

and/or one or two (in particular one) of the following radicals:

formyl, $CR^{iii}$=$NOR^{iv}$ [where $R^{iii}$ is hydrogen, alkyl, cycloalkyl and aryl and $R^{iv}$ is alkyl, alkenyl, haloalkenyl, alkynyl and arylalkyl (the abovementioned alkyl groups preferably containing 1 to 6 carbon atoms, in particular 1 to 4 carbon atoms, the abovementioned cycloalkyl groups, alkenyl groups and alkynyl groups preferably containing-from 3 to 8, in particular 3 to 6, carbon atoms) and aryl being in particular phenyl which is unsubstituted or can be substituted by customary groups] or $NR^{v}$—CO—D—$R^{vi}$ [where $R^{v}$ is hydrogen, hydroxyl, $C_1$–$C_6$-alkyl, $C_2$–$C_6$-alkenyl, $C_2$–$C_6$-alkynyl, $C_1$–$C_6$-alkoxy, $C_2$–$C_6$-alkenyloxy, $C_2$–$C_6$-alkynyloxy, $C_1$–$C_6$-alkoxy-$C_1$–$C_6$-alkyl, $C_1$–$C_6$-alkoxy-$C_1$–$C_6$-alkoxy and $C_1$–$C_6$-alkoxycarbonyl, $R^{vi}$ is hydrogen, $C_1$–$C_6$-alkyl, $C_2$–$C_6$-alkenyl, $C_2$–$C_6$-alkynyl, $C_3$–$C_6$-cycloalkyl, $C_3$–$C_6$-cycloalkenyl, aryl, aryl-$C_1$–$C_6$-alkyl, hetaryl and hetaryl-$C_1$–$C_6$-alkyl and D being a direct linkage, oxygen or nitrogen, it being possible for the nitrogen to have attached to it one of the groups mentioned under $R^{vi}$], and/or where two adjacent C-atoms of the cyclic systems can have attached to them a $C_3$–$C_5$-alkylene, $C_3$–$C_5$-alkenylene, oxy-$C_2$–$C_4$-alkylene, oxy-$C_1$–$C_3$-alkyleneoxy, oxy-$C_2$–$C_4$-alkenylene, oxy-$C_2$–$C_4$-alkenyleneoxy or butadienediyl group, it being possible for these bridges, in turn, to be partially or fully halogenated and/or to have attached to them one to three, in particular one or two, of the following radicals:

$C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

Customary groups are to be understood as meaning, in particular, the following substituent: halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-$C_1$–$C_4$-alkylamino and $C_1$–$C_4$-alkylthio.

Especially preferred compounds I are those where Q is $C(CO_2CH_3)$=$CHCH_3$, $C(CO_2CH_3)$=$CHOCH_3$, $C(CO_2CH_3)$=$NOCH_3$, $C(CONHCH_3)$'or $N(OCH_3)$—$CO_2CH_3$.

Especially preferred compounds of the formula I are those where $R^1$ is hydrogen or one of the following groups: unsubstituted or substituted alkyl, alkenyl, alkynyl, cycloalkyl, heterocyclyl, aryl or hetaryl.

Particularly preferred compounds I are those where $R^1$ is hydrogen.

Furthermore, especially preferred compounds I are those where $R^1$ is unsubstituted or substituted $C_1$–$C_6$-alkyl.

Equally, especially preferred compounds I are those where $R^1$ is unsubstituted or substituted $C_3$–$C_6$-alkenyl.

Besides, especially preferred compounds I are those where $R^1$ is unsubstituted or substituted $C_3$–$C_6$-alkynyl.

Other particularly preferred compounds I are those where $R^1$ is $C_1$–$C_6$-haloalkyl.

Furthermore, especially preferred compounds I are those where $R^1$ is $C_3$–$C_6$-haloalkenyl.

Equally, especially preferred compounds I are those where $R^1$ is aryl-$C_1$–$C_2$-alkyl, it being possible for the aryl radical to be unsubstituted or substituted.

Especially preferred compounds I are those where $R^1$ is aryl-$C_1$–$C_2$-alkyl, it being possible for the aryl radical to be partially or fully halogenated and/or to have attached to it one to three of the following groups: $C_1$–$C_4$-alkyl, $C_1$–$C_4$-haloalkyl and $C_1$–$C_4$-alkoxy.

Besides, especially preferred compounds I are those where $R^1$ is $C_3$–$C_6$-cycloalkyl-$C_1$–$C_2$-alkyl, it being possible for the cycloalkyl radical to be unsubstituted or substituted.

Particularly preferred compounds I are those where $R^1$ is $C_3$–$C_6$-cycloalkyl-$C_1$–$C_2$-alkyl, it being possible for the cycloalkyl radical to be partially or fully halogenated and/or to have attached to it one to three $C_1$–$C_4$-alkyl groups.

Moreover, especially preferred compounds I are those where $R^1$ is hetaryl-$C_1$–$C_2$-alkyl, it being possible for the hetaryl radical to be unsubstituted or substituted.

Particularly preferred compounds I are those where $R^1$ is hetaryl-$C_1$–$C_2$-alkyl, it being possible for the hetaryl radical to be partially or fully halogenated and/or to have attached to it one to three of the following groups: $C_1$–$C_4$-alkyl, $C_1$–$C_4$-haloalkyl and $C_1$–$C_4$-alkoxy.

Furthermore, especially preferred compounds of the formula I are those where $R^2$ is hydrogen or one of the following groups: unsubstituted or substituted alkyl, alkenyl, alkynyl, cycloalkyl, heterocyclyl, aryl or hetaryl, these groups being linked to the skeleton either directly (via a carbon atom) or via an oxygen, sulfur or nitrogen atom.

Particularly preferred compounds I are those where $R^2$ is unsubstituted or substituted $C_1$–$C_6$-alkyl.

Furthermore, especially preferred compounds I are those where $R^2$ is unsubstituted or substituted $C_2$–$C_6$-alkenyl.

Equally, especially preferred compounds I are those where $R^2$ is unsubstituted or substituted $C_2$–$C_6$-alkynyl.

Besides, especially preferred compounds I are those where $R^2$ is $C_3$–$C_6$-cycloalkyl.

Other compounds I which are particularly preferred are those where $R^2$ is aryl.

Furthermore, especially preferred compounds I are those where $R^2$ is hetaryl.

Moreover, especially preferred compounds I are those where $R^3$ is hydrogen, halogen, $C_1$–$C_3$-alkyl or $C_1$–$C_2$-haloalkyl, in particular hydrogen, methyl, fluorine, chlorine, ethyl, isopropyl and trifluoromethyl.

Particularly preferred compounds I are those where $R^3$ is hydrogen. Moreover, especially preferred compounds I are those where $R^3$ is halogen, in particular fluorine, chlorine and bromine.

Equally, especially preferred compounds I are those where $R^3$ is methyl.

Besides, especially preferred compounds I are those where $R^3$ is $C_1$-haloalkyl, in particular trifluoromethyl.

Furthermore, especially preferred compounds I are those where x is 0, 1 or 2, it being possible for the radicals $R^4$ to be different if x is 2.

Particularly preferred compounds I are those where x is 0 or 1.

Furthermore, especially preferred compounds of the formula I are those where $R^4$ is cyano, nitro, halogen or one of the following groups: unsubstituted or substituted alkyl, alkenyl, alkynyl, cycloalkyl, heterocyclyl, aryl or hetaryl, these groups being linked to the skeleton directly (via a carbon atom) or via an oxygen, sulfur or nitrogen atom.

Particularly preferred compounds I are those where $R^4$ is halogen, in particular fluorine, chlorine or bromine.

Moreover, especially preferred compounds I are those where $R^4$ is $C_1$–$C_2$-alkyl.

Equally, especially preferred compounds I are those where $R^4$ is $C_1$–$C_2$-alkoxy.

Besides, especially preferred compounds I are those where $R^4$ is cyano.

Other particularly preferred compounds I are those where $R^4$ is nitro.

Moreover, especially preferred compounds I are those where y is 0, 1, 2 or 3, it being possible for the radicals $R^5$ to be different if y is 2 or 3.

Particularly preferred compounds I are those where y is 0 or 1.

Furthermore, especially preferred compounds I are those where $R^5$ is cyano, halogen, $C_1$–$C_3$-alkyl, $C_1$–$C_2$-haloalkyl or $C_1$–$C_3$-alkoxy, in particular cyano, fluorine, chlorine, methyl, ethyl, isopropyl, trifluoromethyl, methoxy or ethoxy.

Particularly preferred compounds I are those where $R^5$ is methyl.

Furthermore, especially preferred compounds I are those where $R^5$ is methoxy.

Equally, especially preferred compounds I are those where $R^5$ is fluorine.

Besides, especially preferred compounds I are those where $R^5$ is chlorine.

Other particularly preferred compounds I are those where $R^5$ is trifluoromethyl.

Furthermore, especially preferred compounds I are those where $R^5$ is $OCH_2O$.

Particularly preferred compounds I with a view to their use are those compiled in the Tables which follow. Furthermore, the groups mentioned in the Tables for one substituent are as such an especially preferred embodiment of the substituent in question, irrespective of the combination in which they are mentioned.

Table 1

Compounds of the general formula IA.1 where $R^2$ is methyl, $R^3$ is hydrogen, $R^4$ is hydrogen, $R^5_y$ is hydrogen and $R^1$ for each compound corresponds to one group of Table A.

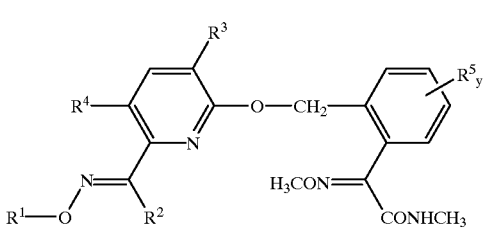

Table 2

Compounds of the general formula IA.2 where $R^2$ is methyl, $R^3$ is hydrogen, $R^4$ is hydrogen and $R^5_y$ is hydrogen and $R^1$ for each compound corresponds to one group of Table A.

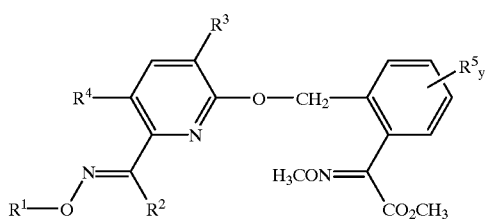

IA.2

Table 3

Compounds of the general formula IA.3 where $R^2$ is methyl, $R^3$ is hydrogen, $R^4$ is hydrogen and $R^5_y$ is hydrogen and $R^1$ for each compound corresponds to one group of Table A.

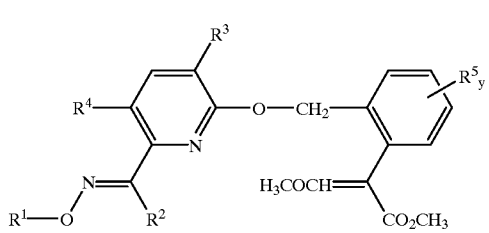

IA.3

Table 4

Compounds of the general formula IA.4 where $R^2$ is methyl, $R^3$ is hydrogen, $R^4$ is hydrogen and $R^5_y$ is hydrogen and $R^1$ for each compound corresponds to one group of Table A.

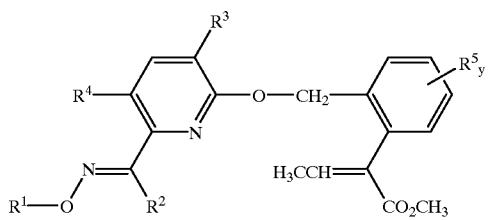

IA.4

Table 5

Compounds of the general formula IA.5 where $R^2$ is methyl, $R^3$ is hydrogen, $R^4$ is hydrogen and $R^5_y$ is hydrogen and $R^1$ for each compound corresponds to one group of Table A.

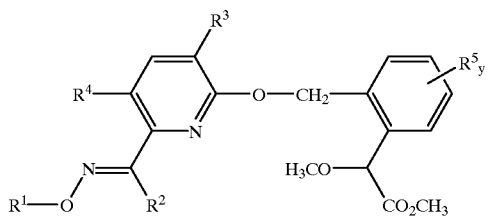

IA.5

Table 6

Compounds of the general formula IA.6 where $R^2$ is methyl, $R^3$ is hydrogen, $R^4$ is hydrogen and $R^5_y$ is hydrogen and $R^1$ for each compound corresponds to one group of Table A.

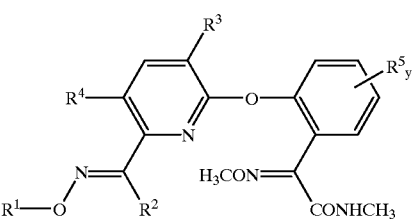

IA.6

Table 7

Compounds of the general formula IA.7 where $R^2$ is methyl, $R^3$ is hydrogen, $R^4$ is hydrogen and $R^5_y$ is hydrogen and $R^1$ for each compound corresponds to one group of Table A.

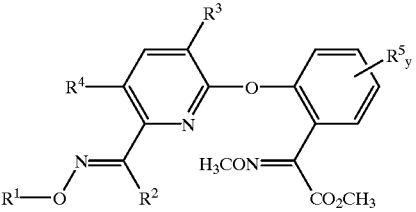

IA.7

Table 8

Compounds of the general formula IA.8 where $R^2$ is methyl, $R^3$ is hydrogen, $R^4$ is hydrogen and $R^5_y$ is hydrogen and $R^1$ for each compound corresponds to one group of Table A.

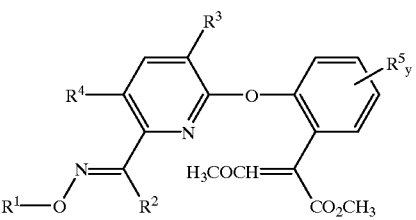

IA.8

Table 9

Compounds of the general formula IA.9 where $R^2$ is methyl, $R^3$ is hydrogen, $R^4$ is hydrogen and $R^5_y$ is hydrogen and $R^1$ for each compound corresponds to one group of Table A.

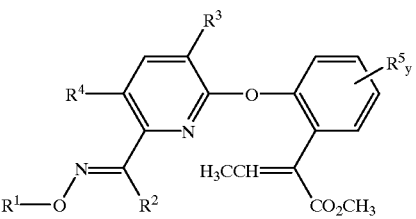

IA.9

Table 10

Compounds of the general formula IA.10 where $R^2$ is methyl, $R^3$ is hydrogen, $R^4$ is hydrogen and $R^5_y$ is hydrogen and $R^1$ for each compound corresponds to one group of Table A.

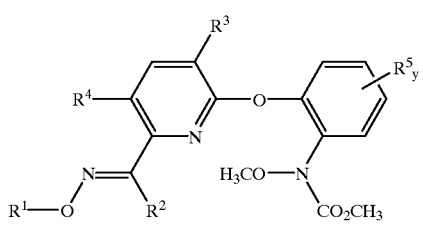
IA.10

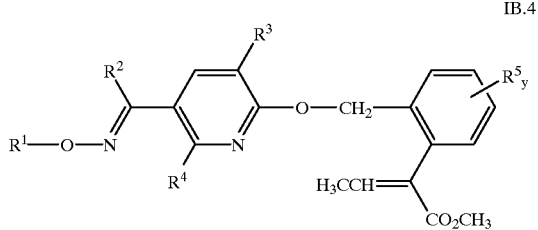
IB.4

Table 11

Compounds of the general formula IB.1 where $R^2$ is methyl, $R^3$ is hydrogen, $R^4$ is hydrogen and $R^5_y$ is hydrogen and $R^1$ for each compound corresponds to one group of Table A.

Table 15

Compounds of the general formula IB.5 where $R^2$ is methyl, $R^3$ is hydrogen, $R^4$ is hydrogen and $R^5_y$ is hydrogen and $R^1$ for each compound corresponds to one group of Table A.

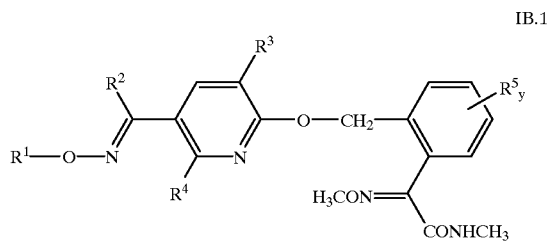
IB.1

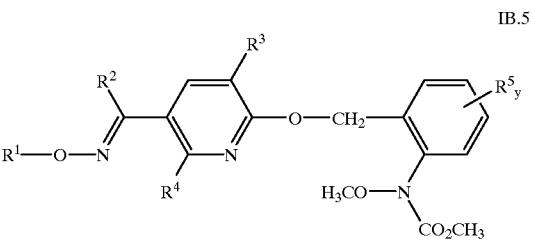
IB.5

Table 12

Compounds of the general formula IB.2 where $R^2$ is methyl, $R^3$ is hydrogen, $R^4$ is hydrogen and $R^5_y$ is hydrogen and $R^1$ for each compound corresponds to one group of Table A.

Table 16

Compounds of the general formula IB.6 where $R^2$ is methyl, $R^3$ is hydrogen., $R^4$ is hydrogen and $R^5_y$ is hydrogen and $R^1$ for each compound corresponds to one group of Table A.

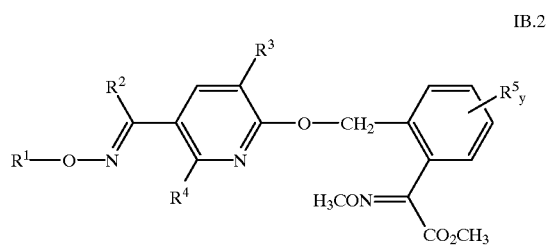
IB.2

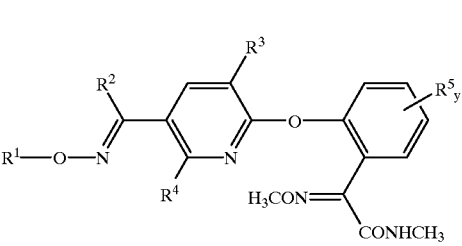
IB.6

Table 13

Compounds of the general formula IB.3 where $R^2$ is methyl, $R^3$ is hydrogen, $R^4$ is hydrogen and $R^5_y$ is hydrogen and $R^1$ for each compound corresponds to one group of Table A.

Table 17

Compounds of the general formula IB.7 where $R^2$ is methyl, $R^3$ is hydrogen, $R^4$ is hydrogen and $R^5_y$ is hydrogen and $R^1$ for each compound corresponds to one group of Table A.

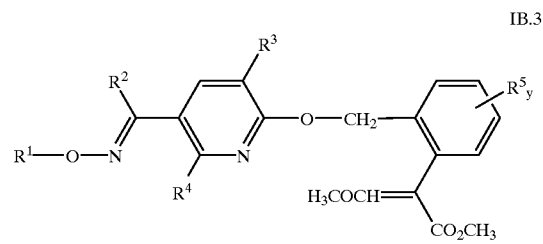
IB.3

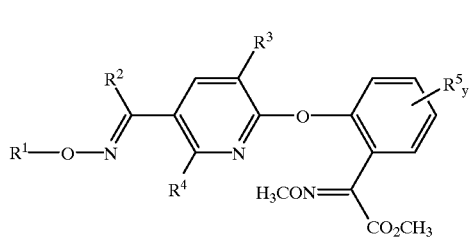
IB.7

Table 14

Compounds of the general formula IB.4 where $R^2$ is methyl, $R^3$ is hydrogen, $R^4$ is hydrogen and $R^5_y$ is hydrogen and $R^1$ for each compound corresponds to one group of Table A.

Table 18

Compounds of the general formula IB.8 where $R^2$ is methyl, $R^3$ is hydrogen, $R^4$ is hydrogen and $R^5_y$ is hydrogen and $R^1$ for each compound corresponds to one group of Table A.

IB.8

[Structure: pyridine with R²-C(=N-O-R¹) at one position, R³, R⁴ substituents, connected via O to phenyl ring with R⁵_y substituent and H₃COCH=C(CO₂CH₃) group]

Table 19
Compounds of the general formula IB.9 where R² is methyl, R³ is hydrogen, R⁴ is hydrogen and R⁵_y is hydrogen and R¹ for each compound corresponds to one group of Table A.

IB.9

[Structure similar to above]

Table 20
Compounds of the general formula IB.10 where R² is methyl, R³ is hydrogen., R⁴ is hydrogen and R⁵_y is hydrogen and R¹ for each compound corresponds to one group of Table A.

IB.10

[Structure similar to above with H₃CO—N(CO₂CH₃) group]

Table 21
Compounds of the general formula IA.1 where R² is methyl, R³ is methyl, R⁴ is hydrogen and R⁵_y is hydrogen and R¹ for each compound corresponds to one group of Table A.

Table 22
Compounds of the general formula IA.2 where R² is methyl, R³ is methyl, R⁴ is hydrogen and R⁵_y is hydrogen and R¹ for each compound corresponds to one group of Table A.

Table 23
Compounds of the general formula IA.3 where R² is methyl, R³ is methyl, R⁴ is hydrogen and R⁵_y is hydrogen and R¹ for each compound corresponds to one group of Table A.

Table 24
Compounds of the general formula IA.4 where R² is methyl, R³ is methyl, R⁴ is hydrogen and R⁵_y is hydrogen and R¹ for each compound corresponds to one group of Table A.

Table 25
Compounds of the general formula IA.5 where R² is methyl, R³ is methyl, R⁴ is hydrogen and R⁵_y is hydrogen and R¹ for each compound corresponds to one group of Table A.

Table 26
Compounds of the general formula IA.6 where R² is methyl, R³ is methyl, R⁴ is hydrogen and R⁵_y is hydrogen and R¹ for each compound corresponds to one group of Table A.

Table 27
Compounds of the general formula IA.7 where R² is methyl, R³ is methyl, R⁴ is hydrogen and R⁵_y is hydrogen and R¹ for each compound corresponds to one group of Table A.

Table 28
Compounds of the general formula IA.8 where R² is methyl, R³ is methyl, R⁴ is hydrogen and R⁵_y is hydrogen and R¹ for each compound corresponds to one group of Table A.

Table 29
Compounds of the general formula IA.9 where R² is methyl, R³ is methyl, R⁴ is hydrogen and R⁵_y is hydrogen and R¹ for each compound corresponds to one group of Table A.

Table 30
Compounds of the general formula IA.10 where R² is methyl, R³ is methyl, R⁴ is hydrogen and R⁵_y is hydrogen and R¹ for each compound corresponds to one group of Table A.

Table 31
Compounds of the general formula IB.1 where R² is methyl, R is methyl, R⁴ is hydrogen and R⁵_y is hydrogen and R¹ for each compound corresponds to one group of Table A.

Table 32
Compounds of the general formula IB.2 where R² is methyl, R³ is methyl, R⁴ is hydrogen and R⁵_y is hydrogen and R¹ for each compound corresponds to one group of Table A.

Table 33
Compounds of the general formula IB.3 where R² is methyl, R³ is methyl, R⁴ is hydrogen and R⁵_y is hydrogen and R¹ for each compound corresponds to one group of Table A.

Table 34
Compounds of the general formula IB.4 where R² is methyl, R³ is methyl, R⁴ is hydrogen and R⁵_y is hydrogen and R¹ for each compound corresponds to one group of Table A.

Table 35
Compounds of the general formula IB.5 where R² is methyl, R³ is methyl, R⁴ is hydrogen and R⁵_y is hydrogen and R¹ for each compound corresponds to one group of Table A.

Table 36
Compounds of the general formula IB.6 where R² is methyl, R³ is methyl, R⁴ is hydrogen and R⁵_y is hydrogen and R¹ for each compound corresponds to one group of Table A.

Table 37
Compounds of the general formula IB.7 where R² is methyl, R³ is methyl, R⁴ is hydrogen and R⁵_y is hydrogen and R¹ for each compound corresponds to one group of Table A.

Table 38
Compounds of the general formula IB.8 where R² is methyl, R³ is methyl, R⁴ is hydrogen and R⁵_y is hydrogen and R¹ for each compound corresponds to one group of Table A.

Table 39
Compounds of the general formula IB.9 where R² is methyl, R³ is methyl, R⁴ is hydrogen and R⁵_y is hydrogen and R¹ for each compound corresponds to one group of Table A.

Table 40
Compounds of the general formula IB.10 where $R^2$ is methyl, $R^3$ is methyl, $R^4$ is hydrogen and $R^5_y$ is hydrogen and $R^1$ for each compound corresponds to one group of Table A.

Table 41
Compounds of the general formula IA.1 where $R^2$ is methyl, $R^3$ is chlorine, $R^4$ is hydrogen and $R^5_y$ is hydrogen and $R^1$ for each compound corresponds to one group of Table A.

Table 42
Compounds of the general formula IA.2 where $R^2$ is methyl, $R^3$ is chlorine, $R^4$ is hydrogen and $R^5_y$ is hydrogen and $R^1$ for each compound corresponds to one group of Table A.

Table 43
Compounds of the general formula IA.3 where $R^2$ is methyl, $R^3$ is chlorine, $R^4$ is hydrogen and $R^5_y$ is hydrogen and $R^1$ for each compound corresponds to one group of Table A.

Table 44
Compounds of the general formula IA.4 where $R^2$ is methyl, $R^3$ is chlorine, $R^4$ is hydrogen and $R^5_y$ is hydrogen and $R^1$ for each compound corresponds to one group of Table A.

Table 45
Compounds of the general formula IA.5 where $R^2$ is methyl, $R^3$ is chlorine, $R^4$ is hydrogen and $R^5_y$ is hydrogen and $R^1$ for each compound corresponds to one group of Table A.

Table 46
Compounds of the general formula IA.6 where $R^2$ is methyl, $R^3$ is chlorine, $R^4$ is hydrogen and $R^5_y$ is hydrogen and $R^1$ for each compound corresponds to one group of Table A.

Table 47
Compounds of the general formula IA.7 where $R^2$ is methyl, $R^3$ is chlorine, $R^4$ is hydrogen and $R^5_y$ is hydrogen and $R^1$ for each compound corresponds to one group of Table A.

Table 48
Compounds of the general formula IA.8 where $R^2$ is methyl, $R^3$ is chlorine, $R^4$ is hydrogen and $R^5_y$ is hydrogen and $R^1$ for each compound corresponds to one group of Table A.

Table 49
Compounds of the general formula IA.9 where $R^2$ is methyl, $R^3$ is chlorine, $R^4$ is hydrogen and $R^5_y$ is hydrogen and $R^1$ for each compound corresponds to one group of Table A.

Table 50
Compounds of the general formula IA.10 where $R^2$ is methyl, $R^3$ is chlorine, $R^4$ is hydrogen and $R^5_y$ is hydrogen and $R^1$ for each compound corresponds to one group of Table A.

Table 51
Compounds of the general formula IB.1 where $R^2$ is methyl, $R^3$ is chlorine, $R^4$ is hydrogen and $R^5_y$ is hydrogen and $R^1$ for each compound corresponds to one group of Table A.

Table 52
Compounds of the general formula IB.2 where $R^2$ is methyl, $R^3$ is chlorine, $R^4$ is hydrogen and $R^5_y$ is hydrogen and $R^1$ for each compound corresponds to one group of Table A.

Table 53
Compounds of the general formula IB.3 where $R^2$ is methyl, $R^3$ is chlorine, $R^4$ is hydrogen and $R^5_y$ is hydrogen and $R^1$ for each compound corresponds to one group of Table A.

Table 54
Compounds of the general formula IB.4 where $R^2$ is methyl, $R^3$ is chlorine, $R^4$ is hydrogen and $R^5_y$ is hydrogen and $R^1$ for each compound corresponds to one group of Table A.

Table 55
Compounds of the general formula IB.5 where $R^2$ is methyl, $R^3$ is chlorine, $R^4$ is hydrogen and $R^5_y$ is hydrogen and $R^1$ for each compound corresponds to one group of Table A.

Table 56
Compounds of the general formula IB.6 where $R^2$ is methyl, $R^3$ is chlorine, $R^4$ is hydrogen and $R^5_y$ is hydrogen and $R^1$ for each compound corresponds to one group of Table A.

Table 57
Compounds of the general formula IB.7 where $R^2$ is methyl, $R^3$ is chlorine, $R^4$ is hydrogen and $R^5_y$ is hydrogen and $R^1$ for each compound corresponds to one group of Table A.

Table 58
Compounds of the general formula IB.8 where $R^2$ is methyl, $R^3$ is chlorine, $R^4$ is hydrogen and $R^5_y$ is hydrogen and $R^1$ for each compound corresponds to one group of Table A.

Table 59
Compounds of the general formula IB.9 where $R^2$ is methyl, $R^3$ is chlorine, $R^4$ is hydrogen and $R^5_y$ is hydrogen and $R^1$ for each compound corresponds to one group of Table A.

Table 60
Compounds of the general formula IB.10 where $R^2$ is methyl, $R^3$ is chlorine, $R^4$ is hydrogen and $R^5_y$ is hydrogen and $R^1$ for each compound corresponds to one group of Table A.

Table 61
Compounds of the general formula IA.1 where $R^2$ is methyl, $R^3$ is fluorine, $R^4$ is hydrogen and $R^5_y$ is hydrogen and $R^1$ for each compound corresponds to one group of Table A.

Table 62
Compounds of the general formula IA.2 where $R^2$ is methyl, $R^3$ is fluorine, $R^4$ is hydrogen and $R^5_y$ is hydrogen and $R^1$ for each compound corresponds to one group of Table A.

Table 63
Compounds of the general formula IA.3 where $R^2$ is methyl, $R^3$ is fluorine, $R^4$ is hydrogen and $R^5_y$ is hydrogen and $R^1$ for each compound corresponds to one group of Table A.

Table 64
Compounds of the general formula IA.4 where $R^2$ is methyl, $R^3$ is fluorine, $R^4$ is hydrogen and $R^5_y$ is hydrogen and $R^1$ for each compound corresponds to one group of Table A.

Table 65
Compounds of the general formula IA.5 where $R^2$ is methyl, $R^3$ is fluorine, $R^4$ is hydrogen and $R^5_y$ is hydrogen and $R^1$ for each compound corresponds to one group of Table A.

Table 66
Compounds of the general formula IA.6 where $R^2$ is methyl, $R^3$ is fluorine, $R^4$ is hydrogen and $R^5_y$ is hydrogen and $R^1$ for each compound corresponds to one group of Table A.

Table 67
Compounds of the general formula IA.7 where $R^2$ is methyl, $R^3$ is fluorine, $R^4$ is hydrogen and $R^5_y$ is hydrogen and $R^1$ for each compound corresponds to one group of Table A.

Table 68
Compounds of the general formula IA.8 where $R^2$ is methyl, $R^3$ is fluorine, $R^4$ is hydrogen and $R^5_y$ is hydrogen and $R^1$ for each compound corresponds to one group of Table A.

Table 69
Compounds of the general formula IA.9 where $R^2$ is methyl, $R^3$ is fluorine, $R^4$ is hydrogen and $R^5_y$ is hydrogen and $R^1$ for each compound corresponds to one group of Table A.

Table 70
Compounds of the general formula IA.10 where $R^2$ is methyl, $R^3$ is fluorine, $R^4$ is hydrogen and $R^5_y$ is hydrogen and $R^1$ for each compound corresponds to one group of Table A.

Table 71
Compounds of the general formula IB.1 where $R^2$ is methyl, $R^3$ is fluorine, $R^4$ is hydrogen and $R^5_y$ is hydrogen and $R^1$ for each compound corresponds to one group of Table A.

Table 72
Compounds of the general formula IB.2 where $R^2$ is methyl, $R^3$ is fluorine, $R^4$ is hydrogen and $R^5_y$ is hydrogen and $R^1$ for each compound corresponds to one group of Table A.

Table 73
Compounds of the general formula IB.3 where $R^2$ is methyl, $R^3$ is fluorine, $R^4$ is hydrogen and $R^5_y$ is hydrogen and $R^1$ for each compound corresponds to one group of Table A.

Table 74
Compounds of the general formula IB.4 where $R^2$ is methyl, $R^3$ is fluorine, $R^4$ is hydrogen and $R^5_y$ is hydrogen and $R^1$ for each compound corresponds to one group of Table A.

Table 75
Compounds of the general formula IB.5 where $R^2$ is methyl, $R^3$ is fluorine, $R^4$ is hydrogen and $R^5_y$ is hydrogen and $R^1$ for each compound corresponds to one group of Table A.

Table 76
Compounds of the general formula IB.6 where $R^2$ is methyl, $R^3$ is fluorine, $R^4$ is hydrogen and $R^5_y$ is hydrogen and $R^1$ for each compound corresponds to one group of Table A.

Table 77
Compounds of the general formula IB.7 where $R^2$ is methyl, $R^3$ is fluorine, $R^4$ is hydrogen and $R^5_y$ is hydrogen and $R^1$ for each compound corresponds to one group of Table A.

Table 78
Compounds of the general formula IB.8 where $R^2$ is methyl, $R^3$ is fluorine, $R^4$ is hydrogen and $R^5_y$ is hydrogen and $R^1$ for each compound corresponds to one group of Table A.

Table 79
Compounds of the general formula IB.9 where $R^2$ is methyl, $R^3$ is fluorine, $R^4$ is hydrogen and $R^5_y$ is hydrogen and $R^1$ for each compound corresponds to one group of Table A.

Table 80
Compounds of the general formula IB.10 where $R^2$ is methyl, $R^3$ is fluorine, $R^4$ is hydrogen and $R^5_y$ is hydrogen and $R^1$ for each compound corresponds to one group of Table A.

Table 81
Compounds of the general formula IA.1 where $R^2$ is methyl, $R^3$ is bromine, $R^4$ is hydrogen and $R^5_y$ is hydrogen and $R^1$ for each compound corresponds to one group of Table A.

Table 82
Compounds of the general formula IA.2 where $R^2$ is methyl, $R^3$ is bromine, $R^4$ is hydrogen and $R^5_y$ is hydrogen and $R^1$ for each compound corresponds to one group of Table A.

Table 83
Compounds of the general formula IA.3 where $R^2$ is methyl, $R^3$ is bromine, $R^4$ is hydrogen and $R^5_y$ is hydrogen and $R^1$ for each compound corresponds to one group of Table A.

Table 84
Compounds of the general formula IA.4 where $R^2$ is methyl, $R^3$ is bromine, $R^4$ is hydrogen and $R^5_y$ is hydrogen and $R^1$ for each compound corresponds to one group of Table A.

Table 85
Compounds of the general formula IA.5 where $R^2$ is methyl, $R^3$ is bromine, $R^4$ is hydrogen and $R^5_y$ is hydrogen and $R^1$ for each compound corresponds to one group of Table A.

Table 86
Compounds of the general formula IA.6 where $R^2$ is methyl, $R^3$ is bromine, $R^4$ is hydrogen and $R^5_y$ is hydrogen and $R^1$ for each compound corresponds to one group of Table A.

Table 87
Compounds of the general formula IA.7 where $R^2$ is methyl, $R^3$ is bromine, $R^4$ is hydrogen and $R^5_y$ is hydrogen and $R^1$ for each compound corresponds to one group of Table A.

Table 88
Compounds of the general formula IA.8 where $R^2$ is methyl, $R^3$ is bromine, $R^4$ is hydrogen and $R^5_y$ is hydrogen and $R^1$ for each compound corresponds to one group of Table A.

Table 89
Compounds of the general formula IA.9 where $R^2$ is methyl, $R^3$ is bromine, $R^4$ is hydrogen and $R^5_y$ is hydrogen and $R^1$ for each compound corresponds to one group of Table A.

Table 90
Compounds of the general formula IA.10 where $R^2$ is methyl, $R^3$ is bromine, $R^4$ is hydrogen and $R^5_y$ is hydrogen and $R^1$ for each compound corresponds to one group of Table A.

Table 91
Compounds of the general formula IB.1 where $R^2$ is methyl, $R^3$ is bromine, $R^4$ is hydrogen and $R^5_y$ is hydrogen and $R^1$ for each compound corresponds to one group of Table A.

Table 92
Compounds of the general formula IB.2 where $R^2$ is methyl, $R^3$ is bromine, $R^4$ is hydrogen and $R^5_y$ is hydrogen and $R^1$ for each compound corresponds to one group of Table A.

Table 93
Compounds of the general formula IB.3 where $R^2$ is methyl, $R^3$ is bromine, $R^4$ is hydrogen and $R^5_y$ is hydrogen and $R^1$ for each compound corresponds to one group of Table A.

Table 94
Compounds of the general formula IB.4 where $R^2$ is methyl, $R^3$ is bromine, $R^4$ is hydrogen and $R^5_y$ is hydrogen and $R^1$ for each compound corresponds to one group of Table A.

Table 95
Compounds of the general formula IB.5 where $R^2$ is methyl, $R^3$ is bromine, $R^4$ is hydrogen and $R^5_y$ is hydrogen and $R^1$ for each compound corresponds to one group of Table A.

Table 96
Compounds of the general formula IB.6 where $R^2$ is methyl, $R^3$ is bromine, $R^4$ is hydrogen and $R^5_y$ is hydrogen and $R^1$ for each compound corresponds to one group of Table A.

Table 97
Compounds of the general formula IB.7 where $R^2$ is methyl, $R^3$ is bromine, $R^4$ is hydrogen and $R^5_y$ is hydrogen and $R^1$ for each compound corresponds to one group of Table A.

Table 98
Compounds of the general formula IB.8 where $R^2$ is methyl, $R^3$ is bromine, $R^4$ is hydrogen and $R^5_y$ is hydrogen and $R^1$ for each compound corresponds to one group of Table A.

Table 99
Compounds of the general formula IB.9 where $R^2$ is methyl, $R^3$ is bromine, $R^4$ is hydrogen and $R^5_y$ is hydrogen and $R^1$ for each compound corresponds to one group of Table A.

Table 100
Compounds of the general formula IB.10 where $R^2$ is methyl, $R^3$ is bromine, $R^4$ is hydrogen and $R^5_y$ is hydrogen and $R^1$ for each compound corresponds to one group of Table A.

Table 101
Compounds of the general formula IA.1 where $R^2$ is methyl, $R^3$ is trifluoromethyl, $R^4$ is hydrogen and $R^5_y$ is hydrogen and $R^1$ for each compound corresponds to one group of Table A.

Table 102
Compounds of the general formula IA.2 where $R^2$ is methyl, $R^3$ is trifluoromethyl, $R^4$ is hydrogen and $R^5_y$ is hydrogen and $R^1$ for each compound corresponds to one group of Table A.

Table 103
Compounds of the general formula IA.3 where $R^2$ is methyl, $R^3$ is trifluoromethyl, $R^4$ is hydrogen and $R^5_y$ is hydrogen and $R^1$ for each compound corresponds to one group of Table A.

Table 104
Compounds of the general formula IA.4 where $R^2$ is methyl, $R^3$ is trifluoromethyl, $R^4$ is hydrogen and $R^5_y$ is hydrogen and $R^1$ for each compound corresponds to one group of Table A.

Table 105
Compounds of the general formula IA.5 where $R^2$ is methyl, $R^3$ is trifluoromethyl, $R^4$ is hydrogen and $R^5_y$ is hydrogen and $R^1$ for each compound corresponds to one group of Table A.

Table 106
Compounds of the general formula IA.6 where $R^2$ is methyl, $R^3$ is trifluoromethyl, $R^4$ is hydrogen and $R^5_y$ is hydrogen and $R^1$ for each compound corresponds to one group of Table A.

Table 107
Compounds of the general formula IA.7 where $R^2$ is methyl, $R^3$ is trifluoromethyl, $R^4$ is hydrogen and $R^5_y$ is hydrogen and $R^1$ for each compound corresponds to one group of Table A.

Table 108
Compounds of the general formula IA.8 where $R^2$ is methyl, $R^3$ is trifluoromethyl, $R^4$ is hydrogen and $R^5_y$ is hydrogen and $R^1$ for each compound corresponds to one group of Table A.

Table 109
Compounds of the general formula IA.9 where $R^2$ is methyl, $R^3$ is trifluoromethyl, $R^4$ is hydrogen and $R^5_y$ is hydrogen and $R^1$ for each compound corresponds to one group of Table A.

Table 110
Compounds of the general formula IA.10 where $R^2$ is methyl, $R^3$ is trifluoromethyl, $R^4$ is hydrogen and $R^5_y$ is hydrogen and $R^1$ for each compound corresponds to one group of Table A.

Table 111
Compounds of the general formula IB.1 where $R^2$ is methyl, $R^3$ is trifluoromethyl, $R^4$ is hydrogen and $R^5_y$ is hydrogen and $R^1$ for each compound corresponds to one group of Table A.

Table 112
Compounds of the general formula IB.2 where $R^2$ is methyl, $R^3$ is trifluoromethyl, $R^4$ is hydrogen and $R^5_y$ is hydrogen and $R^1$ for each compound corresponds to one group of Table A.

Table 113
Compounds of the general formula IB.3 where $R^2$ is methyl, $R^3$ is trifluoromethyl, $R^4$ is hydrogen and $R^5_y$ is hydrogen and $R^1$ for each compound corresponds to one group of Table A.

Table 114
Compounds of the general formula IB.4 where $R^2$ is methyl, $R^3$ is trifluoromethyl, $R^4$ is hydrogen and $R^5_y$ is hydrogen and $R^1$ for each compound corresponds to one group of Table A.

Table 115
Compounds of the general formula IB.5 where $R^2$ is methyl, $R^3$ is trifluoromethyl, $R^4$ is hydrogen and $R^5_y$ is hydrogen and $R^1$ for each compound corresponds to one group of Table A.

Table 116
Compounds of the general formula IB.6 where $R^2$ is methyl, $R^3$ is trifluoromethyl, $R^4$ is hydrogen and $R^5_y$ is hydrogen and $R^1$ for each compound corresponds to one group of Table A.

Table 117
Compounds of the general formula IB.7 where $R^2$ is methyl, $R^3$ is trifluoromethyl, $R^4$ is hydrogen and $R^5_y$ is hydrogen and $R^1$ for each compound corresponds to one group of Table A.

Table 118
Compounds of the general formula IB.8 where $R^2$ is methyl, $R^3$ is trifluoromethyl, $R^4$ is hydrogen and $R^5_y$ is hydrogen and $R^1$ for each compound corresponds to one group of Table A.

Table 119
Compounds of the general formula IB.9 where $R^2$ is methyl, $R^3$ is trifluoromethyl, $R^4$ is hydrogen and $R^5_y$ is hydrogen and $R^1$ for each compound corresponds to one group of Table A.

Table 120
Compounds of the general formula IB.10 where $R^2$ is methyl, $R^3$ is trifluoromethyl, $R^4$ is hydrogen and $R^5_y$ is hydrogen and $R^1$ for each compound corresponds to one group of Table A.

Table 121
Compounds of the general formula IA.1 where $R^2$ is methyl, $R^3$ is methyl, $R^4$ is methyl and $R^5_y$ is hydrogen and $R^1$ for each compound corresponds to one group of Table A.

Table 122
Compounds of the general formula IA.2 where $R^2$ is methyl, $R^3$ is methyl, $R^4$ is methyl and $R^5_y$ is hydrogen and $R^1$ for each compound corresponds to one group of Table A.

Table 123
Compounds of the general formula IA.3 where $R^2$ is methyl, $R^3$ is methyl, $R^4$ is methyl and $R^5_y$ is hydrogen and $R^1$ for each compound corresponds to one group of Table A.

Table 124
Compounds of the general formula IA.4 where $R^2$ is methyl, $R^3$ is methyl, $R^4$ is methyl and $R^5_y$ is hydrogen and $R^1$ for each compound corresponds to one group of Table A.

Table 125
Compounds of the general formula IA.5 where $R^2$ is methyl, $R^3$ is methyl, $R^4$ is methyl and $R^5_y$ is hydrogen and $R^1$ for each compound corresponds to one group of Table A.

Table 126
Compounds of the general formula IA.6 where $R^2$ is methyl, $R^3$ is methyl, $R^4$ is methyl and $R^5_y$ is hydrogen and $R^1$ for each compound corresponds to one group of Table A.

Table 127
Compounds of the general formula IA.7 where $R^2$ is methyl, $R^3$ is methyl, $R^4$ is methyl and $R^5_y$ is hydrogen and $R^1$ for each compound corresponds to one group of Table A.

Table 128
Compounds of the general formula IA.8 where $R^2$ is methyl, $R^3$ is methyl, $R^4$ is methyl and $R^5_y$ is hydrogen and $R^1$ for each compound corresponds to one group of Table A.

Table 129
Compounds of the general formula IA.9 where $R^2$ is methyl, $R^3$ is methyl, $R^4$ is methyl and $R^5_y$ is hydrogen and $R^1$ for each compound corresponds to one group of Table A.

Table 130
Compounds of the general formula IA.10 where $R^2$ is methyl, $R^3$ is methyl, $R^4$ is methyl and $R^5_y$ is hydrogen and $R^1$ for each compound corresponds to one group of Table A.

Table 131
Compounds of the general formula IB.1 where $R^2$ is methyl, $R^3$ is methyl, $R^4$ is methyl and $R^5_y$ is hydrogen and $R^1$ for each compound corresponds to one group of Table A.

Table 132
Compounds of the general formula IB.2 where $R^2$ is methyl, $R^3$ is methyl, $R^4$ is methyl and $R^5_y$ is hydrogen and $R^1$ for each compound corresponds to one group of Table A.

Table 133
Compounds of the general formula IB.3 where $R^2$ is methyl, $R^3$ is methyl, $R^4$ is methyl and $R^5_y$ is hydrogen and $R^1$ for each compound corresponds to one group of Table A.

Table 134
Compounds of the general formula IB.4 where $R^2$ is methyl, $R^3$ is methyl, $R^4$ is methyl and $R^5_y$ is hydrogen and $R^1$ for each compound corresponds to one group of Table A.

Table 135
Compounds of the general formula IB.5 where $R^2$ is methyl, $R^3$ is methyl, $R^4$ is methyl and $R^5_y$ is hydrogen and $R^1$ for each compound corresponds to one group of Table A.

Table 136
Compounds of the general formula IB.6 where $R^2$ is methyl, $R^3$ is methyl, $R^4$ is methyl and $R^5_y$ is hydrogen and $R^1$ for each compound corresponds to one group of Table A.

Table 137
Compounds of the general formula IB.7 where $R^2$ is methyl, $R^3$ is methyl, $R^4$ is methyl and $R^5_y$ is hydrogen and $R^1$ for each compound corresponds to one group of Table A.

Table 138
Compounds of the general formula IB.8 where $R^2$ is methyl, $R^3$ is methyl, $R^4$ is methyl and $R^5_y$ is hydrogen and $R^1$ for each compound corresponds to one group of Table A.

Table 139
Compounds of the general formula IB.9 where $R^2$ is methyl, $R^3$ is methyl, $R^4$ is methyl and $R^5_y$ is hydrogen and $R^1$ for each compound corresponds to one group of Table A.

Table 140
Compounds of the general formula IB.10 where $R^2$ is methyl, $R^3$ is methyl, $R^4$ is methyl and $R^5_y$ is hydrogen and $R^1$ for each compound corresponds to one group of Table A.

TABLE A

| No. | $R^1$ |
|---|---|
| A.1 | H |
| A.2 | $CH_3$ |
| A.3 | $C_2H_5$ |
| A.4 | $n-C_3H_7$ |
| A.5 | $i-C_3H_7$ |
| A.6 | cyclopropyl |
| A.7 | $n-C_4H_9$ |
| A.8 | $s-C_4H_9$ |
| A.9 | $i-C_4H_9$ |
| A.10 | $t-C_4H_9$ |
| A.11 | $n-C_5H_{11}$ |
| A.12 | $i-C_5H_{11}$ |
| A.13 | $neo-C_5H_{11}$ |
| A.14 | cyclopentyl |
| A.15 | $n-C_6H_{13}$ |
| A.16 | cyclohexyl |
| A.17 | $n-C_8H_{17}$ |
| A.18 | $CH_2CH_2Cl$ |
| A.19 | $(CH_2)_4Cl$ |
| A.20 | $CH_2CN$ |
| A.21 | $CH_2CH_2CN$ |
| A.22 | $(CH_2)_3CN$ |
| A.23 | $(CH_2)_4CN$ |
| A.24 | $(CH_2)_6CN$ |
| A.25 | cyclohexylmethyl |
| A.26 | 2-cyclohexyleth-1-yl |
| A.27 | cyclopropylmethyl |
| A.28 | 2-cyclopropyleth-1-yl |
| A.29 | 2-methoxyeth-1-yl |
| A.30 | 2-ethoxyeth-1-yl |
| A.31 | 2-isopropoxyeth-1-yl |
| A.32 | 3-methoxyprop-1-yl |
| A.33 | 3-ethoxyprop-1-yl |
| A.34 | 3-isopropoxyprop-1-yl |
| A.35 | 4-methoxybut-1-yl |
| A.36 | 4-isopropoxybut-1-yl |
| A.37 | propen-3-yl |
| A.38 | but-2-en-1-yl |
| A.39 | 3-methylbut-2-en-1-yl |
| A.40 | 2-vinyloxyeth-1-yl |
| A.41 | allyloxyeth-1-yl |
| A.42 | 2-trifluoromethoxyeth-1-yl |
| A.43 | 3-trifluoromethoxyprop-1-yl |
| A.44 | 4-difluoromethoxybut-1-yl |
| A.45 | hydroxycarbonylmethyl |
| A.46 | methoxycarbonylmethyl |
| A.47 | aminocarbonylmethyl |
| A.48 | N-methylaminocarbonylmethyl |
| A.49 | N,N-dimethylaminocarbonylmethyl |
| A.50 | 2-hydroxycarbonyleth-1-yl |
| A.51 | 2-methoxycarbonyleth-1-yl |
| A.52 | 2-aminocarbonyleth-1-yl |
| A.53 | 2-N-methylaminocarbonyleth-1-yl |
| A.54 | 2-dimethylaminocarbonyleth-1-yl |
| A.55 | 2-aminoeth-1-yl |
| A.56 | 2-aminoprop-1-yl |
| A.57 | 4-aminobut-1-yl |
| A.58 | 3-dimethylaminoprop-1-yl |
| A.59 | 4-aminothiocarbonylbut-1-yl |
| A.60 | 2-oxopropyl |
| A.61 | cyclohexyl |
| A.62 | cyclopropyl |
| A.63 | cyclopentyl |
| A.64 | 2-methoxyiminoprop-1-yl |
| A.65 | 2-methoxyiminoeth-1-yl |
| A.66 | 6-aminocarbonylhex-1-yl |
| A.67 | 3-aminothiocarbonylprop-1-yl |
| A.68 | 2-aminothiocarbonyleth-1-yl |
| A.69 | aminothiocarbonylmethyl |
| A.70 | 4-(N,N-dimethylamino)but-1-yl |
| A.71 | 2-(methylthio)eth-1-yl |
| A.72 | 2-(methylsulfonyl)eth-1-yl |
| A.73 | 4-(methylthio)prop-1-yl |
| A.74 | 4-(methylsulfonyl)prop-1-yl |
| A.75 | benzyl |

TABLE A-continued

| No. | R¹ |
|---|---|
| A.76 | 2-F—$C_6H_4$—$CH_2$ |
| A.77 | 3-F—$C_6H_4$—$CH_2$ |
| A.78 | 4-F—$C_6H_4$—$CH_2$ |
| A.79 | 2,3-$F_2$—$C_6H_3$—$CH_2$ |
| A.80 | 2,4-$F_2$—$C_6H_3$—$CH_2$ |
| A.81 | 2,5-$F_2$—$C_6H_3$—$CH_2$ |
| A.82 | 2,6-$F_2$—$C_6H_3$—$CH_2$ |
| A.83 | 3,4-$F_2$—$C_6H_3$—$CH_2$ |
| A.84 | 3,5-$F_2$—$C_6H_3$—$CH_2$ |
| A.85 | 2-Cl—$C_6H_4$—$CH_2$ |
| A.86 | 3-Cl—$C_6H_4$—$CH_2$ |
| A.87 | 4-Cl—$C_6H_4$—$CH_2$ |
| A.88 | 2,3-$Cl_2$—$C_6H_3$—$CH_2$ |
| A.89 | 2,4-$Cl_2$—$C_6H_3$—$CH_2$ |
| A.90 | 2,5-$Cl_2$—$C_6H_3$—$CH_2$ |
| A.91 | 2,6-$Cl_2$—$C_6H_3$—$CH_2$ |
| A.92 | 3,4-$Cl_2$—$C_6H_3$—$CH_2$ |
| A.93 | 3,5-$Cl_2$—$C_6H_3$—$CH_2$ |
| A.94 | 2,3,4-$Cl_3$—$C_6H_2$—$CH_2$ |
| A.95 | 2,3,5-$Cl_3$—$C_6H_2$—$CH_2$ |
| A.96 | 2,3,6-$Cl_3$—$C_6H_2$—$CH_2$ |
| A.97 | 2,4,5-$Cl_3$—$C_6H_2$—$CH_2$ |
| A.98 | 3,4,6-$Cl_3$—$C_6H_2$—$CH_2$ |
| A.99 | 3,4,5-$Cl_3$—$C_6H_2$—$CH_2$ |
| A.100 | 2-Br—$C_6H_4$—$CH_2$ |
| A.101 | 3-Br—$C_6H_4$—$CH_2$ |
| A.102 | 4-Br—$C_6H_4$—$CH_2$ |
| A.103 | 2,3-$Br_2$—$C_6H_3$—$CH_2$ |
| A.104 | 2,3-$Br_2$—$C_6H_3$—$CH_2$ |
| A.105 | 2,3-$Br_2$—$C_6H_3$—$CH_2$ |
| A.106 | 2,3-$Br_2$—$C_6H_3$—$CH_2$ |
| A.107 | 2,3-$Br_2$—$C_6H_3$—$CH_2$ |
| A.108 | 2,3-$Br_2$—$C_6H_3$—$CH_2$ |
| A.109 | 2-F, 3-Cl—$C_6H_3$—$CH_2$ |
| A.110 | 2-F, 4-Cl—$C_6H_3$—$CH_2$ |
| A.111 | 2-F, 5-Cl—$C_6H_3$—$CH_2$ |
| A.112 | 2-F, 3-Br—$C_6H_3$—$CH_2$ |
| A.113 | 2-F, 4-Br—$C_6H_3$—$CH_2$ |
| A.114 | 2-F, 5-Br—$C_6H_3$—$CH_2$ |
| A.115 | 2-Cl, 3-Br—$C_6H_3$—$CH_2$ |
| A.116 | 2-Cl, 4-Br—$C_6H_3$—$CH_2$ |
| A.117 | 2-Cl, 5-Br—$C_6H_3$—$CH_2$ |
| A.118 | 3-F, 4-Cl—$C_6H_3$—$CH_2$ |
| A.119 | 3-F, 5-Cl—$C_6H_3$—$CH_2$ |
| A.120 | 3-F, 6-Cl—$C_6H_3$—$CH_2$ |
| A.121 | 3-F, 4-Br—$C_6H_3$—$CH_2$ |
| A.122 | 3-F, 5-Br—$C_6H_3$—$CH_2$ |
| A.123 | 3-F, 6-Br—$C_6H_3$—$CH_2$ |
| A.124 | 3-Cl, 4-Br—$C_6H_3$—$CH_2$ |
| A.125 | 3-Cl, 5-Br—$C_6H_3$—$CH_2$ |
| A.126 | 3-Cl, 6-Br—$C_6H_3$—$CH_2$ |
| A.127 | 4-F, 5-Cl—$C_6H_3$—$CH_2$ |
| A.128 | 4-F, 6-Cl—$C_6H_3$—$CH_2$ |
| A.129 | 4-F, 5-Br—$C_6H_3$—$CH_2$ |
| A.130 | 4-F, 6-Br—$C_6H_3$—$CH_2$ |
| A.131 | 4-Cl, 5-Br—$C_6H_3$—$CH_2$ |
| A.132 | 5-F, 6-Cl—$C_6H_3$—$CH_2$ |
| A.133 | 5-F, 6-Br—$C_6H_3$—$CH_2$ |
| A.134 | 5-Cl, 6-Br—$C_6H_3$—$CH_2$ |
| A.135 | 3-Br, 4-Cl, 5-Br—$C_6H_2$—$CH_2$ |
| A.136 | 2-CN—$C_6H_4$—$CH_2$ |
| A.137 | 3-CN—$C_6H_4$—$CH_2$ |
| A.138 | 4-CN—$C_6H_4$—$CH_2$ |
| A.139 | 2-$NO_2$—$C_6H_4$—$CH_2$ |
| A.140 | 3-$NO_2$—$C_6H_4$—$CH_2$ |
| A.141 | 4-$NO_2$—$C_6H_4$—$CH_2$ |
| A.142 | 2-$CH_3$—$C_6H_4$—$CH_2$ |
| A.143 | 3-$CH_3$—$C_6H_4$—$CH_2$ |
| A.144 | 4-$CH_3$—$C_6H_4$—$CH_2$ |
| A.145 | 2,3-$(CH_3)_2$—$C_6H_3$—$CH_2$ |
| A.146 | 2,4-$(CH_3)_2$—$C_6H_3$—$CH_2$ |
| A.147 | 2,5-$(CH_3)_2$—$C_6H_3$—$CH_2$ |
| A.148 | 2,6-$(CH_3)_2$—$C_6H_3$—$CH_2$ |
| A.149 | 3,4-$(CH_3)_2$—$C_6H_3$—$CH_2$ |
| A.150 | 3,5-$(CH_3)_2$—$C_6H_3$—$CH_2$ |
| A.151 | 2-$C_2H_5$—$C_6H_4$—$CH_2$ |
| A.152 | 3-$C_2H_5$—$C_6H_4$—$CH_2$ |
| A.153 | 4-$C_2H_5$—$C_6H_4$—$CH_2$ |
| A.154 | 2-i-$C_3H_7$—$C_6H_4$—$CH_2$ |
| A.155 | 3-i-$C_3H_7$—$C_6H_4$—$CH_2$ |
| A.156 | 4-i-$C_3H_7$—$C_6H_4$—$CH_2$ |
| A.157 | 2-cyclohexyl-$C_6H_4$—$CH_2$ |
| A.158 | 3-cyclohexyl-$C_6H_4$—$CH_2$ |
| A.159 | 4-cyclohexyl-$C_6H_4$—$CH_2$ |
| A.160 | 2-vinyl-$C_6H_4$—$CH_2$ |
| A.161 | 3-vinyl-$C_6H_4$—$CH_2$ |
| A.162 | 4-vinyl-$C_6H_4$—$CH_2$ |
| A.163 | 2-allyl-$C_6H_4$—$CH_2$ |
| A.164 | 3-allyl-$C_6H_4$—$CH_2$ |
| A.165 | 4-allyl-$C_6H_4$—$CH_2$ |
| A.166 | 2-$C_6H_5$—$C_6H_4$—$CH_2$ |
| A.167 | 3-$C_6H_5$—$C_6H_4$—$CH_2$ |
| A.168 | 4-$C_6H_5$—$C_6H_4$—$CH_2$ |
| A.169 | 3-$CH_3$, 5-t-$C_4H_9$—$C_6H_3$—$CH_2$ |
| A.170 | 2-OH—$C_6H_4$—$CH_2$ |
| A.171 | 3-OH—$C_6H_4$—$CH_2$ |
| A.172 | 4-OH—$C_6H_4$—$CH_2$ |
| A.173 | 2-$OCH_3$—$C_6H_4$—$CH_2$ |
| A.174 | 3-$OCH_3$—$C_6H_4$—$CH_2$ |
| A.175 | 4-$OCH_3$—$C_6H_4$—$CH_2$ |
| A.176 | 2,3-$(OCH_3)_2$—$C_6H_3$—$CH_2$ |
| A.177 | 2,4-$(OCH_3)_2$—$C_6H_3$—$CH_2$ |
| A.178 | 2,5-$(OCH_3)_2$—$C_6H_3$—$CH_2$ |
| A.179 | 3,4-$(OCH_3)_2$—$C_6H_3$—$CH_2$ |
| A.180 | 3,5-$(OCH_3)_2$—$C_6H_3$—$CH_2$ |
| A.181 | 3,4,5-$(OCH_3)_3$—$C_6H_2$—$CH_2$ |
| A.182 | 2-$OC_2H_5$—$C_6H_4$—$CH_2$ |
| A.183 | 3-$OC_2H_5$—$C_6H_4$—$CH_2$ |
| A.184 | 4-$OC_2H_5$—$C_6H_4$—$CH_2$ |
| A.185 | 2-O-(n-$C_3H_7$)—$C_6H_4$—$CH_2$ |
| A.186 | 3-O-(n-$C_3H_7$)—$C_6H_4$—$CH_2$ |
| A.187 | 4-O-(n-$C_3H_7$)—$C_6H_4$—$CH_2$ |
| A.188 | 2-O-(i-$C_3H_7$)—$C_6H_4$—$CH_2$ |
| A.189 | 3-O-(i-$C_3H_7$)—$C_6H_4$—$CH_2$ |
| A.190 | 4-O-(i-$C_3H_7$)—$C_6H_4$—$CH_2$ |
| A.191 | 4-O-(n-$C_4H_9$)—$C_6H_4$—$CH_2$ |
| A.192 | 3-O-(t-$C_4H_9$)—$C_6H_4$—$CH_2$ |
| A.193 | 4-O-(n-$C_6H_{13}$)—$C_6H_4$—$CH_2$ |
| A.194 | 2-O-allyl-$C_6H_4$—$CH_2$ |
| A.195 | 3-O-allyl-$C_6H_4$—$CH_2$ |
| A.196 | 4-O-allyl-$C_6H_4$—$CH_2$ |
| A.197 | 2-$CF_3$—$C_6H_4$—$CH_2$ |
| A.198 | 3-$CF_3$—$C_6H_4$—$CH_2$ |
| A.199 | 4-$CF_3$—$C_6H_4$—$CH_2$ |
| A.200 | 2-acetyl-$C_6H_4$—$CH_2$ |
| A.201 | 3-acetyl-$C_6H_4$—$CH_2$ |
| A.202 | 4-acetyl-$C_6H_4$—$CH_2$ |
| A.203 | 2-methoxycarbonyl-$C_6H_4$—$CH_2$ |
| A.204 | 3-methoxycarbonyl-$C_6H_4$—$CH_2$ |
| A.205 | 4-methoxycarbonyl-$C_6H_4$—$CH_2$ |
| A.206 | 2-aminocarbonyl-$C_6H_4$—$CH_2$ |
| A.207 | 3-aminocarbonyl-$C_6H_4$—$CH_2$ |
| A.208 | 4-aminocarbonyl-$C_6H_4$—$CH_2$ |
| A.209 | 2-dimethylaminocarbonyl-$C_6H_4$—$CH_2$ |
| A.210 | 3-dimethylaminocarbonyl-$C_6H_4$—$CH_2$ |
| A.211 | 4-dimethylaminocarbonyl-$C_6H_4$—$CH_2$ |
| A.212 | 2-(N-methylaminocarbonyl)-$C_6H_4$—$CH_2$ |
| A.213 | 3-(N-methylaminocarbonyl)-$C_6H_4$—$CH_2$ |
| A.214 | 4-(N-methylaminocarbonyl)-$C_6H_4$—$CH_2$ |
| A.215 | 2-$H_2N$—$C_6H_4$—$CH_2$ |
| A.216 | 3-$H_2N$—$C_6H_4$—$CH_2$ |
| A.217 | 4-$H_2N$—$C_6H_4$—$CH_2$ |
| A.218 | 2-aminothiocarbonyl-$C_6H_4$—$CH_2$ |
| A.219 | 3-aminothiocarbonyl-$C_6H_4$—$CH_2$ |
| A.220 | 4-aminothiocarbonyl-$C_6H_4$—$CH_2$ |
| A.221 | 2-methoxyiminomethyl-$C_6H_4$—$CH_2$ |
| A.222 | 3-methoxyiminomethyl-$C_6H_4$—$CH_2$ |
| A.223 | 4-methoxyiminomethyl-$C_6H_4$—$CH_2$ |
| A.224 | 2-formyl-$C_6H_4$—$CH_2$ |
| A.225 | 3-formyl-$C_6H_4$—$CH_2$ |
| A.226 | 4-formyl-$C_6H_4$—$CH_2$ |
| A.227 | 2-(1'-methoxyiminoeth-1'-yl)-$C_6H_4$—$CH_2$ |
| A.228 | 3-(1'-methoxyiminoeth-1'-yl)-$C_6H_4$—$CH_2$ |
| A.229 | 4-(1'-methoxyiminoeth-1'-yl)-$C_6H_4$—$CH_2$ |

TABLE A-continued

| No. | R[1] |
|---|---|
| A.230 | 2-SCH$_3$—C$_6$H$_4$—CH$_2$ |
| A.231 | 3-SCH$_3$—C$_6$H$_4$—CH$_2$ |
| A.232 | 4-SCH$_3$—C$_6$H$_4$—CH$_2$ |
| A.233 | 2-SO$_2$CH$_3$—C$_6$H$_4$—CH$_2$ |
| A.234 | 3-SO$_2$CH$_3$—C$_6$H$_4$—CH$_2$ |
| A.235 | 4-SO$_2$CH$_3$—C$_6$H$_4$—CH$_2$ |
| A.236 | 2-OCF$_3$—C$_6$H$_4$—CH$_2$ |
| A.237 | 3-OCF$_3$—C$_6$H$_4$—CH$_2$ |
| A.238 | 4-OCF$_3$—C$_6$H$_4$—CH$_2$ |
| A.239 | 2-OCHF$_2$—C$_6$H$_4$—CH$_2$ |
| A.240 | 3-OCHF$_2$—C$_6$H$_4$—CH$_2$ |
| A.241 | 4-OCHF$_3$—C$_6$H$_4$—CH$_2$ |
| A.242 | 3-CF$_3$, 4-OCF$_3$—C$_6$H$_3$—CH$_2$ |
| A.243 | 1-naphthyl-CH$_2$ |
| A.244 | 2-naphthyl-CH$_2$ |
| A.245 | 2-phenoxyeth-1-yl |
| A.246 | 2-(2'-chlorophenoxy)eth-1-yl |
| A.247 | 2-(3'-chlorophenoxy)eth-1-yl |
| A.248 | 2-(4'-chlorophenoxy)eth-1-yl |
| A.249 | 2-(3',5'-dichlorophenoxy)eth-1-yl |
| A.250 | 2-(2'-cyanophenoxy)eth-1-yl |
| A.251 | 2-(3'-cyanophenoxy)eth-1-yl |
| A.252 | 2-(4'-cyanophenoxy)eth-1-yl |
| A.253 | 2-(2'-methylphenoxy)eth-1-yl |
| A.254 | 2-(3'-methylphenoxy)eth-1-yl |
| A.255 | 2-(4'-methylphenoxy)eth-1-y1 |
| A.256 | 2-(3'-t-butylphenoxy)eth-1-yl |
| A.257 | 2-(4'-t-butylphenoxy)eth-1-yl |
| A.258 | 2-(2'-nitrophenoxy)eth-1-yl |
| A.259 | 2-(3'-nitrophenoxy)eth-1-yl |
| A.260 | 2-(4'-nitrophenoxy)eth-1-yl |
| A.261 | 2-(2'-methoxyphenoxy)eth-1-yl |
| A.262 | 2-(3'-methoxyphenoxy)eth-1-yl |
| A.263 | 2-(4'-methoxyphenoxy)eth-1-yl |
| A.264 | 2-(2'-trifluoromethylphenoxy)eth-1-yl |
| A.265 | 2-(3'-trifluoromethylphenoxy)eth-1-yl |
| A.266 | 2-(4'-trifluoromethylphenoxy)eth-1-yl |
| A.267 | 2-(2'-acetylphenoxy)eth-1-yl |
| A.268 | 2-(3'-acetylphenoxy)eth-1-yl |
| A.269 | 2-(4'-acetylphenoxy)eth-1-yl |
| A.270 | 2-(2'-methoxycarbonyl)eth-1-yl |
| A.271 | 2-(3'-methoxycarbonyl)eth-1-yl |
| A.272 | 2-(4'-methoxycarbonyl)eth-1-yl |
| A.273 | 2-(2'-dimethylaminocarbonyl)eth-1-yl |
| A.274 | 2-(3'-dimethylaminocarbonyl)eth-1-yl |
| A.275 | 2-(4'-dimethylaminocarbonyl)eth-1-yl |
| A.276 | 2-(2'-aminothiocarbonyl)eth-1-yl |
| A.277 | 2-(3'-aminothiocarbonyl)eth-1-yl |
| A.278 | 2-(4'-aminothiocarbonyl)eth-1-yl |
| A.279 | 2-(2'-methylsulfonyl)eth-1-yl |
| A.280 | 2-(3'-methylsulfonyl)eth-1-yl |
| A.281 | 2-(4'-methylsulfonyl)eth-1-yl |
| A.282 | 3-phenoxyprop-1-yl |
| A.283 | 3-(2'-chlorophenoxy)prop-1-yl |
| A.284 | 3-(3'-chlorophenoxy)prop-1-yl |
| A.285 | 3-(4'-chlorophenoxy)prop-1-yl |
| A.286 | 3-(3',5'-dichlorophenoxy)prop-1-yl |
| A.287 | 3-(2'-cyanophenoxy)prop-1-yl |
| A.288 | 3-(3'-cyanophenoxy)prop-1-yl |
| A.289 | 3-(4'-cyanophenoxy)prop-1-yl |
| A.290 | 3-(2'-methylphenoxy)prop-1-yl |
| A.291 | 3-(3'-methylphenoxy)prop-1-yl |
| A.292 | 3-(4'-methylphenoxy)prop-1-yl |
| A.293 | 3-(2'-methoxyphenoxy)prop-1-yl |
| A.294 | 3-(3'-methoxyphenoxy)prop-1-yl |
| A.295 | 3-(4'-methoxyphenoxy)prop-1-yl |
| A.296 | 3-(2'-trifluoromethylphenoxy)prop-1-yl |
| A.297 | 3-(3'-trifluoromethylphenoxy)prop-1-yl |
| A.298 | 3-(4'-trifluoromethylphenoxy)prop-1-yl |
| A.299 | 4-phenoxybut-1-yl |
| A.300 | 2-phenyleth-1-yl |
| A.301 | 2-(2'-chlorophenyl)eth-1-yl |
| A.302 | 2-(3'-chlorophenyl)eth-1-yl |
| A.303 | 2-(4'-chlorophenyl)eth-1-yl |
| A.304 | 2-(3',5'-dichlorophenyl)eth-1-yl |
| A.305 | 2-(2'-cyanophenyl)eth-1-yl |
| A.306 | 2-(3'-cyanophenyl)eth-1-yl |
| A.307 | 2-(4'-cyanophenyl)eth-1-yl |
| A.308 | 2-(2'-methylphenyl)eth-1-yl |
| A.309 | 2-(3'-methylphenyl)eth-1-yl |
| A.310 | 2-(4'-methylphenyl)eth-1-yl |
| A.311 | 2-(2'-methoxyphenyl)eth-1-yl |
| A.312 | 2-(3'-methoxyphenyl)eth-1-yl |
| A.313 | 2-(4'-methoxyphenyl)eth-1-yl |
| A.314 | 2-(2'-trifluoromethylphenyl)eth-1-yl |
| A.315 | 2-(3'-trifluoromethylphenyl)eth-1-yl |
| A.316 | 2-(4'-trifluoromethylphenyl)eth-1-yl |
| A.317 | 3-phenylprop-1-yl |
| A.318 | 3-(2'-chlorophenyl)prop-1-yl |
| A.319 | 3-(3'-chlorophenyl)prop-1-yl |
| A.320 | 3-(4'-chlorophenyl)prop-1-yl |
| A.321 | 3-(2'-cyanophenyl)prop-1-yl |
| A.322 | 3-(3'-cyanophenyl)prop-1-yl |
| A.323 | 3-(4'-cyanophenyl)prop-1-yl |
| A.324 | 3-(2'-trifluoromethylphenyl)prop-1-yl |
| A.325 | 4-phenylbut-1-yl |
| A.326 | 4-(4'-chlorophenyl)but-1-yl |
| A.327 | 6-(4'-chlorophenyl)hex-1-yl |
| A.328 | 2-pyridylmethyl |
| A.329 | 3-pyridylmethyl |
| A.330 | 4-pyridylmethyl |
| A.331 | 4-chloropyridin-2-ylmethyl |
| A.332 | 5-chloropyridin-2-ylmethyl |
| A.333 | 6-chloropyridin-2-ylmethyl |
| A.334 | 5-chloropyridin-3-ylmethyl |
| A.335 | 6-chloropyridin-3-ylmethyl |
| A.336 | 2-chloropyridin-4-ylmethyl |
| A.337 | 2-pyrimidinylmethyl |
| A.338 | 4-chloropyrimidin-2-ylmethyl |
| A.339 | 5-chloropyrimidin-2-ylmethyl |
| A.340 | 2-chloropyrimidin-4-ylmethyl |
| A.341 | 6-chloropyrimidin-4-ylmethyl |
| A.342 | 2-chloropyrimidin-5-ylmethyl |
| A.343 | 4-pyridazinylmethyl |
| A.344 | 2-pyrazinylmethyl |
| A.345 | 5-chloropyrazin-2-ylmethyl |
| A.346 | 6-chloropyrazin-2-ylmethyl |
| A.347 | 3-pyridazinylmethyl |
| A.348 | 6-chloropyridazin-3-ylmethyl |
| A.349 | 1,3,5-triazinylmethyl |
| A.350 | 2-furylmethyl |
| A.351 | 3-furylmethyl |
| A.352 | 4-bromofur-2-ylmethyl |
| A.353 | 5-chlorofur-2-ylmethyl |
| A.354 | 2-thienylmethyl |
| A.355 | 3-thienylmethyl |
| A.356 | 5-methylthien-3-ylmethyl |
| A.357 | 5-chlorothien-2-ylmethyl |
| A.358 | 2-chlorothien-4-ylmethyl |
| A.359 | 2-pyrrolylmethyl |
| A.360 | 3-pyrrolylmethyl |
| A.361 | 2-oxazolylmethyl |
| A.362 | 4-methyloxazol-2-ylmethyl |
| A.363 | 5-methyloxazol-2-ylmethyl |
| A.364 | 4-chlorooxazol-2-ylmethyl |
| A.365 | 5-chlorooxazol-2-ylmethyl |
| A.366 | 4-oxazolylmethyl |
| A.367 | 2-methyloxazol-4-ylmethyl |
| A.368 | 5-methyloxazol-4-ylmethyl |
| A.369 | 2-chlorooxazol-4-ylmethyl |
| A.370 | 5-chlorooxazol-4-ylmethyl |
| A.371 | 5-oxazolylmethyl |
| A.372 | 2-methyloxazol-5-ylmethyl |
| A.373 | 4-methyloxazol-5-ylmethyl |
| A.374 | 2-chlorooxazol-5-ylmethyl |
| A.375 | 4-chlorooxazol-5-ylmethyl |
| A.376 | 2-thiazolylmethyl |
| A.377 | 4-methylthiazol-2-ylmethyl |
| A.378 | 5-methylthiazol-2-ylmethyl |
| A.379 | 4-chlorothiazol-2-ylmethyl |
| A.380 | 5-chlorothiazol-2-ylmethyl |
| A.381 | 4-thiazolylmethyl |
| A.382 | 2-methylthiazol-4-ylmethyl |
| A.383 | 5-methylthiazol-4-ylmethyl |

TABLE A-continued

| No. | R¹ |
|---|---|
| A.384 | 2-chlorothiazol-4-ylmethyl |
| A.385 | 5-chlorothiazol-4-ylmethyl |
| A.386 | 5-thiazolylmethyl |
| A.387 | 2-methylthiazol-5-ylmethyl |
| A.388 | 4-methylthiazol-5-ylmethyl |
| A.389 | 2-chlorothiazol-5-ylmethyl |
| A.390 | 4-chlorothiazol-5-ylmethyl |
| A.391 | 3-isoxazolylmethyl |
| A.392 | 4-methylisoxazol-3-ylmethyl |
| A.393 | 5-methylisoxazol-3-ylmethyl |
| A.394 | 4-chloroisoxazol-3-ylmethyl |
| A.395 | 5-chloroisoxazol-3-ylmethyl |
| A.396 | 4-isoxazolylmethyl |
| A.397 | 3-methylisoxazol-4-ylmethyl |
| A.398 | 5-methylisoxazol-4-ylmethyl |
| A.399 | 3-chloroisoxazol-4-ylmethyl |
| A.400 | 5-chloroisoxazol-4-ylmethyl |
| A.401 | 5-isoxazolylmethyl |
| A.402 | 3-methylisoxazol-5-ylmethyl |
| A.403 | 4-methylisoxazol-5-ylmethyl |
| A.404 | 3-chloroisoxazol-5-ylmethyl |
| A.405 | 4-chloroisoxazol-5-ylmethyl |
| A.406 | 3-isothiazolylmethyl |
| A.407 | 4-methylisothiazol-3-ylmethyl |
| A.408 | 5-methylisothiazol-3-ylmethyl |
| A.409 | 4-chloroisothiazol-3-ylmethyl |
| A.410 | 5-chloroisothiazol-3-ylmethyl |
| A.411 | 4-isothiazolylmethyl |
| A.412 | 3-methylisothiazol-4-ylmethyl |
| A.413 | 5-methylisothiazol-4-ylmethyl |
| A.414 | 3-chloroisothiazol-4-ylmethyl |
| A.415 | 5-chloroisothiazol-4-ylmethyl |
| A.416 | 5-isothiazolylmethyl |
| A.417 | 3-methylisothiazol-5-ylmethyl |
| A.418 | 4-methylisothiazol-5-ylmethyl |
| A.419 | 3-chloroisothiazol-5-ylmethyl |
| A.420 | 4-chloroisothiazol-5-ylmethyl |
| A.421 | 4-imidazolylmethyl |
| A.422 | 1-phenylpyrazol-3-ylmethyl |
| A.423 | 1-methylimidazol-4-ylmethyl |
| A.424 | 1-phenyl-1,2,4-triazol-3-ylmethyl |
| A.425 | 1,2,4-oxadiazol-3-ylmethyl |
| A.426 | 5-chloro-1,2,4-oxadiazol-3-ylmethyl |
| A.427 | 5-methyl-1,2,4-oxadiazol-3-ylmethyl |
| A.428 | 5-trifluoromethyl-1,2,4-oxadiazol-3-ylmethyl |
| A.429 | 1,3,4-oxadiazol-2-ylmethyl |
| A.430 | 5-chloro-1,3,4-oxadiazol-2-ylmethyl |
| A.431 | 5-methyl-1,3,4-oxadiazol-2-ylmethyl |
| A.432 | 5-methoxy-1,3,4-oxadiazol-2-ylmethyl |
| A.433 | 1,2,4-thiadiazol-3-ylmethyl |
| A.434 | 5-chloro-1,2,4-thiadiazol-3-ylmethyl |
| A.435 | 5-methyl-1,2,4-thiadiazol-3-ylmethyl |
| A.436 | 1,3,4-thiadiazol-2-ylmethyl |
| A.437 | 5-chloro-1,3,4-thiadiazol-2-ylmethyl |
| A.438 | 5-methyl-1,3,4-thiadiazol-2-ylmethyl |
| A.439 | 5-cyano-1,3,4-thiadiazol-2-ylmethyl |
| A.440 | 2-(2'-pyridinyloxy)eth-1-yl |
| A.441 | 2-(3'-pyridinyloxy)eth-1-yl |
| A.442 | 2-(4'-pyridinyloxy)eth-1-yl |
| A.443 | 2-(2'-pyrimidinyloxy)eth-1-yl |
| A.444 | 2-(4'-pyrimidinyloxy)eth-1-yl |
| A.445 | 2-(5'-pyrimidinyloxy)eth-1-yl |
| A.446 | 2-(2'-pyrazinyloxy)eth-1-yl |
| A.447 | 2-(2'-pyridazinyloxy)eth-1-yl |
| A.448 | 2-(3'-pyridazinyloxy)eth-1-yl |
| A.449 | 2-(1',3',5'-triazinyloxy)eth-1-yl |
| A.450 | 2-(5'-methylisoxazol-3'-yloxy)eth-1-yl |
| A.451 | 2-(5'-chloroisoxazol-3'-yloxy)eth-1-yl |
| A.452 | 2-(2'-methoxythiazol-4'-yloxy)eth-1-yl |
| A.453 | 2-(4'-chlorooxazol-2'-yloxy)eth-1-yl |
| A.454 | 2-(1'-phenyl-1'H-1',2',4'-triazol-3'-yloxy)eth-1-yl |
| A.455 | 2-(1'-phenylpyrazol-3'-yloxy)eth-1-yl |
| A.456 | $C_6H_5$ |
| A.457 | 2-Cl—$C_6H_4$ |
| A.458 | 3-Cl—$C_6H_4$ |
| A.459 | 4-Cl—$C_6H_4$ |
| A.460 | 2,3-$Cl_2$—$C_6H_3$ |
| A.461 | 2,4-$Cl_2$—$C_6H_3$ |
| A.462 | 2,5-$Cl_2$—$C_6H_3$ |
| A.463 | 3,4-$Cl_2$—$C_6H_3$ |
| A.464 | 3,5-$Cl_2$—$C_6H_3$ |
| A.465 | 4-CN—$C_6H_4$ |
| A.466 | 2-$NO_2$—$C_6H_4$ |
| A.467 | 3-$NO_2$—$C_6H_4$ |
| A.468 | 4-$NO_2$—$C_6H_4$ |
| A.469 | 2,4-$(NO_2)_2$—$C_6H_3$ |
| A.470 | 2-$CH_3$—$C_6H_4$ |
| A.471 | 3-$CH_3$—$C_6H_4$ |
| A.472 | 4-$CH_3$—$C_6H_4$ |
| A.473 | 2,3-$(CH_3)_2$—$C_6H_3$ |
| A.474 | 2,4-$(CH_3)_2$—$C_6H_3$ |
| A.475 | 2,5-$(CH_3)_2$—$C_6H_3$ |
| A.476 | 2,6-$(CH_3)_2$—$C_6H_3$ |
| A.477 | 2-$C_6H_5$—$C_6H_4$ |
| A.478 | 3-$C_6H_5$—$C_6H_4$ |
| A.479 | 4-$C_6H_5$—$C_6H_4$ |
| A.480 | 3-$OCH_3$—$C_6H_4$ |
| A.481 | 4-$OCH_3$—$C_6H_4$ |
| A.482 | 3-acetyl-$C_6H_4$ |
| A.483 | 4-acetyl-$C_6H_4$ |
| A.484 | 3-methoxycarbonyl-$C_6H_4$ |
| A.485 | 4-methoxycarbonyl-$C_6H_4$ |
| A.486 | 3-$CF_3$—$C_6H_4$ |
| A.487 | 4-$CF_3$—$C_6H_4$ |
| A.488 | 2-naphthyl |
| A.489 | 6-chloropyridazin-3-yl |
| A.490 | 5-chloropyrazin-2-yl |
| A.491 | quinolin-2-yl |
| A.492 | 2,5-dimethylpyrazin-3-yl |
| A.493 | pyrazin-2-yl |
| A.494 | 3-chloropyrid-2-yl |
| A.495 | 6-chloropyrid-2-yl |
| A.496 | 4-trifluoromethyl, 6-chloropyrid-2-yl |
| A.497 | 4-trifluoromethylpyrid-2-yl |
| A.498 | 6-trifluoromethylpyrid-2-yl |
| A.499 | 6-methoxypyrid-2-yl |
| A.500 | 5-chloropyrid-2-yl |
| A.501 | pyrid-2-yl |
| A.502 | benzothiazol-2-yl |
| A.503 | 7-chloroquinolin-4-yl |
| A.504 | 3-nitropyrid-2-yl |
| A.505 | pyrrol-3-yl |
| A.506 | pyrrol-2-yl |
| A.507 | 2,6-dioctylpyrid-4-yl |
| A.508 | 5-nitropyrid-2-yl |
| A.509 | pyrid-4-yl |
| A.510 | pyrid-3-yl |
| A.511 | pyrimidin-2-yl |
| A.512 | pyrimidin-4-yl |
| A.513 | quinazolin-4-yl |
| A.514 | 6-chloropyrimidin-4-yl |
| A.515 | 6-methoxypyrimidin-4-yl |
| A.516 | 2 5,6-trichloropyrimidin-4-yl |
| A.517 | 2,6-dimethylpyrimidin-4-yl |
| A.518 | 2-methyl, 6-chloropyrimidin-4-yl |
| A.519 | 2-methyl, 6-ethoxypyrimidin-4-yl |
| A.520 | 4,5,6-trichloropyrimidin-2-yl |
| A.521 | 4,6-dimethoxypyrimidin-2-yl |
| A.522 | 4,6-dimethylpyrimidin-2-yl |
| A.523 | 4, 6-dichloropyrimidin-2-yl |
| A.524 | 4-methyl, 6-methoxypyrimidin-2-yl |
| A.525 | 4-chloro, 6-methoxypyrimidin-2-yl |
| A.526 | 6-chloroquinoxalin-2-yl |
| A.527 | 3,6-dichloro-1,2,4-triazin-5-yl |
| A.528 | 4-methoxy-1,3,5-triazin-2-yl |
| A.529 | 4-ethoxy-1,3,5-triazin-2-yl |
| A.530 | 4,6-dichloro-1,3,5-triazin-2-yl |
| A.531 | 4-ethoxy, 6-chloro-1,3,5-triazin-2-yl |
| A.532 | isoxazol-3-yl |
| A.533 | thien-2-yl |
| A.534 | fur-2-yl |
| A.535 | thiatriazol-5-yl |
| A.536 | (E)-1-chloropropen-3-yl |
| A.537 | (E)-4-(4'-chlorophenyl)but-2-en-1-yl |

TABLE A-continued

| No. | R¹ |
|---|---|
| A.538 | propyn-3-yl |
| A.539 | methylcarbonyl |
| A.540 | ethylcarbonyl |
| A.541 | n-propylcarbonyl |
| A.542 | i-propylcarbonyl |
| A.543 | n-butylcarbonyl |
| A.544 | s-butylcarbonyl |
| A.545 | i-butylcarbonyl |
| A.546 | t-butylcarbonyl |
| A.547 | n-pentylcarbonyl |
| A.548 | i-pentylcarbonyl |
| A.549 | neo-pentylcarbonyl |
| A.550 | n-hexylcarbonyl |
| A.551 | n-octylcarbonyl |
| A.552 | 1-propenylcarbonyl |
| A.553 | 2-penten-1-ylcarbonyl |
| A.554 | 2,5-heptadien-1-ylcarbonyl |
| A.555 | benzoyl |
| A.556 | 2-chlorobenzoyl |
| A.557 | 3-chlorobenzoyl |
| A.558 | 4-chlorobenzoyl |
| A.559 | 2-cyanobenzoyl |
| A.560 | 3-cyanobenzoyl |
| A.561 | 4-cyanobenzoyl |
| A.562 | 4-methoxybenzoyl |
| A.563 | 2-pyridylcarbonyl |
| A.564 | 3-pyridylcarbonyl |
| A.565 | 4-pyridylcarbonyl |
| A.566 | 2-pyrimidinylcarbonyl |
| A.567 | 2-oxazolylcarbonyl |
| A.568 | 4-methylisoxazol-5-ylcarbonyl |
| A.569 | methylsulfonyl |
| A.570 | ethylsulfonyl |
| A.571 | n-propylsulfonyl |
| A.572 | i-propylsulfonyl |
| A.573 | n-butylsulfonyl |
| A.574 | t-butylsulfonyl |
| A.575 | n-pentylsulfonyl |
| A.576 | neo-pentylsulfonyl |
| A.577 | n-hexylsulfonyl |
| A.578 | n-octylsulfonyl |
| A.579 | phenylsulfonyl |
| A.580 | 2-chlorophenylsulfonyl |
| A.581 | 3-chlorophenylsulfonyl |
| A.582 | 4-chlorophenylsulfonyl |
| A.583 | 2-cyanophenylsulfonyl |
| A.584 | 3-cyanophenylsulfonyl |
| A.585 | 4-cyanophenylsulfonyl |
| A.586 | 2-pyridylsulfonyl |
| A.587 | 3-pyridylsulfonyl |
| A.588 | 4-pyridylsulfonyl |
| A.589 | 2-pyrimidinylsulfonyl |
| A.590 | 4-oxazolylsulfonyl |
| A.591 | 5-chlorothiazol-2-ylsulfonyl |
| A.592 | 2-t-$C_4H_9$—$C_6H_4$—$CH_2$ |
| A.593 | 3-t-$C_4H_9$—$C_6H_4$—$CH_2$ |
| A.594 | 4-t-$C_4H_9$—$C_6H_4$—$CH_2$ |
| A.595 | 2-(4'-chlorothiazol-2'-yloxy)eth-1-yl |
| A.596 | 2-(1'-methylpyrazol-4'-yloxy)eth-1-yl |
| A.597 | 4-Br—$C_6H_4$ |
| A.598 | 3,5-$(CH_3)_2$—$C_6H_3$ |
| A.599 | 4-$C_2H_5$—$C_6H_4$ |
| A.600 | 3-dimethylaminocarbonyl-$C_6H_4$ |
| A.601 | 4-dimethylaminocarbonyl-$C_6H_4$ |
| A.602 | 2-hydroxyprop-1-yl |
| A.603 | 6-hydroxy-2-methylpyrimidin-4-ylmethyl |
| A.604 | [6-OH,2-CH$(CH_3)_2$-pyrimidin-4-yl]-$CH_2$ |
| A.605 | [6-OH,2-CH$(CH_2)_2$-pyrimidin-4-yl]-$CH_2$ |
| A.606 | 5-(2'-furan)pent-1-yl |
| A.607 | 5-(2'-N-methylpyrrol)pent-1-yl |
| A.608 | [2-(4-Cl—$C_6H_4$)-oxazol-4-yl]-$CH_2$ |
| A.609 | 3-$CF_3$-pyridin-2-yl |
| A.610 | 5-$CF_3$-pyridin-2-yl |
| A.611 | 6-(2'-thienyl)hex-1-yl |
| A.612 | H |

The compounds I are suitable as fungicides.

The compounds I are distinguished by an outstanding activity against a broad spectrum of phytopathogenic fungi, in particular from the classes of the Ascomycetes, Phycomycetes and Basidiomycetes. Some of them act systemically and can be employed in crop protection as foliar- and soil-acting fungicides.

They are especially important for controlling a large number of fungi on a variety of crop plants such as wheat, rye, barley, oats, rice, corn, grass, cotton, soya beans, coffee, sugar cane, grapevines, fruit species, ornamentals and vegetables such as cucumbers, beans and cucurbits, and on the seeds of these plants.

Specifically, they are suitable for controlling the following plant diseases: *Erysiphe graminis* (powdery mildew) in cereals, *Erysiphe cichoracearum* and *Sphaerotheca fuliginea* on cucurbits, *Podosphaera leucotricha* on apples, Uncinula necator on grapevines, Puccinia species on cereals, Rhizoctonia species on cotton, rice and lawns, Ustilago species on cereals and sugar cane, *Venturia inaequalis* (scab) on apples, Helminthosporium species on cereals, *Septoria nodorum* on wheat, *Botrytis cinerea* (gray mold) on strawberries, vegetables and ornamentals, grapevines, *Cercospora arachidicola* on peanuts, *Pseudocercosporella herpotrichoides* on wheat, barley, *Pyricularia oryzae* on rice, *Phytophthora infestans* on potatoes and tomatoes, Fusarium and Verticillium species on a variety of plants, Plasmopara viticola on grapevines, Pseudoperonospora species in apples and cucumbers, Alternaria species on vegetables and fruit.

Moreover, the compounds I are suitable for controlling harmful fungi in the protection of materials (eg. wood, paper, fibers or fabrics) and in the protection of stored products.

The compounds I are applied by treating the fungi, or the plants, seeds, materials or the soil to be protected against fungal infection, with a fungicidally active amount of the active ingredients. Application is effected before or after infection of the materials, plants or seeds by the fungi.

They can be converted into the customary formulations, such as solutions, emulsions, suspensions, dusts, powders, pastes and granules. The use form depends on the intended purpose; in any case, it should guarantee fine and uniform distribution of the compound according to the invention. The formulations are prepared in a known manner, eg. by extending the active ingredient with solvents and/or carriers, if desired using emulsifiers and dispersants, it also being possible to use other organic solvents as auxiliary solvents if water is used as the diluent. Suitable auxiliaries are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly-disperse silica, silicates); emulsifiers such as non-ionic and anionic emulsifiers (eg. polyoxyethylene fatty alcohol ethers, alkylsulfonates and arylsulfonates) and dispersants such as lignin-sulfite waste liquors and methylcellulose.

In general, the fungicidal compositions comprise from 0.1 to 95, preferably from 0.5 to 90, % by weight of active ingredient.

When used in crop protection, the rates of application are from 0.01 to 2.0 kg of active ingredient per ha, depending on the nature of the desired effect.

In the treatment of seed, amounts of active ingredient of from 0.001 to 0.1 g, preferably 0.01 to 0.05 g, are generally required per kilogram of seed.

When used in the protection of materials or stored products, the rate of application of active ingredient depends on the nature of the field of application and on the desired effect. Usual rates of application in the protection of materials are, for example, 0.001 g to 2 kg, preferably 0.005 g to 1 kg, of active ingredient per cubic meter of material treated.

In the use form as fungicides, the agents according to the invention may also be present together with other active ingredients, eg. with herbicides, insecticides, growth regulators, fungicides, or else with fertilizers.

A mixture with fungicides frequently results in a widened fungicidal spectrum of action.

The following list of fungicides together with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N'-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl) disulfide; nitro derivatives, such as dinitro(1-methylheptyl)phenyl crotonate, 2-sec-butyl-4,6-dinitrophenyl 3,3-dimethylacrylate, 2-sec-butyl-4,6-dinitrophenyl isopropyl carbonate, di-isopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl) benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline and its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diylbis(2,2,2-trichloroethyl)formamide, 1-(3,4-dichloroanilino)-1-formylamino-2,2,2-trichloroethane, 2,6-dimethyl-N-tridecylmorpholine and its salts, 2,6-dimethyl-N-cyclododecylmorpholine and its salts, N-[3-(p-tert-butylphenyl)-2-methylpropyl]-cis-2,6-dimethyl-morpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, $\alpha$-(2-chlorophenyl)-$\alpha$-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, and a variety of fungicides, such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)-alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-[3,5-dichlorophenyl-(5-methyl-5-methoxymethyl]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)-pentyl]-1H-1,2,4-triazole, 2,4-difluoro-$\alpha$-(1H-1,2,4-triazolyl-1-methyl)-benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole.

strobilurins such as methyl E-methoxyimino-[$\alpha$-(o-tolyloxy)-o-tolyl]acetate, methyl E-2-{2-[6-(2-cyanophenoxy)-pyrimidin-4-yloxy]phenyl}-3-methoxyacrylate, N-methyl-E-methoxyimino-[$\alpha$-(2-phenoxyphenyl)]acetamide, N-methyl-E-methoxyimino-[$\alpha$-(2,5-dimethylphenoxy)-o-tolyl]-acetamide, anilinopyrimidines such as N-(4,6-dimethylpyrimidin-2-yl)aniline, N-[4-methyl-6-(1-propynyl)-pyrimidin-2-yl]aniline, N-(4-methyl-6-cyclopropylpyrimidin-2-yl) aniline, phenylpyrroles such as 4-(2,2-difluoro-1,3-benzodioxol-4-yl)-pyrrole-3-carbonitrile, cinnamamides such as 3-(4-chlorophenyl)-3-(3,4-dimethoxyphenyl)-acryloylmorpholine.

The compounds of the formula I are furthermore suitable for efficiently controlling pests from the classes of the insects, arachnids and nematodes. They can be employed as pesticides in crop protection and in the hygiene, stored-products and veterinary sectors.

The harmful insects include, from the order of the lepidopterans (Lepidoptera), for example, *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia* botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis.

From the order of the beetles (Coleoptera), for example, Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, diabrotica longicornis, diabrotica 12-punctata, diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus, Sitophilus granaria.

From the order of the dipterans (Diptera), for example, Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea, Tipula paludosa.

From the order of the thrips (Thysanoptera), for example, Frankliniella fusca, Frankliniella occidentalis, Frankliniella tritici, Scirtothrips citri, Thrips oryzae, Thrips palmi, Thrips tabaci.

From the order of the hymenopterans (Hymenoptera), for example, Athalia rosae, Atta cephalotes, Atta sexdens, Atta texana, Hoplocampa minuta, Hoplocampa testudinea, Monomorium pharaonis, Solenopsis geminata, Solenopsis invicta.

From the order of the heteropterans (Heteroptera), for example, Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor.

From the order of the homopterans (Homoptera), for example, Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbia , Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum, Viteus vitifolii.

From the order of the termites (Isoptera), for example, Calotermes flavicollis, Leucotermes flavipes, Reticulitermes lucifugus, Termes natalensis.

From the order of the orthopterans (Orthoptera), for example, Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.

From the class of the Arachnoidea, for example, arachnids (Acarina), such as Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius, Tetranychus urticae.

From the class of the Nematodes, for example, root-knot nematodes, eg. Meloidogyne hapla, Meloidogyne incognita, Meloidogyne javanica, cyst-forming nematodes, eg. Globodera rostochiensis, Heterodera avenae, Heterodera glycines, Heterodera schachtii, Heterodera trifolii, stem eelworms and foliar nematodes, eg. Belonolaimus longicaudatus, ditylenchus destructor, ditylenchus dipsaci, Heliocotylenchus multicinctus, Longidorus elongatus, Radopholus similis, Rotylenchus robustus, trichodorus primitivus, Tylenchorhynchus claytoni, Tylenchorhynchus dubius, Pratylenchus neglectus, Pratylenchus penetrans, Pratylenchus curvitatus, Pratylenchus goodeyi.

The active ingredients can be used as such, in the form of their formulations or the use forms prepared therefrom, eg. in the form of directly sprayable solutions, powders, suspensions or dispersions, emulsions, oil dispersions, pastes, dusts, materials for spreading, or granules, by means of spraying, atomizing, dusting, spreading or pouring. The use forms depend entirely on the intended purposes; in any case, they should guarantee the finest possible distribution of the active ingredient according to the invention.

The active ingredient concentrations in the ready-to-use preprations can be varied within substantial ranges.

In general, they are between 0.0001 and 10%, preferably between 0.01 and 1%.

The active ingredients can also be used very successfully in the ultra-low volume method (ULV), it being possible to apply formulations comprising over 95% by weight of active ingredient, or even the active ingredient without additives.

The rate of application of active ingredient for controlling pests is from 0.1 to 2.0, preferably 0.2 to 1.0, kg/ha under field conditions.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone and water.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of wetting agent, tackifier, dispersant or emulsifier. Alternatively, it is possible to prepare concentrates which are suitable for dilution with water and which are composed of active ingredient, wetting agent, tackifier, dispersant or emulsifier and, if applicable, solvents or oil.

Suitable surfactants are alkali metal, alkaline earth metal and ammonium salts of lignosulfonic acid, naphthalenesulfonic acid, phenolsulfonic acid, dibutylnaphthalenesulfonic acid; alkylarylsulfonates, alkyl sulfates, alkylsulfonates, fatty alcohol sulfates and fatty acids and also their alkali metal and alkaline earth metal salts, salts of sulfated fatty alcohol glycol ether, condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Powders, materials for spreading and dusts can be prepared by mixing or concomitantly grinding the active ingredients together with a solid carrier.

In general, the formulations comprise between 0.01 and 95% by weight, preferably between 0.1 and 90% by weight, of the active ingredient. The active ingredients are employed in a purity of from 90% to 100%, preferably 95% to 100% (according to NMR spectrum).

EXAMPLES OF FORMULATIONS ARE

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which had been sprayed onto the surface of the silica gel. This gives a formulation of the active ingredient with good adhesion properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide to 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-α-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

Granules, eg. coated granules, impregnated granules and homogeneous granules, can be prepared by binding the active ingredients to solid carriers. Examples of solid carriers are mineral earths such as silicas, silica gels, silcates, talc, kaolin, attaclay, limestone, lime, chalk, bole, loess, clay, dolomite, diatomaceous earth, calcium sulfate, magnesium sulfate, magnesium oxide, ground synthetic materials, fertilizers, eg. ammonium sulfate, ammonium phosphate, ammonium nitrate, ureas, and products of vegetable origin, such as cereal meal, tree bark meal, wood meal and nutshell meal, cellulose powders, and other solid carriers.

Various types of oils, and herbicides, fungicides, other pesticides, or bactericides, may be added to the active ingredients, if desired also only just prior to use (tank mix). These agents can be admixed with the agents according to the invention in a weight ratio of from 1:10 to 10:1.

Synthesis Examples

The protocols shown in the synthesis examples below were used for obtaining other compounds I by suitably altering the starting materials. The resulting compounds together with physical data are listed in the tables which follow.

Example 1

Methyl E-2-methoxyimino-2-[(2-[6-(methoximinoeth-1'-yl)-pyridin-2-yl)]oxymethyl)phenyl]acetate (compound No. 2)

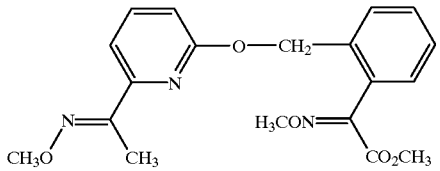

Stage 1: 2-ethoxy-6-bromopyridine:

20 g of 2,6-dibromopyridine were introduced into 130 ml of dimethylformamide. 6.4 g of sodium ethanolate were added. The reaction mixture was stirred for two hours at 55° C. After the reaction mixture had cooled to room temperature, it was poured into approximately 900 ml of half-concentrated aqueous ammonium chloride solution. The mixture was extracted 4 times using methyl tert-butyl ether. The combined organic phases were washed 3 times with half-concentrated aqueous sodium hydrogen carbonate solution and subsequently dried over sodium sulfate. After the solvent had been stripped off, there remained 16.8 g of 2-ethoxy-6-bromopyridine, which was employed in the subsequent stage without further purification.

Stage 2: 2-ethoxy-6-acetylpyridine:

16.8 g of 2-ethoxy-6-bromopyridine were introduced into 220 ml of tetrahydrofuran at −75° C. 54.4 ml of n-butyllithium (1.6-molar solution in n-hexane) were added dropwise at this temperature. Stirring was continued for two hours at −75° C., and 7.6 g of N,N-dimethylacetamide were added dropwise at this temperature. The mixture was stirred for a further hour at −75° C. and then warmed to −10° C., and first approximately 170 ml of 20 percent strength aqueous ammonium chloride solution and then 200 ml of water were added dropwise at this temperature. The mixture was extracted 3 times using methyl tert-butyl ether. The combined organic phases were washed 3 times with water and subsequently dried over sodium sulfate. After the solvent had been stripped off, the residue which remained was chromatographed on silica gel using cyclohexane/methyl tert-butyl ether 8:1. This gave 5.5 g of 2-ethoxy-6-acetylpyridine as a colorless solid (m.p.: 36–37° C).

Stage 3: 2-hydroxy-6-acetylpyridine:

48.5 g of 2-ethoxy-6-acetylpyridine were introduced into 145 ml of hydrogen bromide solution (30 percent strength solution in glacial acetic acid) and the mixture was heated to 95° C. A further 176 ml of hydrogen bromide solution (30% strength solution in glacial acetic acid) were added dropwise at this temperature. The mixture was stirred for 3 hours at 95° C. and then cooled to room temperature. It was poured into ice-water and neutralized to pH 7 using 50 percent strength aqueous sodium hydroxide solution. The mixture was subsequently extracted 3 times with methyl tert-butyl ether. The aqueous phase was concentrated. The residue which remained was stirred 4 times with acetone. After the combined acetone phases had been concentrated, there remained 38.5 g of 2-hydroxy-6-acetylpyridine as a colorless solid (m.p.: 115–117 C).

Stage 4: 2-hydroxy-6-(methoximinoeth-1'-yl)pyridine:

4.1 g of 2-hydroxy-6-acetylpyridine and 3.8 g of methoxyamine hydrochloride were introduced into 60 ml of methanol, and the mixture was brought to pH 5 using 5% strength aqueous sodium hydroxide solution. It was stirred for three hours at 60° C. and then for 14 hours at room temperature. The reaction mixture was concentrated. The crude product which remained was chromatographed on silica gel using ethyl acetate. This gave 4 g of 2-hydroxy-6-(methoximinoeth-1'-yl)pyridine as a colorless solid (m.p.: 102–103° C.).

Stage 5: Title compound:

4 g of 2-hydroxy-6-(methoximinoeth-1'-yl)pyridine, 6.9 g of methyl E-2-methoxyimino-2-[2-(bromomethyl)phenyl] acetate and 5 g of potassium carbonate were stirred in 80 ml of dimethylformamide for 2 hours at 60° C. and then for 14 hours at room temperature. The reaction mixture was concentrated. The residue which remained was taken up in methyl tert-butyl ether. It was washed with water, dried over sodium sulfate and reconcentrated. The crude product was dissolved in 20 ml of hot isopropanol. When the solution cooled to room temperature, crystallization started. 40 ml of n-hexane were added. The product which had precipitated was filtered off and dried. This gave 6.4 g of the title compound as a colorless solid (m.p.: 100–101° C.).

Example 2

N-methyl-E-2-methoxyimino-2-[(2-[6-(methoximinoeth-1'-yl)-pyridin-2-yl)]oxymethyl)phenyl]acetamide (compound No. 1)

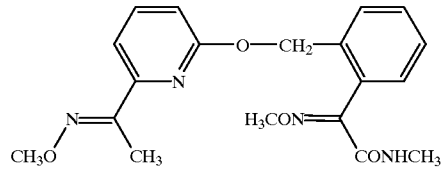

5.2 g of the methyl ester (title compound of Example 1) were dissolved in 50 ml of tetrahydrofuran, and 10.9 g of 40% strength aqueous methylamine solution were added. The mixture was stirred for 5 hours at 60° C. After the batch had cooled, it was concentrated. The residue which remained was taken up in 100 ml of methyl tert-butyl ether. The organic phase was washed with water, dried over sodium sulfate and subsequently evaporated to dryness. There remained 4.9 g of the title compound as a colorless solid (m.p.: 63–64° C.).

Route B:

Stage 1: 2-bromo-6-acetylpyridine:

29.7 g of 2,6-dibromopyridine were reacted with 86.1 ml of n-butyllithium (1.6-molar solution in n-hexane) and 12 g of N,N-dimethylacetamide in 300 ml of diethyl ether as described in the literature [J. Organomet. Chem. 56 (1973), 53–66; Chem. Ber. 125 (1992), 1169–1190] to give 2-bromo-6-acetylpyridine.

Stage 2: 2-bromo-6-(methoximinoeth-1'-yl)-pyridine:

2 g of 2-bromo-6-acetylpyridine and 1.25 g of methoxyamine hydrochloride were stirred in 20 ml of pyridine for 14 hours at room temperature (approximately 25° C.). The reaction mixture was taken up in methyl tert-butyl ether. The organic phase was first washed with 10 percent strength hydrochloric acid and then with water, dried over sodium sulfate and subsequently evaporated to dryness. There remained 2.3 g of 2-bromo-6-(methoximinoeth-1'-yl) pyridine, which was employed in stage 3 without further purification.

Stage 3: Title compound:

A solution of 1.1 g of N-methyl-E-2-methoxyimino-2-[2-(hydroxymethyl)phenyl]acetamide in 10 ml of dimethylformamide was added dropwise at room temperature to 0.14 g of sodium hydride in 5 ml of dimethylformamide. Stirring was continued for 10 minutes in an ultrasonic bath. A solution of 1.15 g of 2-bromo-6-(methoximinoeth-1'-yl) pyridine in 12 ml dimethylformamide was subsequently added dropwise. The mixture was stirred for four hours at 120° C. After the batch had cooled, it was concentrated. The residue which remained was taken up in methyl tert-butyl ether. The organic phase was washed with water, dried over sodium sulfate and subsequently evaporated to dryness. The residue which remained was chromatographed on silica gel using cyclohexane/methyl tert-butyl ether 1:2. This gave 0.35 g of the title compound as a colorless solid (m.p.: 63–64° C.).

Example 3

N-methyl-E-2-methoxyimino-2-[(2-[3-methyl-5-(ethoximinoeth-1'-yl)-pyridin-2-yl)]oxymethyl) phenyl]-acetamide (compound No. 17)

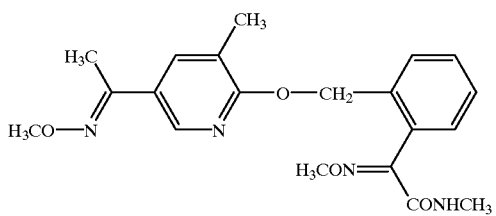

Stage 1: 2-bromo-3-methyl-5-acetylpyridine:

12.2 g of 2-bromo-3-methyl-5-iodopyridine [prepared as described in J. Org. Chem. 60 (1995), 5358] were introduced into 120 ml of diethyl ether. 28.1 ml of n-butyllithium (1.6-molar solution in n-hexane) were added dropwise at –75° C. The mixture was stirred for one hour at –75° C. and then for 30 minutes at –40° C. 3.9 g of dimethylacetamide were added dropwise at –75° C. The mixture was stirred for 15 minutes at –75° C. and then for 2 hours at –40° C. The reaction mixture was then warmed to –10° C., and approximately 100 ml of a 20% strength aqueous ammonium chloride solution were added. The organic phase was separated off. The aqueous phase was extracted 3 times with methyl tert-butyl ether. The combined organic phases were washed 3 times with water and subsequently dried over sodium sulfate and concentrated. The residue which remained was chromatographed on silica gel using cyclohexane/methyl tert-butyl ether 3:1. This gave 5.3 g of 2-bromo-3-methyl-5-acetylpyridine as a colorless solid (m.p.: 114–115° C.).

Stage 2: N-methyl-E-2-methoxyimino-2-[ (2-[3-methyl-5-acetylpyridin-2-yl)]oxymethyl)phenyl]acetamide:

A solution of 3.1 g of N-methyl- E-2-methoxyimino-2-[2-(hydroxymethyl)phenyl]acetamide in 25 ml of dimethylformamide was added dropwise at room temperature to 0.39 g of sodium hydride in 5 ml of dimethylformamide. Stirring was continued for 15 minutes in an ultrasonic bath. A solution of 3 g of 2-bromo-3-methyl-5-acetylpyridine in 40 ml of dimethylformamide was subsequently added dropwise. The mixture was stirred for three hours at 60° C. After the batch had cooled, it was concentrated. The residue which remained was taken up in ethyl acetate. The organic phase was washed with water, dried over sodium sulfate and subsequently evaporated to dryness. The residue which remained was chromatographed on silica gel using cyclohexane/ethyl acetate 1:1. This gave 2.6 g of N-methyl-E-2-methoxyimino-2-[(2-[3-methyl-5-acetylpyridin-2-yl)]-oxymethyl)phenyl]acetamide as a colorless solid (m.p.: 97–99° C.).

Stage 3: Title compound:

1 g of N-methyl- E-2-methoxyimino-2-[(2-[3-methyl-5-acetylpyridin-2-yl)]oxymethyl)phenyl]acetamide of stage 2 and 0.57 g of ethoxyamine hydrochloride were -introduced into 10 ml of methanol. The reaction mixture was brought to pH 5 using 10% strength hydrochloric acid. The mixture was stirred for two hours at 60° C. and for a further 12 hours at room temperature. The reaction mixture was concentrated. The residue which remained was taken up in methyl tert-butyl ether, washed with water and reconcentrated. The crude product was dissolved in a small amount of methyl tert-butyl ether. The product was precipitated as crystals by adding n-pentane. This gave 0.8 g of the title compound as a colorless solid (m.p.: 97–99° C.).

Example 4

N-methyl-E-2-methoxyimino-2-[(2-[3-chloro-5-(prop-1"-en-3"-oximinoeth-1'-yl)pyridin-2-yl)] oxymethyl)phenyl]acetamide (compound No. 14)

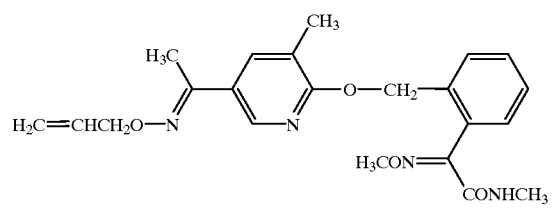

Stage 1: 2,3-dichloro-5-acetylpyridine:

2,3-Dichloro-5-acetylpyridine was prepared as described in the literature (cf. DE-A 38 38 243, EP-A 446 872; Tetrahedron 48, 22 (1992) 9233 et seq.).

Stage 2: N-methyl-E-2-methoxyimino-2-[(2-[3-chloro-5-acetylpyridin-2-yl)]oxymethyl)phenyl]acetamide A solution of 22.2 g of N-methyl-E-2-methoxyimino-2-[2-(hydroxymethyl)phenyl]acetamide in 200 ml of dimethylformamide was added dropwise at room temperature to 2.64 g of sodium hydride in 50 ml of dimethylformamide. Stirring was continued for 20 minutes in an ultrasonic bath. A solution of 19 g of 2,3-dichloro-5-acetylpyridine in 150 ml of dimethylformamide was subsequently added dropwise. The mixture was stirred for 14 hours at room temperature and then for five hours at 50° C. After the reaction mixture had cooled, it was taken up in 1.5 l of water and extracted 3 times with methyl tert-butyl ether. The combined organic phases were washed with water, dried over sodium sulfate and concentrated. The residue which remained was recrystallized from isopropanol. This gave 15.5 g of N-methyl-E-2-methoxyimino-2-[(2-[3-chloro-5-acetylpyridin-2-yl)] oxymethyl)phenyl]acetamide as a colorless solid (m.p.: 133–134° C.).

Stage 3: Title compound:

1.5 g of N-methyl-E-2-methoxyimino-2-[(2-[3-chloro-5-acetylpyridin-2-yl)]oxymethyl)phenyl]acetamide of stage 2 and 0.66 g of prop-1-en-3-oxyamine hydrochloride were stirred for 12 hours in 0.48 g of pyridine. The reaction mixture was concentrated. The residue which remained was taken up in methyl tert-butyl ether, ashed with water, dried over sodium sulfate and reconcentrated. The crude product was recrystallized from n-hexane/ethyl acetate. This gave 1.25 g of the title compound as a colorless solid (m.p.: 77–79° C.).

Example 5

N-methyl-E-2-methoxyimino-2-[(2-[5-(prop-1"-yn-3"-oximinoeth-1'-yl)pyridin-2-yl)]oxymethyl)phenyl]-acetamide (compound No. 28)

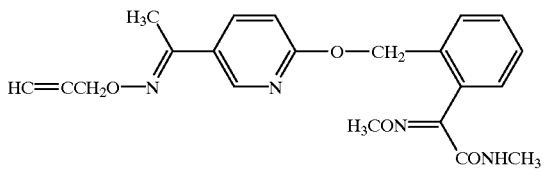

Stage 1: 2-chloro-5-acetylpyridine, or 2-bromo-5-acetylpyridine:

2-Chloro-5-acetylpyridine, or 2-bromo-5-acetylpyridine, were prepared as described in the literature [see Chem. Ber. 125 (1992) 1169–1190; Tetrahedron 48, 22 (1992) 9233 et seq.], and it was possible for each of these to be employed in stage 2. What follows is an exemplary description of the reaction with 2-chloro-5-acetylpyridine.

Stage 2: N-methyl-E-2-methoxyimino-2-[(2-[5-acetylpyridin-2-yl)]oxymethyl)phenyl]acetamide:

A solution of 17.8 g of N-methyl-E-2-methoxyimino-2-[2-(hydroxymethyl)phenyl]acetamide in 120 ml of dimethylformamide was added dropwise to 2.22 g of sodium hydride in 20 ml of dimethylformamide at room temperature. Stirring was continued for 20 minutes at room temperature and for 90 minutes at 40° C. in an ultrasonic bath. A solution of 12.4 g of 2-chloro-5-acetylpyridine in 100 ml of dimethylformamide was subsequently added dropwise. The mixture was stirred for 3 hours at 45° C. and for a further 12 hours at room temperature. The reaction mixture was taken up in 1 l of water and extracted 3 times with methyl tert-butyl ether. The combined organic phases were washed with water, dried over sodium sulfate and concentrated. The residue which remained was recrystallized from isopropanol. This gave 16.7 g of N-methyl-E-2-methoxyimino-2-[(2-[5-acetylpyridin-2-yl)]oxymethyl)phenyl]acetamide as a colorless solid (m.p.: 132–134° C.).

Stage 3: Title compound:

1.4 g of N-methyl-E-2-methoxyimino-?-[(2-[5-acetylpyridin-2-yl)]oxymethyl)phenyl]acetamide of stage 2 in 25 ml of methanol and 0.66 g of prop-1-yn-3-oxyamine hydrochloride were stirred in 0.49 g of pyridine for 3 hours at 45° C. and for 12 hours at room temperature. The reaction mixture was concentrated. The residue which remained was taken up in methyl tert-butyl ether, washed with water, dried over sodium sulfate and reconcentrated. This gave 1.54 g of the title compound as a colorless resin.

IR [cm$^{-1}$]: 1672, 1602, 1526, 1490, 1316, 1288, 1256, 1039, 1007, 979.

Example 6

N-methyl-E-2-methoxyimino-2-[(2-[5-(benzyloximinoeth-1'-yl)pyridin-2-yl)]oxy)phenyl]acetamide (compound No. 22)

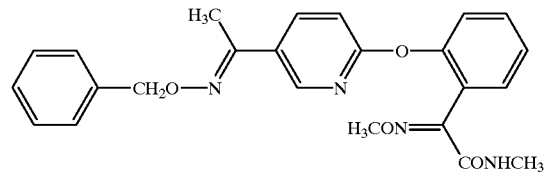

Stage 1: N-methyl-E-2-methoxyimino-2-[ (2-5-acetylpyridin-2-yl)]oxy)phenyl]acetamide:

8.9 g of 2-chloro-5-acetylpyridine, 9.9 g of N-methyl-E-2-methoxyimino-2-[2-(hydroxy)phenyl]acetamide and 9.9 g of potassium carbonate were stirred in 120 ml of dimethylformamide for 12 hours at 70° C. The reaction mixture was taken up in 0.5 l of water and extracted 3 times with methyl tert-butyl ether. The combined organic phases were washed with water, dried over sodium sulfate and concentrated. The residue which remained was chromatographed on silica gel using cyclohexane/ethyl acetate 1:2. This gave 3.5 g of N-methyl-E-2-methoxyimino-2-[(2-[5-acetylpyridin-2-yl)]oxy)phenyl]acetamide as a colorless solid (mp.: 116–117° C.).

Stage 2: Title compound:

A reaction mixture of 0.7 g of N-methyl-E-2-methoxyimino-2-[(2-[5-acetylpyridin-2-yl)]oxy)phenyl]acetamide (of stage 1) in 15 ml of methanol and 0.34 g of benzyloxyamine was brought to pH 5 using 10% strength hydrochloric acid. The mixture was stirred for 3 hours at 45° C. and for 12 hours at room temperature. The reaction mixture was concentrated. The residue which remained was taken up in methyl tert-butyl ether, washed with water, dried over sodium sulfate and reconcentrated. This gave 0.8 g of the title compound as a colorless solid (m.p.: 88–89° C.).

TABLE

I

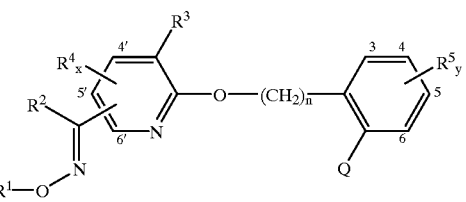

| No. | $R^1$ | $R^2$ | Pos.# | $R^3$ | $R^4_x$ | n | $R^5_y$ | Q | Phys. Data* |
|---|---|---|---|---|---|---|---|---|---|
| I.1 | $CH_3$ | $CH_3$ | 6' | H | H | 1 | H | $C(=NOCH_3)—CONHCH_3$ | 63–64 |
| I.2 | $CH_3$ | $CH_3$ | 6' | H | H | 1 | H | $C(=NOCH_3)—CO_2CH_3$ | 100–101 |
| I.3 | $CH_2CH_3$ | $CH_3$ | 6' | H | H | 1 | H | $C(=NOCH_3)—CONHCH_3$ | 68–70 |
| I.4 | $CH_2CH_3$ | $CH_3$ | 6' | H | H | 1 | H | $C(=NOCH_3)—CO_2CH_3$ | 90–92 |
| I.5 | $CH_3$ | $C_6H_5$ | 6' | H | H | 1 | H | $C(=NOCH_3)—CONHCH_3$ | 1674, 1573, 1527, 1444, 1340, 1281, 1266, 1036, 1018, 980 |

TABLE-continued $$\text{Structure I: } R^1\text{—O—N=C(R}^2\text{)—[pyridine with R}^3\text{ at 4', R}^4_x\text{ at 5']—O—(CH}_2)_n\text{—[phenyl with R}^5_y\text{ and Q]}$$

| No. | $R^1$ | $R^2$ | Pos.# | $R^3$ | $R^4x$ | n | $R^5y$ | Q | Phys. Data* |
|---|---|---|---|---|---|---|---|---|---|
| I.6 | $CH_3$ | $CH_3$ | 5' | H | H | 1 | H | $C(=NOCH_3)$—$CONHCH_3$ | 93–95 |
| I.7 | $CH_2CH_3$ | $CH_3$ | 5' | H | H | 1 | H | $C(=NOCH_3)$—$CONHCH_3$ | 1670, 1601, 1526, 1496, 1316, 1287, 1255, 1049, 1001, 979 |
| I.8 | $CH_3$ | $CH_3$ | 5' | Cl | H | 1 | H | $C(=NOCH_3)$—$CONHCH_3$ | 144–146 |
| I.9 | $CH_2CH_3$ | $CH_3$ | 5' | Cl | H | 1 | H | $C(=NOCH_3)$—$CONHCH_3$ | 108–110 |
| I.10 | $CH_2CH_2CH_3$ | $CH_3$ | 5' | Cl | H | 1 | H | $C(=NOCH_3)$—$CONHCH_3$ | 88–89 |
| I.11 | $CH(CH_3)_2$ | $CH_3$ | 5' | Cl | H | 1 | H | $C(=NOCH_3)$—$CONHCH_3$ | 85–87 |
| I.12 | $(CH_2)_3CH_3$ | $CH_3$ | 5' | Cl | H | 1 | H | $C(=NOCH_3)$—$CONHCH_3$ | 77–78 |
| I.13 | $CH_2CH(CH_3)_2$ | $CH_3$ | 5' | Cl | H | 1 | H | $C(=NOCH_3)$—$CONHCH_3$ | 97–98 |
| I.14 | $CH_2CH=CH_2$ | $CH_3$ | 5' | Cl | H | 1 | H | $C(=NOCH_3)$—$CONHCH_3$ | 77–79 |
| I.15 | $CH_2C\equiv CH$ | $CH_3$ | 5' | Cl | H | 1 | H | $C(=NOCH_3)$—$CONHCH_3$ | 105–107 |
| I.16 | $CH_3$ | $CH_3$ | 5' | $CH_3$ | H | 1 | H | $C(=NOCH_3)$—$CONHCH_3$ | 141–142 |
| I.17 | $CH_2CH_3$ | $CH_3$ | 5' | $CH_3$ | H | 1 | H | $C(=NOCH_3)$—$CONHCH_3$ | 97–99 |
| I.18 | $CH_3$ | $CH_3$ | 5' | H | H | 0 | H | $C(=NOCH_3)$—$CONHCH_3$ | 97–98 |
| I.19 | $CH_2CH_3$ | $CH_3$ | 5' | H | H | 0 | H | $C(=NOCH_3)$—$CONHCH_3$ | 1672, 1527, 1478, 1447, 1376, 1270, 1248, 1091, 1047, 980 |
| I.20 | $CH_2CH_2CH_3$ | $CH_3$ | 5' | H | H | 0 | H | $C(=NOCH_3)$—$CONHCH_3$ | 56–58 |
| I.21 | $(CH_2)_3CH_3$ | $CH_3$ | 5' | H | H | 0 | H | $C(=NOCH_3)$—$CONHCH_3$ | 56–57 |
| I.22 | $CH_2$—$C_6H_5$ | $CH_3$ | 5' | H | H | 0 | H | $C(=NOCH_3)$—$CONHCH_3$ | 88–89 |
| I.23 | $CH_2CH_2CH_3$ | $CH_3$ | 5' | H | H | 1 | H | $C(=NOCH_3)$—$CONHCH_3$ | 1671, 1601, 1526, 1496, 1317, 1287, 1255, 1038, 1004, 979 |
| I.24 | $CH(CH_3)_2$ | $CH_3$ | 5' | H | H | 1 | H | $C(=NOCH_3)$—$CONHCH_3$ | 1672, 1601, 1495, 1314, 1286, 1255, 1038, 1003, 979 |
| I.25 | $(CH_2)_3CH_3$ | $CH_3$ | 5' | H | H | 1 | H | $C(=NOCH_3)$—$CONHCH_3$ | 1672, 1601, 1526, 1496, 1316, 1287, 1255, 1038, 979 |
| I.26 | $CH_2CH(CH_3)_2$ | $CH_3$ | 5' | H | H | 1 | H | $C(=NOCH_3)$—$CONHCH_3$ | 1672, 1602, 1526, 1496, 1389, 1316, 1287, 1256, 1041, 979 |
| I.27 | $CH_2CH=CH_2$ | $CH_3$ | 5' | H | H | 1 | H | $C(=NOCH_3)$—$CONHCH_3$ | 1672, 1601, 1526, 1496, 1316, 1287, 1256, 1036, 997 |
| I.28 | $CH_2C\equiv CH$ | $CH_3$ | 5' | H | H | 1 | H | $C(=NOCH_3)$—$CONHCH_3$ | 1672, 1602, 1526, 1490, 1316, 1288, 1256, 1039, 1007, 979 |
| I.29 | $CH_3$ | $CH_3$ | 6' | H | H | 1 | H | $N(OCH_3)$—$CO_2CH_3$ | Resin |
| I.30 | $CH_3$ | $CH_3$ | 6 | H | H | 0 | H | $C(=NOCH_3)CONHCH_3$ | 1673, 1569, 1526, 1447, 1272, 1251, 1048, 980, 889 |
| I.31 | $CH_3$ | $CH_3$ | 6 | H | H | 1 | H | $C(=CHCH_3)COOCH_3$ | 1717, 1573, 1451, 1336, 1262, 1051, 1002, 876, 805, 763 |
| I.32 | $C_2H_5$ | $CH_3$ | 6 | H | H | 1 | H | $C(=CHCH_3)COOCH_3$ | 1717, 1574, 1450, 1336, 1263, 1049, 1003, 884, 805, 762 |
| I.33 | $CH_3$ | $CH_3$ | 6 | H | H | 1 | H | $C(=CHOCH_3)COOCH_3$ | 1710, 1634, 1573, 1451, 1336, 1259, 1191, 1129, 1109, 1051 |
| I.34 | $C_2H_5$ | $CH_3$ | 6 | H | H | 1 | H | $C(=CHOCH_3)COOCH_3$ | 1710, 1634, 1574, 1451, 1336, 1259, 1129, 1110, 1050, 1001 |
| I.35 | $CH_3$ | $CF_3$ | 6' | H | H | 1 | H | $C(=NOCH_3)CONHCH_3$ | 1668, 1594, 1449, 1359, 1302, 1220, 1186, 1145, 1045, 986 |
| I.36 | $CH_3$ | $CF_3$ | 5' | $CH_3$ | H | 1 | H | $C(=NOCH_3)CONHCH_3$ | 110–112 |
| I.37 | $C_2H_5$ | $CH_3$ | 6' | H | H | 0 | H | $C(=NOCH_3)CONHCH_3$ | 1.3(t,3H); 2.15(s,3H); 2.8(d,3H); 3.8(s,3H); 4.3(q,2H); 6.5(1H,br); 6.8–7.6(7H,m). |

*: m.p. [°C.]; IR [cm$^{-1}$]; $^1$H NMR [δ in ppm/TMS]
: Position of group $C(R^2) = NOR^1$ Examples of the Activity Against Harmful Fungi The fungicidal activity of the compounds of the general formula I is demonstrated by the following experiments:

The active ingredients were formulated as a 20% strength emulsion in a mixture of 70% by weight of cyclohexanone, 20% by weight of Nekanil® LN (Lutensol® AP6, wetting agent having emulsifying and dispersing action based on ethoxylated alkylphenols) and 10% by weight of Emulphor® EL (Emulan® EL, emulsifier based on ethoxylated fatty alcohols) and diluted with water to give the desired concentration.

Activity Against *Plasmopara viticola* (powdery mildew of grapevines)

Grapevines in pots (cultivar: "Müller Thurgau") were sprayed to drip point with the preparation of active ingredient (rate of application: 16 ppm). After 8 days, the plants were sprayed with a zoo spore suspension of the fungus *Plasmopara viticola* and left to stand for 5 days at 20–30° C. and high atmospheric humidity. Prior to assessment, the plants were left to stand for 16 hours at high atmospheric humidity. The evaluation was carried out visually.

In this test, the disease level of the plants which had been treated with compounds I.1, I.2, I.3, I.4, I.5, I.6, I.7, I.8, I.9, I.10, I.11, I.12, I.13, I.14, I.15, I.16, I.17, I.20, I.23, I.24, I.25, I.26, I.27, I.28, I.29, I.32, I.33 and I.34 according to the invention was 15% and less, while the untreated (control) plants had a disease level of 80%.

Activity Against *Puccinia recondita* (leaf rust of wheat)

Leaves of wheat seedlings (cultivar "Kanzler") were dusted with leaf rust (*Puccinia recondita*) spores. The treated plants were incubated for 24 hours at 20–22° C. and a relative atmospheric humidity of 90–95% and subsequently treated with the aqueous preparation of the active ingredient (rate of application: 63 ppm). After a further 8 days at 20–22° C. and a realtive atmospheric humidity of 65–70%, the xtent of the fungal development was determined. The evaluation was carried out visually.

In this test, the disease level of the plants which had been treated with compounds I.1, I.3, I.6, I.7, I.8, I.10, I.11, I.12, I.13, I.14, I.15, I.16, I.17, I.22, I.23, I.24, I.25, I.26, I.28, I.29, I.31, I.32, I.33 and I.34 according to the invention was 15% and less, while the untreated (control) plants had a disease level of 60%.

Examples of the Activity Against Animal Pests

The activity of the compounds of the general formula against animal pests was demonstrated by the following experiments:

The active ingredients were formulated a. as a 0.1% strength solution in acetone or b. as a 10% strength emulsion in a mixture of 70% by weight of cyclohexanone, 20% by weight of Nekanil® LN (Lutensol® AP6, wetting agent having emulsifying and dispersing action based on ethoxylated alkylphenols) and 10% by weight of Emulphor® EL (Emulan® EL, emulsifier based on ethoxylated fatty alcohols)

and diluted to give the desired concentration using acetone in the case of a. and water in the case of b.

After the experiments had been concluded, the lowest concentration was determined in each case at which the compounds still caused an 80 to 100% inhibition or mortality in comparison with untreated controls (limit or minimal concentration).

*Nephotettix cincticeps* (green rice leafhopper), Contact Action

Circular filters were treated with the aqueous preparation of active ingredient and subsequently populated with 5 adult leafhoppers. The mortality was assessed after 24 hours.

In this test, a limit concentration of 0.2 mg was shown by the compounds I.23, I.24, I.25, I.26, I.27 and I.28.

*Aphis fabae* (black bean aphid), Contact Action

Severely infested dwarf beans (*Vicia faba*) were treated with the aqueous preparation of the active ingredient. The mortality rate was assessed after 24 hours.

In this test, a limit concentration of 200 ppm was shown by the compounds I.7 and I.11.

*Tetranychus urticae* (greenhouse red spider mite), Contact Action

Dwarf beans, in pots, which showed the second pair of consecutive leaves were treated with aqueous preparation of active ingredient. After 24 hours, the plants were infected with the aid of severely infested leaf sections. The infection level was determined after 12 days in the greenhouse.

Limit concentrations of 200 ppm and less were shown, in this test, by the compounds I.10, I.11, I.12, I.13, I.14 and I.22.

We claim:

1. A pyridyl phenyl or pyridyl benzyl ether of the formula I

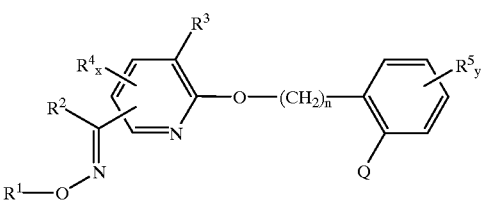

or a salt or N-oxide thereof where the substituent and indices have the following meanings:

Q is $C(CO_2CH_3)=CHCH_3-$, $C(CO_2CH_3)=CHOCH_3$, $C(CONH_2)=NOCH_3$, $C(CO_2CH_3)=NOCH_3$, $C(CONHCH_3)=NOCH_3$ or $N(OCH_3)-CO_2CH_3$;

N is 0 or 1;

$R^1$ is hydrogen or unsubstituted or substituted alkyl, alkenyl, alkynyl, cycloalkyl;

$R^2$ is hydrogen or unsubstituted or substituted alkyl, alkenyl, alkynyl, cycloalkyl, $R^3$ is hydrogen, halogen, $C_1$–$C_4$-alkyl or $C_1$–$C_2$-haloalkyl;

x is 0, 1 or 2, it being possible for the radicals $R^4$ to be different if x is 2;

$R^4$ is cyano, nitro, halogen or $C_1$–$C_2$-alkyl, $C_1$–$C_2$-alkoxy, unsubstituted or substituted alkyl, alkenyl, alkynyl or cycloalkyl;

y is 0, 1, 2 or 3, it being possible for the radicals $R^5$ to be different if y is 2 or 3;

$R^5$ is cyano, halogen, $C_1$–$C_4$-alkyl, $C_1$–$C_4$-haloalkyl or $C_1$–$C_4$-alkoxy.

2. A composition which is suitable for controlling pests or harmful fungi, comprising a solid or liquid carrier and a compound of the general formula I as claimed in claim 1.

3. A method of controlling harmful fungi, which comprises treating the fungi, or the materials, plants, the soil or seeds to be protected against fungal infection, with an effective amount of a compound of the general formula I as claimed in claim 1.

4. A method of controlling pests, which comprises treating the pests, or the materials, plants, the soil or seeds to be protected against them, with an effective amount of a compound of the general formula I as claimed in claim 1.

* * * * *